United States Patent
Licht et al.

(10) Patent No.: US 12,167,903 B2
(45) Date of Patent: Dec. 17, 2024

(54) METHODS OF SMOOTHLY ARTICULATING MEDICAL DEVICES HAVING MULTI-CLUSTER JOINTS

(71) Applicant: FlexDex, Inc., Brighton, MI (US)

(72) Inventors: James Michael Licht, Howell, MI (US); Shorya Awtar, Ann Arbor, MI (US); Deepak Sharma, Ann Arbor, MI (US); Zachary Zimmerman, Waterford, MI (US); Bruce Johnson, Elkins, NH (US); Christopher K. Holmes, Harvard, MA (US); Peter F. Costa, Winthrop, MA (US); Brian Douglas Larose, Cornish, NH (US); Randall Sullivan, Howell, MI (US); Ryan Brook Rank, Ann Arbor, MI (US)

(73) Assignee: FlexDex, Inc., Brighton, MI (US)

( * ) Notice: Subject to any disclaimer, the term of this patent is extended or adjusted under 35 U.S.C. 154(b) by 797 days.

(21) Appl. No.: 17/216,662

(22) Filed: Mar. 29, 2021

(65) Prior Publication Data
US 2021/0212785 A1 Jul. 15, 2021

Related U.S. Application Data

(63) Continuation of application No. 15/286,489, filed on Oct. 5, 2016, now Pat. No. 10,959,797.
(Continued)

(51) Int. Cl.
*A61B 17/29* (2006.01)
*A61B 1/005* (2006.01)
(Continued)

(52) U.S. Cl.
CPC .............. *A61B 34/71* (2016.02); *A61B 1/005* (2013.01); *A61B 17/29* (2013.01); *A61B 34/30* (2016.02);
(Continued)

(58) Field of Classification Search
CPC ......... A61B 34/71; A61B 34/76; A61B 17/29; A61B 2017/00314; A61B 2017/00323; A61B 2034/306
See application file for complete search history.

(56) References Cited

U.S. PATENT DOCUMENTS

| | | |
|---|---|---|
| 331,598 A | 12/1885 | White |
| 3,028,126 A | 4/1962 | Holleman |

(Continued)

FOREIGN PATENT DOCUMENTS

| | | |
|---|---|---|
| CN | 101610709 A | 12/2009 |
| CN | 101711703 A | 5/2010 |

(Continued)

OTHER PUBLICATIONS

Awtar et al.; A minimally invasive surgical tool with enhanced dexterity and intuitive actuation; J. Med. Devices; 4(3); 8 pages; (Author's Draft; 12 pages); Sep. 10, 2010.
(Continued)

*Primary Examiner* — Elizabeth Houston
*Assistant Examiner* — Jonathan A Hollm
(74) *Attorney, Agent, or Firm* — Shay Glenn LLP

(57) ABSTRACT

An articulating joint comprising a multi-cluster joint where every consecutive pair of links is interfaced by a gimbal, which offers rotation about two orthogonal axes within the same plane. Thus, the articulating joint comprises an alternating sequence of links and gimbals. Furthermore, there may be multiple cables attached to one or more of the links. As these cables are selectively pulled and released, one can
(Continued)

achieve any desired articulation of the articulating joint. There may be a transmission member extending through the links and gimbals, parallel to the central longitudinal axis of the joint in its nominal non-articulated condition. This transmission member may be either a tension member that is pulled on (e.g. a cable or flexible pull rod) and that loads the articulating joint in compression, or the transmission member may be a flexible push rod that loads the articulating joint in tension.

18 Claims, 25 Drawing Sheets

Related U.S. Application Data

(60) Provisional application No. 62/237,483, filed on Oct. 5, 2015, provisional application No. 62/237,476, filed on Oct. 5, 2015.

(51) Int. Cl.
*A61B 34/00* (2016.01)
*A61B 34/30* (2016.01)
*A61B 17/00* (2006.01)
*A61B 90/00* (2016.01)
*B25J 9/06* (2006.01)
*B25J 9/10* (2006.01)

(52) U.S. Cl.
CPC .... *A61B 34/76* (2016.02); *A61B 2017/00314* (2013.01); *A61B 2017/00323* (2013.01); *A61B 2017/2908* (2013.01); *A61B 2034/306* (2016.02); *A61B 2034/715* (2016.02); *A61B 2090/031* (2016.02); *B25J 9/06* (2013.01); *B25J 9/104* (2013.01)

(56) References Cited

U.S. PATENT DOCUMENTS

| | | | |
|---|---|---|---|
| 3,350,956 A | 11/1967 | Barton |
| 3,497,083 A | 2/1970 | Anderson et al. |
| 3,656,235 A | 4/1972 | Zuurveen |
| 4,328,839 A | 5/1982 | Lyons et al. |
| 4,466,649 A | 8/1984 | Ozawa |
| 4,491,325 A | 1/1985 | Bersheim |
| 4,568,311 A | 2/1986 | Miyake |
| 4,613,179 A | 9/1986 | van Zelm |
| 4,712,545 A | 12/1987 | Honkanen |
| 4,740,126 A | 4/1988 | Richter |
| 4,750,475 A | 6/1988 | Yoshihashi |
| 4,754,909 A | 7/1988 | Barker et al. |
| 4,758,035 A | 7/1988 | Shimasaki |
| 4,950,273 A | 8/1990 | Briggs |
| 4,993,766 A | 2/1991 | Sutherland |
| 5,021,969 A | 6/1991 | Okamura et al. |
| 5,036,724 A | 8/1991 | Rosheim |
| 5,069,596 A | 12/1991 | Mueller et al. |
| 5,147,357 A | 9/1992 | Rose et al. |
| 5,193,963 A | 3/1993 | McAffee et al. |
| 5,209,747 A | 5/1993 | Knoepfler |
| 5,297,443 A | 3/1994 | Wentz |
| 5,317,952 A | 6/1994 | Immega |
| 5,323,570 A | 6/1994 | Kuhlman et al. |
| 5,330,502 A | 7/1994 | Hassler et al. |
| 5,350,391 A | 9/1994 | Iacovelli |
| 5,368,600 A | 11/1994 | Failla et al. |
| 5,374,277 A | 12/1994 | Hassler |
| 5,379,663 A | 1/1995 | Hara |
| 5,379,758 A | 1/1995 | Snyder |
| 5,454,827 A | 10/1995 | Aust et al. |
| 5,456,695 A | 10/1995 | Herve Dallemagne |
| 5,465,894 A | 11/1995 | Clark et al. |
| 5,549,637 A | 8/1996 | Crainich |
| 5,560,532 A | 10/1996 | DeFonzo et al. |
| 5,599,151 A | 2/1997 | Daum et al. |
| 5,619,195 A | 4/1997 | Allen et al. |
| 5,620,415 A | 4/1997 | Lucey et al. |
| 5,626,608 A | 5/1997 | Cuny et al. |
| 5,683,412 A | 11/1997 | Scarfone |
| 5,713,505 A | 2/1998 | Huitema |
| 5,716,352 A | 2/1998 | Viola et al. |
| 5,735,874 A | 4/1998 | Measamer et al. |
| 5,782,748 A | 7/1998 | Palmer et al. |
| 5,807,376 A | 9/1998 | Viola et al. |
| 5,810,880 A | 9/1998 | Jensen et al. |
| 5,813,813 A | 9/1998 | Daum et al. |
| 5,816,770 A | 10/1998 | Itagaki |
| 5,817,084 A | 10/1998 | Jensen |
| 5,820,009 A | 10/1998 | Melling et al. |
| 5,853,412 A | 12/1998 | Mayenberger |
| 5,860,995 A | 1/1999 | Berkelaar |
| 5,908,436 A | 6/1999 | Cuschieri et al. |
| 6,042,555 A | 3/2000 | Kramer et al. |
| 6,088,020 A | 7/2000 | Mor et al. |
| 6,104,379 A | 8/2000 | Petrich et al. |
| 6,270,453 B1 | 8/2001 | Sakai |
| 6,309,403 B1 | 10/2001 | Minor et al. |
| 6,312,435 B1 | 11/2001 | Wallace et al. |
| 6,330,837 B1 | 12/2001 | Charles et al. |
| 6,413,229 B1 | 7/2002 | Kramer et al. |
| 6,607,475 B2 | 8/2003 | Doyle et al. |
| 6,707,447 B1 | 3/2004 | Goranowski |
| 6,714,839 B2 | 3/2004 | Salisbury et al. |
| 6,853,879 B2 | 2/2005 | Sunaoshi |
| 6,858,005 B2 | 2/2005 | Ohline et al. |
| 6,889,116 B2 | 5/2005 | Jinno |
| 6,994,716 B2 | 2/2006 | Jinno et al. |
| 7,101,363 B2 | 9/2006 | Nishizawa et al. |
| 7,147,650 B2 | 12/2006 | Lee |
| 7,331,967 B2 | 2/2008 | Lee et al. |
| 7,338,513 B2 | 3/2008 | Lee et al. |
| 7,410,338 B2 | 8/2008 | Schiele et al. |
| 7,470,268 B2 | 12/2008 | Doyle et al. |
| 7,524,320 B2 | 4/2009 | Tierney et al. |
| 7,553,275 B2 | 6/2009 | Padget et al. |
| 7,608,083 B2 | 10/2009 | Lee et al. |
| 7,708,756 B2 | 5/2010 | Nobis et al. |
| 7,736,254 B2 | 6/2010 | Schena |
| 7,862,554 B2 * | 1/2011 | Hegeman ............ A61B 1/0055 606/1 |
| 7,866,527 B2 | 1/2011 | Hall et al. |
| 7,947,035 B2 | 5/2011 | Miyamoto et al. |
| 7,963,913 B2 | 6/2011 | Devengenzo et al. |
| 8,029,531 B2 | 10/2011 | Lee et al. |
| 8,057,487 B2 | 11/2011 | Chu et al. |
| 8,105,319 B2 | 1/2012 | Doyle et al. |
| 8,105,350 B2 | 1/2012 | Lee et al. |
| 8,365,633 B2 | 2/2013 | Simaan et al. |
| 8,398,587 B2 | 3/2013 | Dewaele et al. |
| 8,398,634 B2 | 3/2013 | Scott et al. |
| 8,425,408 B2 | 4/2013 | Boulais et al. |
| 8,465,475 B2 | 6/2013 | Isbell |
| 8,528,440 B2 | 9/2013 | Morley et al. |
| 8,540,748 B2 | 9/2013 | Murphy et al. |
| 8,551,076 B2 | 10/2013 | Duval et al. |
| 8,603,135 B2 | 12/2013 | Mueller |
| 8,668,702 B2 | 3/2014 | Awtar et al. |
| 8,672,206 B2 | 3/2014 | Aranyi et al. |
| 8,764,448 B2 | 7/2014 | Yang et al. |
| 8,777,898 B2 | 7/2014 | Suon et al. |
| 8,821,512 B2 | 9/2014 | Barrier et al. |
| 8,870,867 B2 | 10/2014 | Walberg et al. |
| 8,881,616 B2 | 11/2014 | Dize et al. |
| 8,968,355 B2 | 3/2015 | Malkowski et al. |
| 8,992,422 B2 | 3/2015 | Spivey et al. |
| 9,050,121 B2 | 6/2015 | Doyle |
| 9,060,796 B2 | 6/2015 | Seo |
| 9,161,771 B2 | 10/2015 | Steger |
| 9,220,398 B2 | 12/2015 | Woodley et al. |
| 9,339,342 B2 | 5/2016 | Prisco et al. |
| 9,522,014 B2 | 12/2016 | Nishizawa et al. |

(56) References Cited

U.S. PATENT DOCUMENTS

| | | |
|---|---|---|
| 9,532,839 B2 | 1/2017 | Seo |
| 9,575,504 B2 | 2/2017 | Dize et al. |
| 9,579,013 B2 | 2/2017 | Dewaele et al. |
| 9,622,729 B2 | 4/2017 | Dewaele et al. |
| 9,629,682 B2 | 4/2017 | Wallace et al. |
| 9,629,689 B2 | 4/2017 | Bowles et al. |
| 9,649,096 B2 | 5/2017 | Sholev |
| 9,675,370 B2 | 6/2017 | Awtar et al. |
| 9,695,916 B2 | 7/2017 | Lee |
| 9,696,700 B2 | 7/2017 | Beira et al. |
| 9,770,300 B2 | 9/2017 | Kwon et al. |
| 9,814,451 B2 | 11/2017 | Sharma et al. |
| 9,869,339 B2 | 1/2018 | Zimmerman et al. |
| 9,993,258 B2 | 1/2018 | Shelton, IV et al. |
| 9,889,874 B1 | 2/2018 | Clause |
| 9,955,988 B2 | 5/2018 | Stefanchik et al. |
| 10,005,181 B2 | 6/2018 | Hasegawa et al. |
| 10,085,624 B2 | 10/2018 | Isoda et al. |
| 10,198,086 B2 | 2/2019 | Parazynski et al. |
| 10,271,913 B2 | 4/2019 | Yoshii et al. |
| 10,325,072 B2 | 6/2019 | Beira et al. |
| 10,363,055 B2 | 7/2019 | Beira et al. |
| 10,405,936 B2 | 9/2019 | Awtar et al. |
| 10,449,010 B2 | 10/2019 | Dewaele et al. |
| 10,617,413 B2 | 4/2020 | Shelton et al. |
| 10,660,719 B2 | 5/2020 | Mathelin et al. |
| 10,660,721 B2 | 5/2020 | Bonny et al. |
| 10,664,002 B2 | 5/2020 | Parazynsk et al. |
| 10,695,141 B2 | 6/2020 | Lee |
| 10,709,467 B2 | 7/2020 | Lee et al. |
| 10,722,315 B2 | 7/2020 | Lee et al. |
| 10,753,439 B2 | 8/2020 | Awtar |
| 10,959,797 B2 | 3/2021 | Licht et al. |
| 11,344,381 B2 | 5/2022 | Lee et al. |
| 11,490,980 B2 | 11/2022 | Lee et al. |
| 11,510,746 B2 | 11/2022 | Lee et al. |
| 2001/0031983 A1 | 10/2001 | Brock et al. |
| 2003/0036748 A1 | 2/2003 | Cooper et al. |
| 2003/0135203 A1 | 7/2003 | Wang et al. |
| 2003/0135204 A1 | 7/2003 | Lee et al. |
| 2003/0153902 A1 | 8/2003 | Doyle et al. |
| 2003/0176880 A1 | 9/2003 | Long et al. |
| 2003/0176948 A1 | 9/2003 | Green |
| 2004/0068274 A1 | 4/2004 | Hooven |
| 2004/0138700 A1 | 7/2004 | Cooper et al. |
| 2004/0236316 A1 | 11/2004 | Danitz et al. |
| 2004/0253079 A1 | 12/2004 | Sanchez |
| 2005/0004431 A1 | 1/2005 | Kogasaka et al. |
| 2005/0038469 A1 | 2/2005 | Lang |
| 2005/0090811 A1 | 4/2005 | Doyle et al. |
| 2005/0107667 A1 | 5/2005 | Danitz et al. |
| 2005/0119692 A1 | 6/2005 | Szabo |
| 2006/0111210 A1 | 5/2006 | Hinman |
| 2006/0111616 A1 | 5/2006 | Danitz |
| 2006/0156848 A1 | 7/2006 | Gosselin et al. |
| 2006/0190034 A1 | 8/2006 | Nishizawa et al. |
| 2006/0199999 A1 | 9/2006 | Ikeda et al. |
| 2006/0259073 A1 | 11/2006 | Miyamoto et al. |
| 2006/0282063 A1 | 12/2006 | Gotani |
| 2007/0021738 A1 | 1/2007 | Hasser et al. |
| 2007/0022562 A1 | 2/2007 | Hampton |
| 2007/0072466 A1 | 3/2007 | Miyamoto et al. |
| 2007/0078565 A1 | 4/2007 | Ghodoussi et al. |
| 2007/0093790 A1 | 4/2007 | Downey et al. |
| 2008/0004493 A1 | 1/2008 | Schiemann |
| 2008/0039256 A1 | 2/2008 | Jinno et al. |
| 2008/0065098 A1 | 3/2008 | Larkin |
| 2008/0177285 A1* | 7/2008 | Brock ............... A61B 34/71 606/1 |
| 2008/0193260 A1 | 8/2008 | Yokokohji et al. |
| 2008/0221591 A1 | 9/2008 | Farritor et al. |
| 2008/0243176 A1 | 10/2008 | Weitzner et al. |
| 2009/0118044 A1 | 5/2009 | Kuo et al. |
| 2009/0171147 A1 | 7/2009 | Lee et al. |
| 2009/0171374 A1* | 7/2009 | Omori ............... A61B 34/71 606/130 |
| 2009/0192511 A1 | 7/2009 | Haffenreffer |
| 2010/0004606 A1 | 1/2010 | Hansen et al. |
| 2010/0016853 A1 | 1/2010 | Burbank |
| 2010/0030018 A1 | 2/2010 | Fortier et al. |
| 2010/0056863 A1 | 3/2010 | Dejima et al. |
| 2010/0111645 A1 | 5/2010 | Al-Mouhamed et al. |
| 2010/0234831 A1 | 9/2010 | Hinman et al. |
| 2010/0249497 A1 | 9/2010 | Peine et al. |
| 2011/0024145 A1 | 2/2011 | Click et al. |
| 2011/0093005 A1 | 4/2011 | Strokosz et al. |
| 2011/0106145 A1 | 5/2011 | Jeong |
| 2011/0112517 A1 | 5/2011 | Peine et al. |
| 2011/0118707 A1 | 5/2011 | Burbank |
| 2011/0152881 A1 | 6/2011 | Conner et al. |
| 2011/0152922 A1 | 6/2011 | Jeong |
| 2011/0178531 A1 | 7/2011 | Caputo et al. |
| 2011/0319911 A1 | 12/2011 | Conner et al. |
| 2012/0083799 A1 | 4/2012 | Chen et al. |
| 2012/0095298 A1 | 4/2012 | Stefanchik et al. |
| 2012/0118097 A1 | 5/2012 | Ilch |
| 2012/0152055 A1 | 6/2012 | Lechuga Priego |
| 2012/0186383 A1 | 7/2012 | Schvalb et al. |
| 2012/0271283 A1 | 10/2012 | Doyle |
| 2012/0277762 A1 | 11/2012 | Lathrop et al. |
| 2013/0012958 A1 | 1/2013 | Marczyk et al. |
| 2013/0023868 A1 | 1/2013 | Worrell et al. |
| 2013/0066334 A1 | 3/2013 | Schoepp |
| 2013/0172860 A1 | 7/2013 | Szewczyk et al. |
| 2013/0239734 A1 | 9/2013 | Hinman |
| 2014/0135762 A1 | 5/2014 | Masuda et al. |
| 2014/0135805 A1 | 5/2014 | Windgassen et al. |
| 2014/0246471 A1 | 9/2014 | Jaworek et al. |
| 2014/0331798 A1 | 11/2014 | Shim et al. |
| 2014/0371532 A1 | 12/2014 | Trovato |
| 2015/0021068 A1 | 1/2015 | Bernhardt et al. |
| 2015/0053455 A1 | 2/2015 | Hagi |
| 2015/0164601 A1 | 6/2015 | Sholev |
| 2015/0209059 A1 | 7/2015 | Trees et al. |
| 2015/0230697 A1 | 8/2015 | Phee et al. |
| 2016/0135830 A1 | 5/2016 | Volkmer et al. |
| 2017/0245954 A1 | 8/2017 | Beira et al. |
| 2017/0360522 A1 | 12/2017 | Beira et al. |
| 2018/0000318 A9 | 1/2018 | Rogers et al. |
| 2018/0049842 A1 | 2/2018 | Bowles et al. |
| 2018/0125519 A1 | 5/2018 | Beira et al. |
| 2018/0125592 A1 | 5/2018 | Beira |
| 2018/0221045 A1 | 8/2018 | Zimmerman et al. |
| 2018/0289384 A1 | 10/2018 | Bowles et al. |
| 2019/0133698 A1 | 5/2019 | Beira et al. |
| 2019/0336230 A1 | 11/2019 | Awater et al. |
| 2020/0121406 A1 | 4/2020 | Lee |
| 2020/0146766 A1 | 5/2020 | Lee |
| 2020/0229835 A1 | 7/2020 | Lee et al. |
| 2020/0352562 A1 | 11/2020 | Timm et al. |
| 2021/0038865 A1 | 2/2021 | Sharma et al. |
| 2021/0045765 A1 | 2/2021 | Zimmerman et al. |
| 2021/0045825 A1 | 2/2021 | Lee et al. |
| 2022/0273381 A1 | 9/2022 | Lee et al. |
| 2023/0034145 A1 | 2/2023 | Awtar et al. |
| 2024/0148398 A1 | 5/2024 | Zimmerman et al. |

FOREIGN PATENT DOCUMENTS

| | | |
|---|---|---|
| CN | 103505265 A | 1/2014 |
| CN | 104889974 A | 9/2015 |
| EP | 0356664 A1 | 3/1990 |
| EP | 2810745 A1 | 12/2014 |
| EP | 2923646 A2 | 9/2015 |
| EP | 2923662 A2 | 9/2015 |
| EP | 3232951 A2 | 6/2016 |
| EP | 3232952 A1 | 6/2016 |
| EP | 3232973 A1 | 6/2016 |
| EP | 3232974 A2 | 6/2016 |
| EP | 3232977 A1 | 6/2016 |
| EP | 3340897 A1 | 3/2017 |
| GB | 973587 A | 10/1964 |
| GB | 2513326 A | 10/2014 |

(56) References Cited

FOREIGN PATENT DOCUMENTS

| | | |
|---|---|---|
| GB | 2552540 A | 1/2018 |
| GB | 2552541 A | 1/2018 |
| JP | 3-292879 A | 12/1991 |
| JP | H06-262549 A | 9/1994 |
| JP | 8-84702 A | 4/1996 |
| JP | H09-96146 A | 4/1997 |
| JP | 2002102248 A | 4/2002 |
| JP | 2003061969 A | 3/2003 |
| JP | 2007130485 A | 5/2007 |
| JP | 2008531222 A | 8/2008 |
| JP | 2009127289 A | 6/2009 |
| JP | 2009136684 | 6/2009 |
| JP | 2012513823 A | 6/2012 |
| JP | 2013507196 A | 3/2013 |
| JP | 2013070861 A | 4/2013 |
| JP | 6220085 B2 | 10/2017 |
| WO | WO2006/036067 A2 | 4/2006 |
| WO | WO2007/137304 A2 | 11/2007 |
| WO | WO2007/146894 A2 | 12/2007 |
| WO | WO2008/020964 A2 | 2/2008 |
| WO | WO2010/104755 A1 | 9/2010 |
| WO | WO2013/027203 A1 | 2/2013 |
| WO | WO2014/033717 A1 | 3/2014 |
| WO | WO2015/125140 A1 | 8/2015 |
| WO | WO2016/063213 A1 | 4/2016 |
| WO | WO2016/161449 A1 | 10/2016 |
| WO | WO2017/059442 A1 | 4/2017 |
| WO | WO2017/062516 A1 | 4/2017 |
| WO | WO2017/062529 A1 | 4/2017 |

OTHER PUBLICATIONS

Clement et al.; Design of a Snake-Like Manipulator; Robotics and Autonomous Systems; 6(3); pp. 265-282; Jul. 1990.

Do et al.; Adaptive control of position compensation for cable-conduit mechanisms used in flexible surgical robots; Proceedings of the 11th International Conference on Informatics in Control, Automation and Robotics (ICINCO-2014); IEEE: pp. 110-117; Sep. 1, 2014.

Ikuta et al.; Shape Memory Alloy Servo Actuator System With Electric Resistance Feedback And Application For Active Endoscope (conf. paper); 1988 IEEE Int'l Conf. on Robotics and Automation; pp. 427-430; Apr. 24-29, 1988.

Jug et al.; The JPL Serpentine Robot: a 12 DOF System for Inspection (Conference Paper); Proceedings—IEEE International Conference on Robotics and Automation 3: 5 pgs.; Jun. 1995.

Peirs et al.; A flexible distal tip with two degrees of freedom for enhanced dexterity in endoscopic robot surgery; MME'02; The 13th Micromechanics Europe Workshop; Sinaia, Romania; pp. 271-274; Oct. 6-8, 2002.

Simaan et al.; A dexterous system for laryngeal surgery; Proceedings of the 2004 IEEE International Conference on Robotics and Automation; New Orleans, LA.; pp. 351-357; Apr. 2004.

Walker et al.; Novel 'Elephant"s Trunk' Robot; IEEE/ASME International Conference on Advanced Intelligent Mechatronics, AIM; Piscataway, NJ, United States; pp. 410-415; Sep. 19-23, 1999.

Wikipedia; Constant Velocity Joint; 6 pgs.; retrieved from the internet (https://en.wikipedia.org/wiki/Constant-velocity_joint) on Dec. 22, 2016.

Wikipedia; Six-bar linkage; 2 pgs; retrieved from the internet (https://en.wikipedia.org/w/index.php?title=Six-bar_linkage&oldid=670945266) on Apr. 26, 2019.

\* cited by examiner

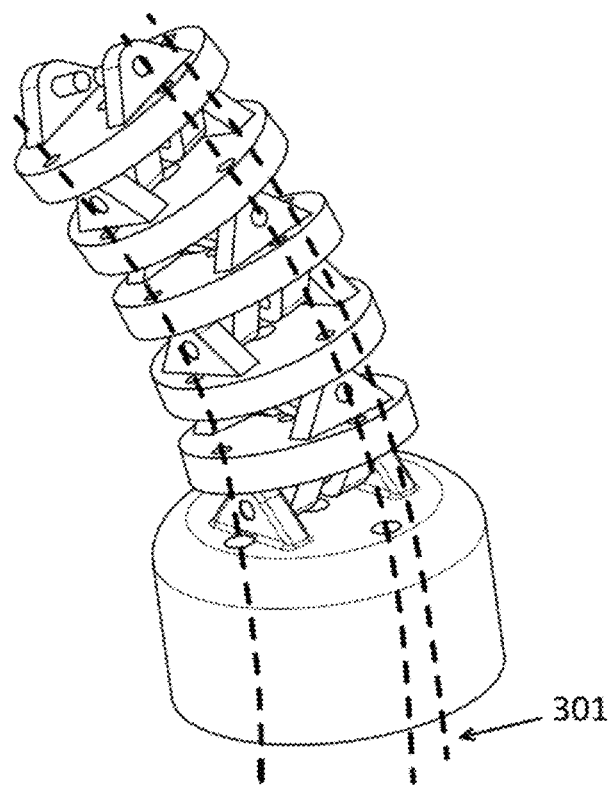
FIG. 3
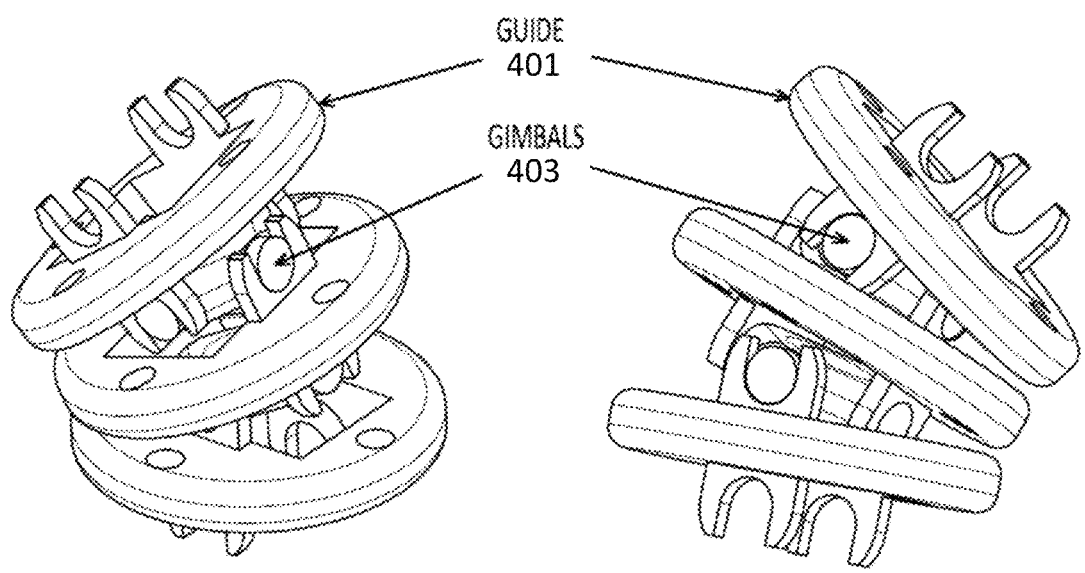
FIG. 4A
FIG. 4B

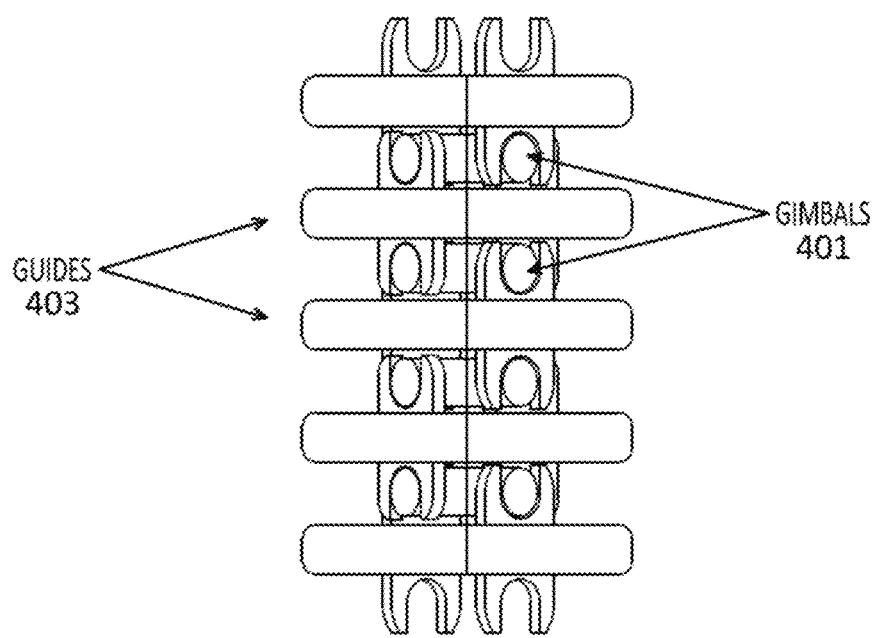
FIG. 4C
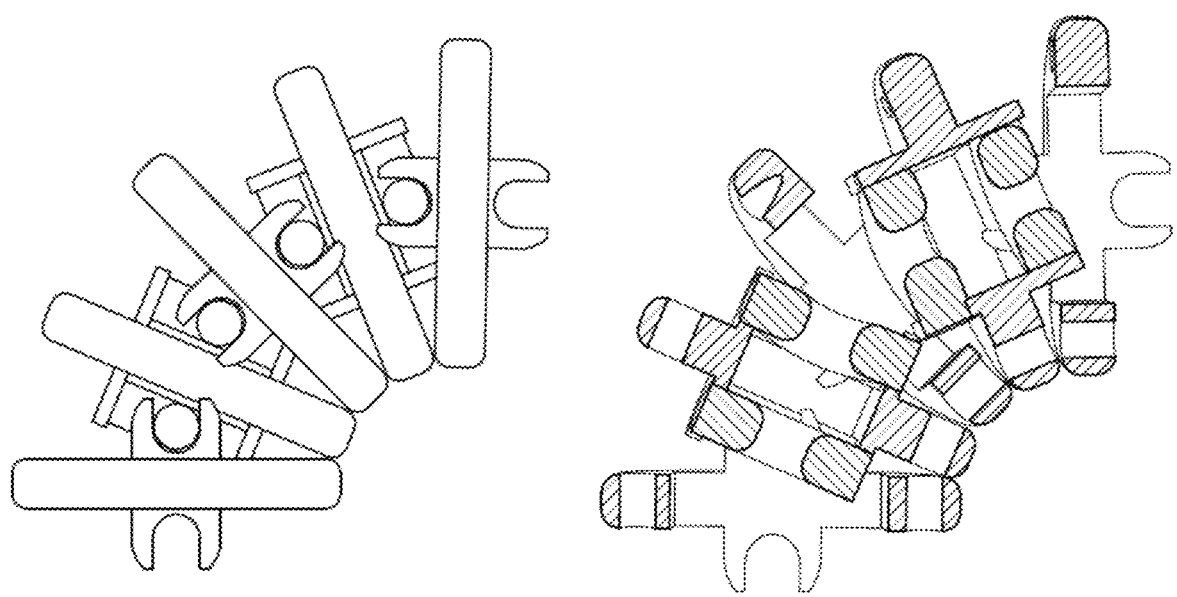
FIG. 5A
FIG. 5B

SECTION A-A

SECTION A-A

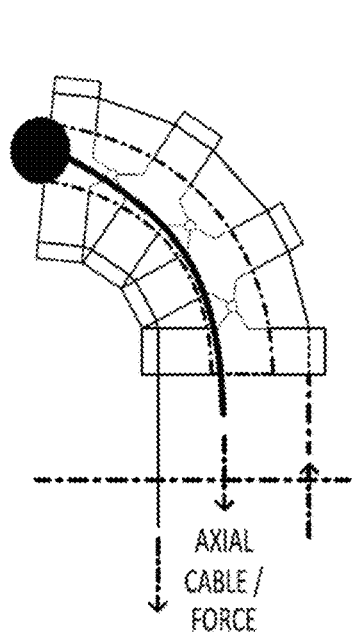
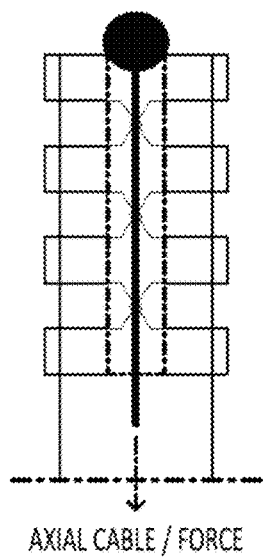
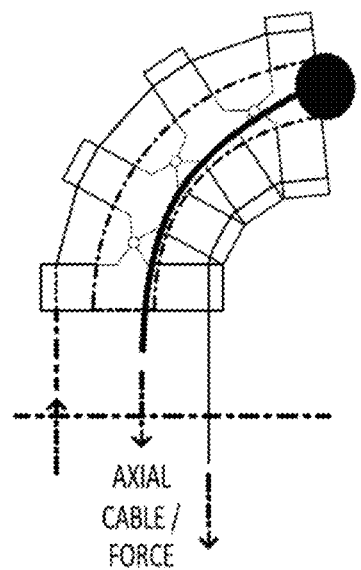
FIG. 18A  FIG. 18B  FIG. 18C
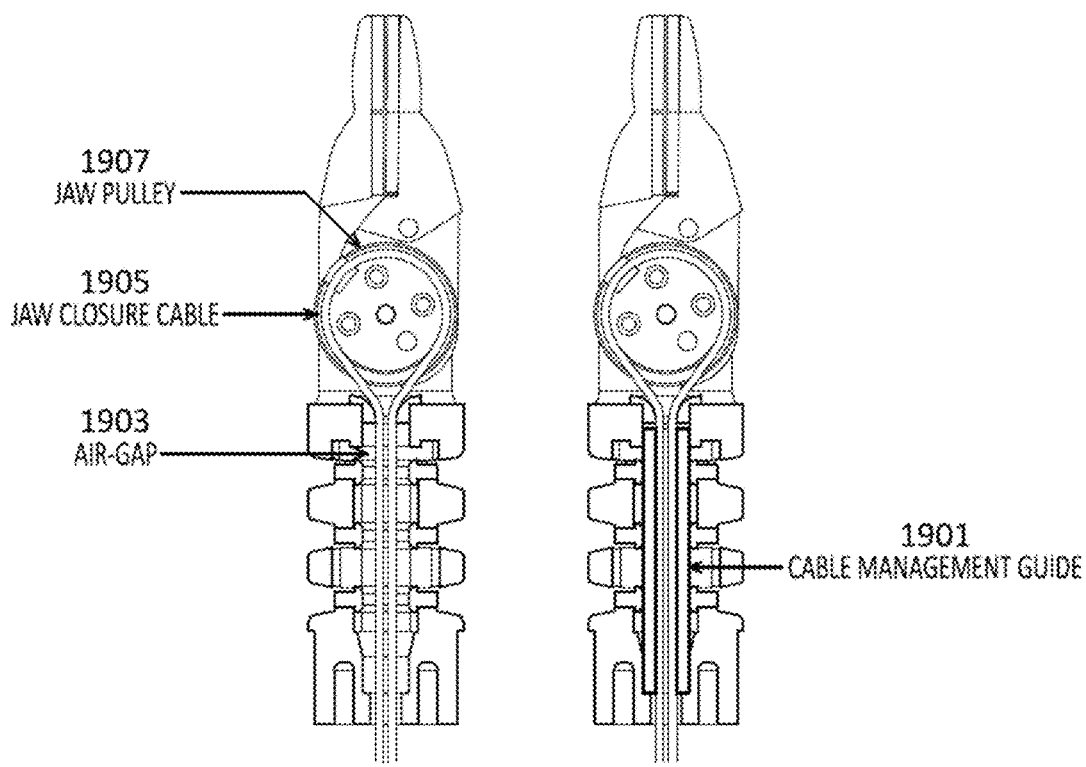
FIG. 19A  FIG. 19B

METHODS OF SMOOTHLY ARTICULATING MEDICAL DEVICES HAVING MULTI-CLUSTER JOINTS

CROSS REFERENCE TO RELATED APPLICATIONS

This patent application is a continuation of U.S. patent application Ser. No. 15/286,489, filed Oct. 5, 2016, titled "MEDICAL DEVICES HAVING SMOOTHLY ARICULATING MULTI-CLUSTER JOINTS," now U.S. Pat. No. 10,959,797, which claims priority to U.S. Provisional Patent Application No. 62/237,483, titled "ARTICULATING JOINT AND SUPPORTING MEMBER THEREOF" filed on Oct. 5, 2015; and U.S. Provisional Patent Application No. 62/237,476, titled "END-EFFECTOR JAW CLOSURE TRANSMISSION SYSTEMS FOR REMOTE ACCESS TOOLS" filed on Oct. 5, 2015, each of which is herein incorporated by reference in its entirety.

This application may also be related to U.S. patent application Ser. No. 15/130,915, titled "ATTACHMENT APPARATUS FOR REMOTE ACCESS TOOLS", filed on Apr. 15, 2016, which claimed priority to U.S. Provisional Patent Application No. 62/147,998, titled "FOREARM ATTACHMENT APPARATUS FOR REMOTE ACCESS TOOLS" filed on Apr. 15, 2015, and U.S. Provisional Patent Application No. 62/236,805, titled "FOREARM ATTACHMENT APPARATUS FOR REMOTE ACCESS TOOLS" filed on Oct. 2, 2015. This application may also be related to U.S. patent application Ser. No. 15/054,068, titled "PARALLEL KINEMATIC MECHANISMS WITH DECOUPLED ROTATIONAL MOTIONS" filed on Feb. 25, 2016, which claims priority as a continuation-in-part of U.S. patent application Ser. No. 14/166,503, titled "MINIMAL ACCESS TOOL" filed on Jan. 28, 2014, Publication No. US-2014-0142595-A1, which is a continuation of U.S. patent application Ser. No. 12/937,523, titled "MINIMUM ACCESS TOOL" filed on Apr. 13, 2009, now U.S. Pat. No. 8,668,702, which claimed priority to U.S. Provisional Patent Application No. 61/044,168, titled "MINIMALLY INVASIVE SURGICAL TOOL" filed on Apr. 11, 2008. Each of these patents and patent applications is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are multi-cluster articulating joints that may articulate an end-effector for remote access instruments, for example minimally invasive surgical tools.

BACKGROUND

A variety of articulating remote access tools (U.S. Pat. Nos. 5,330,502, 8,029,531 B2, U.S. application Ser. No. 13/865,790) have output articulation joints that include one or more links, multi-links, or clusters which can be controlled by one or more tension members (e.g. articulation cables or articulation transmission cables). These particular combinations of links, clusters, components and tension members can be useful for the purpose of steering an end-effector (EE) for remote access and manipulation of an instrument, specifically a laparoscopic or endoscopic surgical instrument. Since these devices utilize articulating end-effector joints that are generally controlled by tension members (e.g. articulation cables), these devices can be articulated or manipulated via an articulation input generally present in the proximal region of the tool. For example, articulation or manipulation of an articulation input (performed manually or electromechanically) that is coupled with tension members/articulation transmission cables may lead to articulation of the end-effector via an output articulation joint/multi-link end-effector joint (U.S. Pat. No. 8,668,702). The end-effector may include many different embodiments and may not be limited to a pair of jaws. Other embodiments may be useful for holding and manipulation of needles, suture, tissue, cautery, ligation clip application, etc., or it may function in the form of a camera for steerable laparoscopic/endoscopic visualization and/or diagnostics. For any of these uses or other embodiments, articulating mechanisms can provide necessary degrees of freedom to help steer these end-effectors. As used herein, the terms "joint" and "mechanism" may be used equivalently. For minimally invasive surgical tools and procedures, and in particular laparoscopic and endoscopic procedures, an end-effector having an articulation joint may be necessary to provide highly dexterous and wrist-like motions similar to those of a surgeon's own wrist, but in a miniature size. This enhanced dexterity enables complex laparoscopic tasks, including needle driving along the curve of a suturing needle through various tissue planes, tissue dissection and retraction, knot tying, etc. In general, end-effector articulation joints may be positioned between an elongate member such as an instrument/tool shaft that provides the remote access, and an end-effector that provides some functionality such as holding, grasping, dissecting, shearing etc. In order to accomplish the tasks listed above, the end-effector articulation joint must offer certain rotational degrees of freedom (DoF) to the end-effector with respect to the instrument shaft. Sec, e.g., FIGS. 1A and 1B. These DoF include two orthogonal rotations, generally referred to as the pitch and yaw rotations. In some instances, the roll rotation is constrained by the end-effector articulation joint.

Typically, the articulation joint is controlled by a plurality of tension members, such as wires or cables (e.g. flexible steel or Nitinol wire, steel cable, etc.), which traverse through or make attachments to specific links within a multi-link end-effector articulation joint or route through a complex series of pulleys and various components of the articulation joint to the end-effector. These tensile members are used for articulation of the multi-link articulation joint and in general, may be referred as end-effector articulation transmission cable(s), or as end-effector articulation cable(s) or as articulation cables, or the like. These types of systems have been demonstrated in various embodiments but typically suffer from performance tradeoffs that occur within cable-based actuation of end-effector articulation joints. Cable driven end-effector articulation joints for minimally invasive surgical tools are most practical due to the size constraints imposed on these instrument types due to increasingly smaller access port diameters driven by the desire for reduced patient trauma during surgery resulting in better post-surgery recovery. However, a number of practical tradeoffs plague cable-based articulation mechanisms. End-effector articulation joints for various laparoscopic surgeries may need to provide a large angular range of rotation in all rotational directions (especially, pitch and yaw rotational directions) to the end-effector to provide adequate reach and work space. Once the end-effector has rotated in one direction, in many articulation joints the transmission path for articulating in the other direction may be altered. This may also be associated with an increment of tension in one or more cables that help in articulating multi-link articulation joints and reduction in tension or generation of slack in the opposite cable(s). This may lead to unnecessary slack generation and/or backlash in the end-effector articulation. Various other challenges in design of the articulation joints arise from the performance attributes that have to be met and the associated conflicting tradeoffs that arise from an engineering and design stand-point, as discussed below. Existing solutions have typically required a complex sequence of multiple pulleys and other components, resulting in a design that is not conducive to miniaturization (See, e.g., U.S. Pat. Nos. 8,540,748, 7,101,363, and 8,528,440). Other exemplary devices include US 2010/0030018, Peirs, et. al. (Peirs, J., Brussel, H., Reynaerts, D., Gersem, G., 2002, "A Flexible Distal Tip with Two Degrees of Freedom for Enhanced Dexterity in Endoscopic Robot Surgery", MME'02, The 13th Micromechanics Europe Workshop, Sinaia, Romania) and Simaan et al. (Simaan, N., Tayloer, R., Flint, P., 2004, "A Dexterous System for Laryngeal Surgery", Proceedings of the 2004 IEEE International Conference on Robotics & Automation, New Orleans, LA.).

In a typical multi-link articulation joints, multiple links are joined together by two (or more) "articulation cables" per end-effector rotation and pass through holes (also referred to as articulation cable openings) on the periphery of the multiple links. See, e.g., FIGS. 2A and 2B). To achieve the desired large range of rotation, this design has to include multiple links. Sec, e.g., FIG. 3. The higher the number of links, the greater is the problem of cable slack and end-effector backlash. Further, a larger number of links in conjunction with a large jaw closure force (applied via high tension in end-effector actuation transmission cable) produces jumpiness or jerkiness at the end-effector as well as joint distortion (or S bending) due to a buckling-type phenomenon, described and illustrated below.

Large holding stiffness of the end-effector articulation joint and minimal backlash while holding an articulated orientation are typically necessary for precise control during use. In other words, once the input holds articulation cables "fixed" in a certain actuation (see FIG. 2A), the end-effector should also maintain a corresponding "fixed" articulated orientation. This provides the ability to push the end-effector against its surroundings, and also helps transmit force feedback from the distal tip of the tool back to the proximal aspect, sometimes through an input joint to a user's hand. However, in the multi-link end-effector design, the kinematics of deformation and compliance of the articulation cables is such that, for example, when the distal end link of the end-effector is articulated with respect to the base link of end-effector in one direction of rotation by tensioning an articulation cable or plurality of cables, slack gets developed on the opposed side cable 201 or plurality of cables (see FIG. 2B), and vice versa. Additional slack may arise due to cable stretch, wear, and assembly tolerances. This slack may lead to end-effector backlash and a loss in holding stiffness, as described, for example in international application PCT/US2016/025926 Apr. 4, 2016, titled "TENSION MANAGEMENT APPARATUS FOR CABLE-DRIVEN TRANSMISSION" and filed on Apr. 4, 2016, herein incorporated by reference in its entirety.

Typically, in applications (especially minimal invasive surgery tools) pertaining to holding an object in the end-effector and pushing/pulling it against or piercing it through the surroundings (e.g. holding and driving a needle through tissue), the grasping force applied by end-effector jaws should be high, especially when holding an object such as needle to prevent slipping or rotating in place. This can be achieved via a high tension in the end-effector actuation transmission cable (e.g. the jaw closure cable) that connects an input control at the input to the end-effector jaws. In general, end-effector actuation transmission cable may also be referred to as end-effector actuation cable, or as actuation cable, or as jaw closure cable, or end effector transmission cable or the like. However, when this cable is routed through the multi-link end-effector joint (as is desirable for low-diameter devices), the large tension in this cable produces a buckling type loading effect on the multi-link end-effector. This can potentially result in jerkiness of the end-effector during rotations (pitch, yaw and/or roll). This can also lead to joint distortion (S-bending), which is a consequence of the redundant local degrees of freedom associated with the multiple links of the articulation joint. Previous attempts to address this issue typically use multiple drive pulleys and cables per end-effector rotation direction, which adds considerably to the complexity, size, and cost of the overall tool design, defeating the goal of a creating a simple, low-cost, highly functional minimally invasive surgery (MIS) tool. Thus, there is a tradeoff between using a large number of end-effector links (to provide large range of rotational motion) versus using fewer links (to reduce the operational workspace volume of the tool and to minimize or reduce jerkiness, backlash, and cable slack and to allow large grasping force and holding stiffness).

The apparatuses (devices, tools, systems, mechanisms, etc.) and methods described herein may address the problems described above.

SUMMARY OF THE DISCLOSURE

In general, described herein are multi-cluster articulation joints that have a relatively tight bend radius and can be miniaturized; these devices may be articulated smoothly through a variety of articulations, including a relatively high angles, while avoiding distortion (e.g., S-bending) or jerkiness in articulation even when jaw closure actuation is applied by means of an end-effector actuation transmission cable running through the multi-cluster articulation joint. The multi-cluster joints described herein may be part of any appropriate apparatus, including, but not limited to, medical devices, robotic devices (including medical and non-medical robotic devices), and the like. These articulating multi-cluster joints may be particularly well suited for use with an end-effector attached to a distal end that can articulated by the multi-cluster joints and actuated by a cable (e.g., a cable that is compliant in compression, torsion and bending, such as a rope, braid, etc.) extending through the multi-cluster joint. Described herein are multi-cluster joints that are compact, may have radius of curvature, and a high degree of articulation angle.

In general, an articulation joint could be at the input of an apparatus (i.e. input joint) or an output of the apparatus (i.e. output joint) or at both input as well as output. Although the examples provided herein focus primarily on remote/minimal access device/instrument/tools for minimally invasive surgery, specifically end-effector multi-link articulation joints that serve as the output joint of such devices, as mentioned above, they may be used as part of any apparatus in which a compact and smoothly articulating joint may be desired. As with any joint, the multi-cluster articulation joints (referred to herein as "multi-cluster joints", "articulating end-effector joints". "end-effector joints", "articulation joints" or "articulating joints" unless the context indicates otherwise) described considered may allow certain relative motions/degrees of freedom between a tool-shaft and an end-effector, and may constrain the remaining motions. The relative motions allowed may include yaw and pitch rotations, as shown in FIGS. 1A and 1B. Both rotations are orthogonal to the longitudinal axis of the tool shaft.

The multi-cluster joints described, and any apparatus including them, may provide multiple benefits. For example, these multi-cluster joints may have a small overall lateral dimension, such as a small cylindrical diameter or "joint cluster diameter" when the joint in nominal or non-articulated. These multi-cluster joints may also have a tight bend radius during articulation. Each joint cluster may also provide up to two orthogonal degrees of rotational freedom relative to the longitudinal joint cluster axis.

In general the bend radius of a joint including a multi-cluster joint is understood to be the minimum radius that one can articulate the joint until an articulation limit is reached. As the angle of articulation of the joint is increased, the radius of curvature generally decreases. Unless otherwise specified, as used herein the bend radius may be understood to be measured from an inside curvature of the joint (e.g., along an outer surface of the multi-cluster along the inside edge forming the bend). It should be understood that the bend radius may alternatively be measured from a midline of the joint, or an outer surface of the joint along the outside edge forming the bend. Although the multi-cluster joints described herein may form segmented curves, it should be understood that unless otherwise specified, the bend radius may refer to a smooth curve best fitting the outer edges of (or a midline through) the joint. In some variations the overall bend angle may be averaged over sub-regions of the bent or bending multi-cluster joint. As will be described in greater detail below, these apparatuses (e.g., the multi-cluster joints) may have a bend radius that is described as relative to the diameter of the multi-cluster joint, or in some variations, the diameter of the elongate shaft to which the multi-cluster joint is attached and/or the diameter of the end-effector. For example, the diameter of the multi-cluster joint may be the diameter of the multi-cluster joint transverse to the multi-cluster joint in a un articulated ("straight" or in some variations, unarticulated) configuration. The diameter of the multi-cluster joint may be approximately the same as the diameter of the joint cluster, e.g., the diameter of the gimbal guide(s)/half-gimbal guide(s) forming the multi-cluster joint. Although the apparatuses described herein include multi-cluster joints having a somewhat uniform diameter (e.g., in variations formed by gimbal guides or half-gimbal guides, the gimbal guides/half-gimbal guides are all approximately the same diameter), in some variation, different sized gimbal guides may be used. In any of the multi-cluster joints described herein, the bend angle relative to the diameter in this case may be in reference to, unless specified otherwise, the average diameter of the multi-cluster joint (e.g., as measured from the outer perimeter of the multi-cluster joint). Alternatively, the minimum bend radius relative to the diameter in this case may be in reference to the maximum diameter of the multi-cluster joint, the median diameter of the multi-cluster joint, etc.

The multi-cluster joints described herein may subtend a large articulation angle. For example, the articulation angle may be larger per the number of clusters or the geometric variables which can be modified to control the structure of the units within the cluster and their interaction (gimbal guides and/or half-gimbal guides and gimbals).

In general, the multi-cluster joints described herein may withstand a high compressive force in the axial or longitudinal direction. This axial direction may be a constraint direction, and thus forces may be transmitted in this direction. Since the actuation force to open and/or close the end-effector jaws may be transmitted through the end-effector joint, this may load the end-effector joint in a compressive manner. Large actuation force for end-effector jaw opening and/or closing may be needed for holding objects (such as a needle) or tissue securely. This large compressive force on the end-effector joint may create a buckling-like loading condition at the end-effector joint that leads to undesirable symptoms that are addressed via the end-effector joint design. For example, the multi-cluster joint may assume a zig-zag shape also sometimes referred to as "S-bending", or "joint-distortion". Further, the multi-cluster joint may experience "jumping" when articulating across some positional changes (e.g., minimal top dead center jumpiness) during articulation.

To address these issues, the multi-cluster joints may be configured as to provide an easy path through the articulation joint for an end-effector actuation transmission cable, which may allow an end-effector coupled to the joint to provide a large jaw opening angle, the jaws may freely open/close in all articulated conditions, and the input force needed to achieve jaw closure in all articulated conditions may be the same (uniform or nearly uniform), and may generally be low (e.g., the apparatus may have a low input articulation force at the handle or at a location proximal to the tool shaft and distal end-effector). In one instance, the handle may include two inputs, namely articulation input that serves as an input to end-effector articulation and input control or control input that serves as an input to actuation of end-effector jaws. In general, articulation input may be referred as articulation handle input, or the like. Control input may be referred as input control, or as handle input control, or as jaw closure control, or as input lever, or as handle lever, or as button, or as trigger or the like. Handle by itself may be referred as input, or as handle input or the like. Handle, by itself, may not be limited to interface only with hands of the user. Various other common input methods of controlling the end-effector joint articulation are also envisioned.

In some variations of the multi-cluster joint described herein, the multi-cluster joint is configured from a plurality clusters (sub-clusters). Each cluster typically include a half-gimbal guide on either side of a gimbal (e.g., half-gimbal guide, gimbal, half-gimbal guide) These individual components illustrated below. Each cluster may be considered a form of universal joint because the cluster provides two orthogonal rotational degrees of freedom (a first rotational DOF, pitch and a second rotational DOF, yaw)), similar to a Cardan joint. Described herein, these clusters typically place the two orthogonal axes of rotations in the same plane (referred to herein as a "cluster plane"), thereby providing an axially/longitudinally compact joint, which may result in the relatively tight bend radii described herein. A multi-cluster joint comprising axially compact joint clusters may exhibit a relatively tight bend radius. These clusters may be serially connected, over and over, to create an axial serial stack-up of clusters (e.g., half-gimbal guide, gimbal, half-gimbal guide, half-gimbal guide, gimbal, half-gimbal guide, half-gimbal guide, gimbal, half-gimbal guide). This kind of a serial stack-up leads to an articulating joint that is also referred to as a multi-cluster joint (a type of multi-link joint, snake-like joint, etc.). The yaw and pitch rotations provided by each respective cluster in the entire stack-up are all redundant and may contribute to a larger angle of articulation. However, the joint is still said to have only two DoF (overall yaw rotation and overall pitch rotation). Note that adjacent half-gimbal guides (in adjacent clusters of a half-gimbal guide, gimbal, half-gimbal guide) may be part of a whole gimbal guide (back-to-back half-gimbal guides) or they may be secured rigidly together. The connection (a pair of collinear yokes) of each half-gimbal guide to the gimbal may be oriented in parallel and fall within the same vertical plane intersecting the straight (unarticulated) joint cluster axis or longitudinal axis of the joint (e.g., a line connecting the pair of yokes on one side of whole gimbal guide may be parallel to a line connecting the pair of yokes on the opposite side of the whole gimbal guide), or they may be perpendicular and the lines connecting each pair intersect the straight (unarticulated) joint cluster axis or longitudinal axis of the joint. A single multi-cluster joint may include all parallel whole gimbal guides or it may include all perpendicular whole gimbal guides, or it may include a mix of both (e.g., alternating perpendicular and parallel whole gimbal guides).

In general, a multi-cluster joint may be formed of a stack of gimbal guides and gimbals. The stack may be pinless (lacking discreet pins during formation of the component or assembly), so that the gimbal guides and gimbals are literally stacked so that spindles extending from the gimbal body may reside in open yokes in the gimbal guide. The extending spindles may include a pair of collinear spindles that form a fist axis and a second pair of collinear spindles that form a second axis wherein the first and second axes are orthogonal. The cables, when in tension.(e.g., actuating cables and/or jaw actuating cable) may hold the multi-cluster joint and its sub-clusters (comprising half-gimbal guide, gimbal, half gimbal guide) together under a compressive load.

In general, the multi-cluster articulation joint may be swept in a continuous manner. For example, continuous contact between consecutive gimbal guides at their axisymmetric articulation limit during articulation may be permitted thereby allowing for articulations in all directions to offer the same uniform minimum bend radius and angle of articulation, providing a 360 degree or greater (e.g., continuous) articulation sweep wherein the articulation joint and tool shaft is constrained from rotating about the central longitudinal axis of the unarticulated joint. To rotate the articulation joint or joint and tool shaft about the central longitudinal axis of the unarticulated joint while maintaining an articulated position of the joint in one direction, instead of sweeping, the joint would complete an articulated roll. The features that define the hard-stops (e.g., articulation limit) in any articulated direction are typically axi-symmetric, or symmetric about a central longitudinal axis (that is defined when the joints are unarticulated) and contribute to the perception of smooth articulation via continuous articulation sweep and/or likewise, continuous articulated roll.

Any of the multi-cluster joints described herein may include a central opening into which a conduit (e.g., cable management guide) is routed via the axial stack-up. This central opening is referred to based on the context of description. For example, it is referred to as "gimbal central opening" in context of gimbal(s), as "gimbal guide central opening" in context of gimbal guide(s) and "joint cluster central opening" in context of multi-link joint clusters or joint clusters. Even though it is referred to as central opening, it may or may not be symmetrically placed with respect to the joint cluster, gimbal or gimbal guide axis.

Also, the "central opening" may be different from the opening or through hole for end-effector articulation cables. Opening for end-effector articulation transmission cables may be referred as just "opening", or as "articulation cable opening", or as "through hole", or as "thru hole", or as "channels", or as "through channels" or the like. This cable management guide may provide bending stiffness to mitigate the s-bending errors, and may smooth out the articulation. The cable management guide may also manage the cables for jaw opening/closing actuation that are routed through the axial stack-up to prevent a top-dead center jumpiness. In general, cable management guide may be referred as conduit, or as cable guide, or as cylindrical cable management guide body or the like. Also, even though the overall profile of cable management guide is presented as being circular in cross section and cylindrical along its length. It is understood that cable management guide in general, can have any cross section profile (oval, hexagonal, rectangular, etc.) and any profile along its length (helical, tapered/conical, etc.).

FIG. 4 illustrates a generic example of an articulating mechanism/joint and a method for assembly that may be used with remote access tools that requires a steerable end-effector joint. As mentioned above, the articulating mechanism may be useful for a variety of purposes, some of which may include minimally invasive surgical tools for laparoscopy or endoscopy. In FIGS. 4A and 4B, each set of gimbal 403 and the two gimbal guides 401 that it interfaces with constitutes a universal joint, with two rotational degrees of rotational freedom (pitch and yaw). This set provides two orthogonal axes of rotation (pitch axis and yaw axis, or X and Y) which intersect and therefore occur in the same plane. Additionally, this universal joint arrangement constrains one rotational degree of freedom (roll rotation) about the remaining axis (Z) between the two guides. By geometrically constraining this rotation (about Z), it is possible to transmit torque between the two guides propagating the torque transmission through the multi-cluster joint.

Note that, as used herein, the terms "guide", "gimbal-guide", "gimbal-guide", and "link" may be used interchangeably.

The multi-cluster joints described herein may include at least one gimbal and two gimbal guides (e.g., 2 half-gimbal guides), but in general may include an alternating sequence of guides and gimbals. Furthermore, typically there will be one more guide (half-gimbal guide) than gimbal, because the joint starts with a gimbal guide and ends with a gimbal guide, with a gimbal alternating between two consecutive guides. For example, FIG. 4A shows a guide-gimbal-guide-gimbal-guide arrangement (i.e., three guides and two gimbals). FIG. 4C shows a guide-gimbal-guide-gimbal-guide-gimbal-guide-gimbal-guide arrangement (i.e., five gimbal guides and four gimbals). Large number of gimbals and guides in this serial chain may ensure a large angle of articulation for the overall articulating joint, however fewer clusters (where each cluster includes a pair of half-gimbal guide and a gimbal between) may be used.

In use, the bottom or base guide/link may be integrated with the tool shaft while the end guide/link may be integrated with an end-effector, such as a jaw assembly. Note that the DoF characteristics of a two half-gimbal guides, one-gimbal assembly are inherited by a multi-guide multi-gimbal assembly (e.g. FIGS. 4A-4C). Each of these joint assemblies offer pitch and yaw rotational DoF and constrain the roll rotation DoF. Because of the latter attribute, rotation and torque about the roll axis is transmitted from the tool shaft to the end-effector jaws, via the end-effector articulating joint.

Each gimbal guide (which may be referred to herein as a guide or a whole gimbal guide) may include a pair of half-gimbal guides and may comprise at least one yoke component/feature on each of two opposite sides with two axially co-linear and concave channels whereupon two collinear mating spindles from the intermediate gimbal component rest. On one side of the gimbal this forms one axis of rotation (e.g. X or yaw axis). The subsequent guide comprises its yoke component/feature which supports the two remaining two spindles on the intermediate gimbal along an orthogonal axis relative to the orientation of the previous yoke. This forms the second axis of rotation (e.g. Y or pitch axis). Except for the bottom/first and top/last guide, all other intermediate guides have two yoke features: one on top, to interface with the gimbal on that side, and one on bottom, to interface with the gimbal on that side.

In some embodiments, each yoke may be allotted some relative rotation about the spindle axis and can be manipulated via various design features to control its degree of angulation prior to physical contact (e.g. articulation limit) between consecutive guides.

The articulating mechanism may also include a set of tension members (e.g. articulation cables) which extend through laterally offset channels (offset from a central channel or opening in which the gimbal may reside) in the guides in an orientation that is offset from the longitudinal center axis of the joint and symmetrically positioned with respect to the intersecting axes of the gimbal spindles.

In some embodiments, the tension members which extend through channels in the guides may terminate all at the same guide (top guide or end guide), which is generally fixed to the end-effector. This termination may be within the same spatial plane, or within different planes of the same guide, or may find termination at different guides within the multi-link (i.e. multi-guide) articulating joint.

In some embodiments the articulating mechanism further comprises a centrally bored hole through the longitudinal axis of the joint's multi-link members (gimbals and guides) to provide clearance for independent end-effector manipulation components (e.g. jaw opening or closing cables or flexible push/pull rods) or components that may be intended to offer altered bending stiffness, column buckling resistances, etc.

In the embodiments described above, the articulating mechanism is controlled by the user when certain tension members (articulating cables) are placed under loads either via manual or electro-mechanical manipulation. As one or multiple articulation cables are tensioned (i.e., pulled upon or actuated), the series of universal joints formed by the gimbals and guides allow for bending in the direction of the specific tension members with respect to the center longitudinal axis. Since the tension members terminate at a predetermined location within the multi-cluster system and a certain degree of angulation is known for each universal joint interface, the user can predictably articulate/manipulate the overall the articulating end-effector joint.

As mentioned, the multi-cluster joint shown in FIGS. 4A-4C is pinless, and avoids the use of pins to realize the alternating pivot joints between the multiple links/guides. Instead, gimbals with four spindles (all with axes in the same XY plane) may be employed that provide two-axis orthogonal pivoting action (i.e., universal joint action) within the same axial plane (i.e., XY plane), thereby saving considerable axial space compared to the construction of FIG. 3, for example and contributing to a smoothness of articulation due to the uniformity of the overall joint profile in every direction of articulation. The reduced axial length of the end-effector may help reduce the problems of cable slack, backlash, and the end-effector motion jerkiness. The multiple stacked links/guides in this configuration may be held together by the tension in the tension members i.e. articulation cables, as mentioned above.

This configuration may provide both rotational axes (yaw and pitch) of each universal joint within one plane, so that the overall length of the joint along its longitudinal direction (Z axis or roll axis) may be significantly reduced, resulting in a very tight bend radius during articulation as shown in FIGS. 5A-5B, 6, 8 and 9. Furthermore, this design may include parts (gimbal and half-gimbal guides) that are simple and repetitive. This design may use tension members (e.g. articulation cables) to assure axial assembly (along the Z axis) and deterministic motion/articulation, and there is a central path (opening) through the entire end-effector joint which allows incorporation of jaw open/close transmission (e.g., cable).

The performance of an multi-cluster joint such as this one (configured as an end-effector articulating joint) may have a high range of articulation, tight bend radius, may decouple between the two rotation directions, may provide minimal generation of cable slack, may be insensitive to closure force applied through the center, may have an case of fabrication and assembly, and may provide size scale-down feasibility. The gimbal based multi-cluster joints described herein may also provide an inherent decoupling between the two axes. Because of its pin-less gimbal construction, this concept offers a compact design in the axial direction. The resulting smaller axial dimension not only produces a tight bend radius, but also minimizes the cable slack generation and sensitivity to buckling.

Thus, described herein are medical devices having an articulating multi-cluster joint with a tight minimum bend radius that may be smoothly actuated. For example, a medical device having an articulating multi-cluster joint with a tight minimum bend radius that may be smoothly actuated, may include: an elongate tool shaft; an articulation input configured to drive articulation of the multi-cluster joint; an end-effector at a distal end of the elongate tool shaft; wherein the multi-cluster joint is between the tool shaft and the end-effector and includes: a plurality of joint clusters wherein each joint cluster has a joint cluster axis in a non-articulated state, and when fully articulated has the same minimum bend radius in any direction of articulation, wherein each joint cluster provides two orthogonal degrees of rotational freedom, further wherein each joint cluster includes an opening passing through the joint cluster along the joint cluster axis; an end-effector actuation transmission cable extending through the opening of each joint cluster of the multi-cluster joint; and a cable management guide routed through the openings of the joint clusters, the cable management guide configured to prevent lateral movement of the end-effector actuation transmission cable within each opening through the joint clusters while permitting the end-effector actuation transmission cable to move axially along the joint cluster axis. Here, lateral axis is defined as being orthogonal to the axial direction. Where, axial direction is defined parallel to joint cluster axis (both in non-articulated or articulated condition).

A medical device having an articulating multi-cluster joint with a tight minimum bend radius that may be smoothly actuated may include: an elongate tool shaft; an articulation input at a proximate end of the tool shaft; an end-effector at a distal end of the elongate tool shaft; wherein the multi-cluster joint is between the tool shaft and the end-effector, and includes: a plurality of joint clusters wherein each joint cluster has a joint cluster axis in a non-articulated state, and when fully articulated has the same minimum bend radius in any direction of articulation that is 1.5× or less (e.g., 1.4× or less, 1.3× or less, 1.2× or less, 1.1× or less, 1× or less, 0.95× or less, 0.9× or less, 0.85× or less, 0.8× or less, 0.75× or less, 0.7× or less, etc.) than a diameter of the multi-cluster joint, and wherein each joint cluster provides two orthogonal degrees of rotational freedom, further wherein each joint cluster includes an opening passing through the joint cluster along the joint cluster axis; an end-effector actuation transmission cable extending through the opening of each joint cluster of the multi-cluster joint; and a cable management guide routed through the openings of the joint clusters, the cable management guide configured to prevent lateral movement of the end-effector actuation transmission cable within each opening through the joint clusters while permitting the end-effector actuation transmission cable to move axially along the joint cluster axis.

As mentioned above, any of these devices may include joint clusters wherein each joint cluster has a joint cluster axis in a non-articulated state, and when fully articulated has the same minimum bend radius in any direction of articulation that is 1.5× or less (e.g., 1.4× or less, 1.3× or less, 1.2× or less, 1.1× or less, 1× or less, 0.95× or less, 0.9× or less, 0.85× or less, 0.8× or less, 0.75× or less, 0.7× or less, etc.), and particularly 1.2× or less than a diameter of the multi-cluster joint. This tight bend radius is particularly important because it provides surprising advantages compared to other configurations that are not capable of such small bend radii, particularly where the diameter of the apparatus is relatively small (e.g., less than 2 cm, less than 1.5 cm, less than 1.4 cm, less than 1.3 cm, less than 1.2 cm, less than 1.1 cm, less than 1.0 cm, less than 0.9 cm, less than 0.8 cm, less than 0.75 cm, less than 0.7 cm, less than 0.65 cm, less than 0.6 cm, etc.). In such cases, controlling the path taken by the inner cable (e.g., held within the opening through the center of the multi-cluster joint) is surprisingly important for smooth actuation of the apparatus. As described herein, this control may be provided in at least two ways. First, when two or more cables are present and in tension in the central channel, they may be wrapped around each other 270 degrees or more (e.g., 300 degrees or more, 330 degrees or more, 360 degrees or more, etc.), as described in more detail below. Alternatively, a cable management guide may be provided that limits (e.g., eliminates all but a nominal amount of) the lateral freedom on the cable, such as the end-effector actuation transmission cable within the central opening. For example a cable management guide may provide a channel that prevents (but for approximately a thousandth of an inch of clearance around the cable or so) lateral movement while permitting axial movement in the channel.

For example, a cable management guide may comprise a cable channel to locate the end-effector actuation transmission cable and prevent lateral movement of the end-effector actuation transmission cable within each opening through the joint clusters while permitting the end-effector actuation transmission cable to move axially along the joint cluster axis.

In general, these apparatuses may be used with a robotic (including remote robotic) system or a hand-held apparatus. For example, the articulation input may comprise a handle connected to the elongate tool shaft by an input joint.

As mentioned, each joint cluster may include: a first half-gimbal guide, a second half-gimbal guide, and a gimbal having a pair of orthogonal gimbal spindles in a cluster plane, wherein the gimbal is positioned between the first half-gimbal guide and the second half-gimbal guide.

The plurality of joint clusters may be arranged adjacently in sequence so that at least one of the first half gimbal guide and a second half gimbal guide of each joint cluster is rigidly coupled to, or formed integrally with, a half gimbal guide of an adjacent joint cluster to form a full gimbal guide. For example, each half-gimbal of the full gimbal guide may comprises a pair of yokes configured to hold a pair of gimbal spindles, further wherein the pair of yokes on the half-gimbal guide on a first side of the full-gimbal guide are arranged in parallel to the pair of yokes on an opposite side of the full gimbal guide. Each half-gimbal of the full gimbal guide may comprise a pair of yokes configured to hold a pair of gimbal spindles, further wherein the pair of yokes on the half-gimbal guide on a first side of the full-gimbal guide are arranged in orthogonal to the pair of yokes on an opposite side of the full gimbal guide.

In any of these apparatuses, the cable management guide may be secured to at least one of: one or more of the plurality of joint clusters, the end-effector, and the tool shaft to prevent rotation of the cable management guide about any of the joint cluster axes. The cable management guide may be secured by one or more of: an adhesive or a mechanical keying, or a press-fit between an outer surface of the cable management guide and one or more of the joint clusters, end-effector or tool shaft.

Each joint cluster may provide two orthogonal degrees of rotational freedom in a cluster plane. Any of these devices may include a second (or more) end-effector actuation transmission cable extending through the opening of each joint cluster of the multi-cluster joint. The end-effector actuation transmission cable may be a flexible cable that is highly compliant in bending, compression, and torsion.

Any of the apparatuses described herein may also include a set of articulation cables extending from the articulation input parallel to a neutral axis of the multi-cluster joint and positioned laterally outside of the openings of the joint clusters and configured to articulate the multi-cluster joint. An input (such as an input joint encoding pitch and yaw) may be included as part of the apparatus, and may drive actuation using these articulation cables. The neutral axis of the multi-cluster articulation joint coincides with the longitudinal axis of the joint in its unarticulated or nominal condition. Upon articulation, the neutral axis still runs through the center of the articulated joint and join members; it takes the bent or curved shape of the articulated joint. The bend radius of the joint is the average radius of curvature of this bent/curved neutral axis.

Any of these apparatuses may include joint cluster having a limit of articulation that is axi-symmetric relative to each respective joint cluster axis, so that each joint cluster provides a uniform articulated sweep and articulated roll.

As mentioned, the multi-cluster joint may be formed by stacking a plurality of gimbals and gimbal guides. For example, a multi-cluster joint as described herein may include a plurality of gimbal guides and a plurality of gimbals, wherein the multi-cluster joint is assembled by adjacently stacking a gimbal of the plurality of gimbals between a pair of gimbal guides of the plurality of gimbal guides so that a plurality of gimbal spindles on each gimbal are seated in a plurality of open yokes on the adjacent gimbal guides.

In general, and of these apparatuses may include a stiffening member in the central opening region of the multi-cluster joint (central in the unarticulated configuration). In some variations the cable management guide acts to increase the stiffness of the joint, thereby reducing, avoiding or eliminating s-bending. For example, the cable management guide may have a stiffness sufficient to reduce or eliminate s-bending in compression but not so stiff as to increase the force necessary to articulate the joint substantially (e.g., the cable management guide may have a Young's modulus of greater than 0.1 GPa, e.g., greater than 0.2 GPa, between 0.1 GPa and 2 GPa, between 0.1 GPa and 1 GPa, between 0.2 GPa and 2 GPa, between 0.2 GPa and 1 GPa, etc.).

A medical device having an articulating multi-cluster joint with a tight minimum bend radius that may be smoothly actuated may include: an elongate tool shaft; an articulation input at a proximate end of the tool shaft; an end-effector at a distal end of the elongate tool shaft; wherein the multi-cluster joint is between the tool shaft and the end-effector, and includes: a plurality of joint clusters wherein each joint cluster has a joint cluster axis in a non-articulated state, and when fully articulated has the same minimum bend radius in any direction of articulation that is 1.2× or less than a diameter of the multi-cluster joint, and wherein each joint cluster provides two orthogonal degrees of rotational freedom, further wherein each joint cluster includes: a first half-gimbal guide, a second half-gimbal guide, and a gimbal having a pair of orthogonal gimbal spindles in a cluster plane, wherein the gimbal is positioned between the first half-gimbal guide and the second half-gimbal guide; a central opening passing through the joint cluster along the joint cluster axis; a pair of end-effector actuation transmission cables extending through the opening of each joint cluster of the multi-cluster joint, wherein the end-effector actuation transmission cables are compliant in bending; and a cable management guide routed through the central openings of the joint clusters, the cable management guide configured to prevent lateral movement of the end-effector actuation transmission cables within the central openings of the joint clusters while permitting the end-effector actuation transmission cable to move axially along the joint cluster axis, wherein the cable management guide is secured to least one of: one or more of the plurality of joint clusters, the end-effector, and the tool shaft to prevent rotation of the cable management guide about any of the joint cluster axes.

Also described herein are methods of articulating a multi-cluster joint at a distal end region of a medical device having an elongate tool shaft, a proximal handle coupled to the tool shaft through an input joint, and an end-effector at a distal end of the medical device, the method comprising: moving handle of the medical device in pitch and yaw relative to the tool shaft; transmitting the pitch and yaw motion of the handle through the elongate tool shaft to the multi-cluster joint to articulate the multi-cluster joint, wherein the multi-cluster joint comprises a plurality of joint clusters wherein each joint cluster has a same minimum bend radius in any direction of articulation that is 1.2× or less than a diameter of the multi-cluster joint and includes a first half-gimbal guide, a second half-gimbal guide, and a gimbal having a pair of orthogonal gimbal spindles in a cluster plane, wherein the gimbal is positioned between the first half-gimbal guide and the second half-gimbal guide; preventing jumping of an end-effector actuation transmission cable within an opening passing through the each of the joint clusters orthogonal to the cluster plane by preventing lateral movement of the end-effector actuation transmission cable within each cluster plane while permitting the end-effector actuation transmission cable to move axially perpendicular to each cluster plane using a cable management guide within the opening passing through the each of the joint clusters; minimizing joint distortion or S-bending of the multi-cluster joint by resisting independent bending of each joint cluster due to the cable management guide; and actuating the end-effector by actuating a control or button or lever on the handle that results in pulling the end-effector actuation transmission cable proximally.

Minimizing joint distortion or S-bending may attributed to the stiffness of the cable management guide, which has a Young's Modulus of greater than 0.1 GPa (e.g., greater than 0.2 GPa, between 0.2 and 2 GPa, between 0.1 and 1 Gpa, between 0.1 and 2 GPa, etc.).

Any of these methods may also include preventing rotation of the cable management guide relative to any joint cluster as the multi-cluster joint is actuated.

As mentioned, another technique for improving the smoothness of articulation of an apparatus as described herein may also include twisting the cables (within the multi-cluster joint) so that they remain twisted within the multi-cluster joint and under tension. For example, a medical device having an articulating multi-cluster joint with a tight minimum bend radius that may be smoothly actuated, the device comprising: an elongate tool shaft; an articulation input at a proximate end of the tool shaft; an end-effector at a distal end of the elongate tool shaft; wherein the multi-cluster joint is between the tool shaft and the end-effector, and includes: a plurality of joint clusters wherein each joint cluster has a joint cluster axis in a non-articulated state, and when fully articulated has the same minimum bend radius in any direction of articulation and wherein each joint cluster provides two orthogonal degrees of rotational freedom, further wherein each joint cluster includes an opening passing through the joint cluster along the joint cluster axis; a first end-effector actuation transmission cable and a second end-effector actuation transmission cable, wherein the first and second end-effector actuation transmission cables extend through the opening of each joint cluster of the multi-cluster joint, wherein the first end-effector actuation transmission cable and the second end-effector actuation transmission cable are maintained in a twisted configuration within the multi-cluster joint around each other by more than 270 degrees; an end-effector actuation control input that maintains tension on one or both of the first end-effector actuation transmission cable and the second end-effector actuation transmission cable.

In some embodiments, a medical device having an articulating multi-cluster joint with a tight minimum bend radius that may be smoothly actuated is provided. The device can include an elongate tool shaft; an articulation input configured to drive articulation of the multi-cluster joint; and an end-effector at a distal end of the elongate tool shaft. The multi-cluster joint is between the tool shaft and the end-effector and includes a plurality of joint clusters wherein each joint cluster has a joint cluster axis in a non-articulated state, and when fully articulated has the same minimum bend radius in any direction of articulation, wherein each joint cluster provides two orthogonal degrees of rotational freedom, further wherein each joint cluster includes an opening passing through the joint cluster along the joint cluster axis. The device further includes an end-effector transmission cable extending through the opening of each joint cluster of the multi-cluster joint; and a cable management guide routed through the openings of the joint clusters, the cable management guide configured to prevent lateral movement of the end-effector transmission cable within each opening through the joint clusters while permitting the end-effector transmission cable to move axially along the joint cluster axis.

In some embodiments, a medical device having an articulating multi-cluster joint with a tight minimum bend radius that may be smoothly actuated is provided. The device can include an elongate tool shaft; an articulation input at a proximate end of the tool shaft; and an end-effector at a distal end of the elongate tool shaft. The multi-cluster joint is between the tool shaft and the end-effector, and includes a plurality of joint clusters wherein each joint cluster has a joint cluster axis in a non-articulated state, and when fully articulated has the same minimum bend radius in any direction of articulation that is 1.2× or less than a diameter of the multi-cluster joint, and wherein each joint cluster provides two orthogonal degrees of rotational freedom, further wherein each joint cluster includes an opening passing through the joint cluster along the joint cluster axis. The device further includes an end-effector transmission cable extending through the opening of each joint cluster of the multi-cluster joint; and a cable management guide routed through the openings of the joint clusters, the cable management guide configured to prevent lateral movement of the end-effector transmission cable within each opening through the joint clusters while permitting the end-effector transmission cable to move axially along the joint cluster axis.

In some embodiments, the cable management guide includes a cable channel to locate the end-effector transmission cable and prevent lateral movement of the end-effector transmission cable within each opening through the joint clusters while permitting the end-effector transmission cable to move axially along the joint cluster axis.

In some embodiments, the articulation input includes a handle connected to the elongate tool shaft by an input joint.

In some embodiments, each joint cluster includes: a first half-gimbal guide, a second half-gimbal guide, and a gimbal having a first pair of collinear gimbal spindles and a second pair of collinear gimbal spindles, wherein the two pairs are orthogonal and lie in a cluster plane, further wherein the gimbal is positioned between the first half-gimbal guide and the second half-gimbal guide.

In some embodiments, the plurality of joint clusters are arranged adjacently in sequence so that at least one of the first half gimbal guide and a second half gimbal guide of each joint cluster is rigidly coupled to, or formed integrally with, a half gimbal guide of an adjacent joint cluster to form a full gimbal guide.

In some embodiments, each half-gimbal of the full gimbal guide comprises a pair of collinear yokes configured to hold one of the pairs of collinear gimbal spindles, further wherein the pair of collinear yokes on the half-gimbal guide on a first side of the full-gimbal guide are arranged in parallel to the pair of collinear yokes on an opposite side of the full gimbal guide.

In some embodiments, each half-gimbal of the full gimbal guide comprises a pair of collinear yokes configured to hold one of the pairs of collinear gimbal spindles, further wherein the pair of collinear yokes on the half-gimbal guide on a first side of the full-gimbal guide are arranged in orthogonal to the collinear pair of yokes on an opposite side of the full gimbal guide.

In some embodiments, the cable management guide is secured to at least one of: one or more of the plurality of joint clusters, the end-effector, and the tool shaft to prevent rotation of the cable management guide about any of the joint cluster axes.

In some embodiments, the cable management guide is secured by one or more of: an adhesive or a mechanical keying, or a press-fit between an outer surface of the cable management guide and one or more of the joint clusters, end effector or tool shaft.

In some embodiments, each joint cluster provides two orthogonal degrees of rotational freedom in a cluster plane.

In some embodiments, the device further includes a second end-effector transmission cable extending through the opening of each joint cluster of the multi-cluster joint.

In some embodiments, the end effector transmission cable is a flexible cable that is highly compliant in bending.

In some embodiments, the device further includes a set of articulation cables extending from the articulation input along a neutral axis of the multi-cluster joint and positioned laterally outside of the openings of the joint clusters and configured to articulate the multi-cluster joint.

In some embodiments, each joint cluster includes a limit of articulation that is axi-symmetric relative to each respective joint cluster axis, so that each joint cluster provides a uniform articulated sweep and articulated roll.

In some embodiments, the multi-cluster joint is formed by stacking a plurality of gimbals and gimbal guides.

In some embodiments, the multi-cluster joint includes a plurality of gimbal guides and a plurality of gimbals, wherein the multi-cluster joint is assembled by adjacently stacking a gimbal of the plurality of gimbals between a pair of gimbal guides of the plurality of gimbal guides so that a plurality of gimbal spindles on each gimbal are seated in a plurality of open yokes on the adjacent gimbal guides.

In some embodiments, the minimum bend radius of each joint cluster in any direction of articulation is 1× or less than the diameter of the multi-cluster joint.

In some embodiments, the minimum bend radius of each joint cluster in any direction of articulation is 0.8× or less than the diameter of the multi-cluster joint.

In some embodiments, the cable management guide has a Young's modulus of greater than 0.1 GPa.

In some embodiments, a medical device having an articulating multi-cluster joint with a tight minimum bend radius that may be smoothly actuated is provided. The device includes an elongate tool shaft; an articulation input at a proximate end of the tool shaft; and an end-effector at a distal end of the elongate tool shaft. The multi-cluster joint is between the tool shaft and the end-effector, and includes a plurality of joint clusters wherein each joint cluster has a joint cluster axis in a non-articulated state, and when fully articulated has the same minimum bend radius in any direction of articulation that is 1.2× or less than a diameter of the multi-cluster joint. Each joint cluster provides two orthogonal degrees of rotational freedom. Each joint cluster includes a first half-gimbal guide, a second half-gimbal guide, and a gimbal having a first pair of collinear gimbal spindles and a second pair of collinear gimbal spindles, wherein the two pairs are orthogonal and lie in a cluster plane, further wherein the gimbal is positioned between the first half-gimbal guide and the second half-gimbal guide. The device further includes a central opening passing through the joint cluster along the joint cluster axis; a pair of end-effector transmission cables extending through the opening of each joint cluster of the multi-cluster joint, wherein the end-effector transmission cables are compliant in bending; and a cable management guide routed through the central openings of the joint clusters, the cable management guide configured to prevent lateral movement of the end-effector transmission cables within the central openings of the joint clusters while permitting the end-effector transmission cable to move axially along the joint cluster axis, wherein the cable management guide is secured to least one of: one or more of the plurality of joint clusters, the end-effector, and the tool shaft to prevent rotation of the cable management guide about any of the joint cluster axes.

In some embodiments, the cable management guide includes at least one cable channel to locate the end-effector transmission cables to prevent lateral movement of the end-effector transmission cables within each opening through the joint clusters while permitting the end-effector transmission cable to move axially along the joint cluster axis.

In some embodiments, the articulation input includes a handle connected to the elongate tool shaft by an input joint.

In some embodiments, the plurality of joint clusters are arranged adjacently in series so that at least one of the first half-gimbal guide and a second half-gimbal guide of each joint cluster is rigidly coupled to, or formed integrally with, a half gimbal guide of an adjacent joint cluster to form a full gimbal guide.

In some embodiments, each half-gimbal of the full gimbal guide includes a pair of collinear yokes configured to hold one of the pairs of collinear gimbal spindles, further wherein the pair of collinear yokes on the half-gimbal guide on a first side of the full-gimbal guide are arranged in parallel to the pair of collinear yokes on an opposite side of the full gimbal guide.

In some embodiments, each half-gimbal of the full gimbal guide includes a pair of collinear yokes configured to hold one of the pairs of collinear gimbal spindles, further wherein the pair of collinear yokes on the half-gimbal guide on a first side of the full-gimbal guide are arranged in orthogonal to the pair of collinear yokes on an opposite side of the full gimbal guide.

In some embodiments, the cable management guide is secured by one or more of: an adhesive, a mechanical keying, and a press-fit between an outer surface of the cable management guide and one or more of the joint clusters, end effector or tool shaft.

In some embodiments, the device further includes a set of articulation cables extending from the articulation input along a neutral axis of the multi-cluster joint and positioned laterally outside of the openings of the joint clusters and configured to articulate the multi-cluster joint.

In some embodiments, each joint cluster includes a limit of articulation that is axi-symmetric relative to each respective joint cluster axis so that each joint cluster provides a uniform articulated sweep and articulated roll.

In some embodiments, the multi-cluster joint is formed as a stack, wherein a plurality of gimbal spindles on each gimbal are seated in a plurality of open yokes on the adjacent gimbal guides.

In some embodiments, the minimum bend radius of each joint cluster in any direction of articulation is 1× or less than the diameter of the multi-cluster joint.

In some embodiments, the minimum bend radius of each joint cluster in any direction of articulation is 0.8× or less than the diameter of the multi-cluster joint.

In some embodiments, the cable management guide has a Young's modulus of greater than 0.1 GPa.

In some embodiments, a method of articulating a multi-cluster joint at a distal end region of a medical device having an elongate tool shaft, a proximal handle coupled to the tool shaft through an input joint, and an end effector at a distal end of the medical device is provided. The method includes moving handle of the medical device in pitch and yaw relative to the tool shaft; and transmitting the pitch and yaw motion of the handle through the elongate tool shaft to the multi-cluster joint to articulate the multi-cluster joint. The multi-cluster joint includes a plurality of joint clusters wherein each joint cluster has a same minimum bend radius in any direction of articulation that is 1.2× or less than a diameter of the multi-cluster joint and includes a first half-gimbal guide, a second half-gimbal guide, and a gimbal having a first pair of collinear gimbal spindles and a second pair of collinear gimbal spindles, wherein the two pairs are orthogonal and lie in a cluster plane, wherein the gimbal is positioned between the first half-gimbal guide and the second half-gimbal guide. The method further includes preventing jumpiness of the multi-cluster joint by preventing lateral movement of the end-effector transmission cable within each cluster plane while permitting the end-effector transmission cable to move axially perpendicular to each cluster plane using a cable management guide within the opening passing through the each of the joint clusters; preventing buckling of the multi-cluster joint by resisting bending of each joint cluster due to the cable management guide; and actuating the end effector by actuating a control or button or lever on the handle that results in pulling the end-effector transmission cable proximally.

In some embodiments, preventing buckling includes preventing buckling because of the stiffness of the cable management guide, which has a Young's Modulus of greater than 0.1 GPa.

In some embodiments, the method further includes preventing rotation of the cable management guide relative to any joint cluster as the multi-cluster joint is articulated.

In some embodiments, a medical device having an articulating multi-cluster joint with a tight minimum bend radius that may be smoothly actuated is provided. The device includes an elongate tool shaft; an articulation input at a proximate end of the tool shaft; and an end-effector at a distal end of the elongate tool shaft. The multi-cluster joint is between the tool shaft and the end-effector, and includes a plurality of joint clusters wherein each joint cluster has a joint cluster axis in a non-articulated state, and when fully articulated has the same minimum bend radius in any direction of articulation and wherein each joint cluster provides two orthogonal degrees of rotational freedom, further wherein each joint cluster includes an opening passing through the joint cluster along the joint cluster axis. The device further includes a first end-effector transmission cable and a second end-effector transmission cable, wherein the first and second end-effector transmission cables extend through the opening of each joint cluster of the multi-cluster joint, wherein the first end-effector transmission cable and the second end-effector transmission cable are maintained in a twisted configuration within the multi-cluster joint around each other by more than 270 degrees; and an end-effector actuation control input that maintains tension on one or both of the first end-effector transmission cable and the second end-effector transmission cable.

In some embodiments, the articulation input includes a handle connected to the elongate tool shaft by an input joint.

In some embodiments, each joint cluster includes: a first half-gimbal guide, a second half-gimbal guide, and a gimbal having a first pair of collinear gimbal spindles and a second pair of collinear gimbal spindles, wherein the two pairs are orthogonal and lie in a cluster plane, further wherein the gimbal is positioned between the first half-gimbal guide and the second half-gimbal guide.

In some embodiments, the plurality of joint clusters are arranged adjacently in sequence so that at least one of the first half gimbal guide and a second half gimbal guide of each joint cluster is rigidly coupled to, or formed integrally with, a half gimbal guide of an adjacent joint cluster.

In some embodiments, each joint cluster provides two orthogonal degrees of rotational freedom in a cluster plane.

In some embodiments, the first and second end effector transmission cables are flexible cables that are highly compliant in bending.

In some embodiments, the device further includes a set of articulation cables extending from the articulation input along a neutral axis of the multi-cluster joint and positioned laterally outside of the openings of the joint clusters and configured to articulate the multi-cluster joint.

In some embodiments, each joint cluster includes a limit of articulation that is axi-symmetric relative to the joint cluster axis, so that each joint cluster provides a uniform articulated sweep and articulated roll.

In some embodiments, the multi-cluster joint is formed by stacking a plurality of gimbals and gimbal guides.

In some embodiments, the multi-cluster joint includes a plurality of gimbal guides and a plurality of gimbals, wherein the multi-cluster joint is formed by adjacently stacking a gimbal of the plurality of gimbals between a pair of gimbal guides of the plurality of gimbal guides so that a plurality of gimbal spindles on each gimbal are seated in a plurality of open yokes on the adjacent gimbal guides.

In some embodiments, a minimum bend radius of each joint cluster in any direction of articulation is 1.2× or less than the diameter of the multi-cluster joint.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A shows roll rotation, pitch rotation and and yaw rotation and three translational motions; FIG. 1B shows pitch, roll and yaw axes of a multi-cluster joint.

FIG. 3 is an example of a multi-link joint having articulation cables 301 traversing a lateral portion of each link. Three cables are visible.

FIGS. 4A-4C illustrate one example of a multi-cluster joint that is configured as a pin-less gimbal and gimbal guide stack.

FIG. 5A shows a multi-cluster joint that is articulated to the right by 90 degrees, and FIG. 5B shows a section through the joint of FIG. 5A.

FIGS. 18A-18C illustrate "jumping" of a multi-link joint.

FIGS. 19A and 19B show an apparatus without (FIG. 19A) and with (FIG. 19B) a cable management guide.

DETAILED DESCRIPTION

A variety of articulating remote access tools have been described in the prior art. The articulating joints of these tools generally include one or a series of links or segments which can be controlled by one or more tension members. These particular combinations of links, segments, components and tension members can be useful for the purpose of steering an end-effector for remote access and manipulation of an instrument, specifically a laparoscopic or endoscopic surgical instrument. Since these devices utilize articulating end-effector joints that are generally tension member (e.g. articulation cables) controlled, they lend themselves to manipulation via input at a proximal region with respect to the end-effector and, for example, by way of handle manipulation with tension member transmission through an analogous joint mechanism. Generally, handle manipulation of an instrument, which can be considered manual or electromechanical (robotic), offers some degree of mapping to the end-effector when steering the articulating mechanism. The device described in, e.g., U.S. Pat. No. 8,668,702 offers a transmission ratio from end-effector motion to handle input. The ability to control this transmission ratio means that articulating end-effector mechanisms which offer large degrees of angulation may be more easily controlled by the handle operator during steering input. For example, a transmission ratio may allow for 20 degree input at the handle mechanism to drive up to 90 degrees of articulation at the end-effector joint. Beyond articulation with proximal steering input, the articulating joint is required to steer an end-effector which can take various forms depending upon the tool's specific purpose. The end-effector may include many different embodiments but is not limited to a pair of jaws, useful for manipulation of needles, suture, tissue, cautery, ligation clip application, etc., or it might be in the form of a camera for steerable laparoscopic/endoscopic visualization and/or diagnostics. For any of these uses or other embodiments, one can imagine that the articulating mechanism must be able to support an additional set of tension/compressible members, flexible insulated wires, fiber optics, hydraulics, etc. which do not contribute to the end-effector's steerability but may offer additional degrees of freedom of the tool at an end distal to the articulating end-effector joint mechanism. Aspects of the present invention should be considered viable for use in the aforementioned devices as well as other devices requiring an articulating mechanism.

Figure 1A:
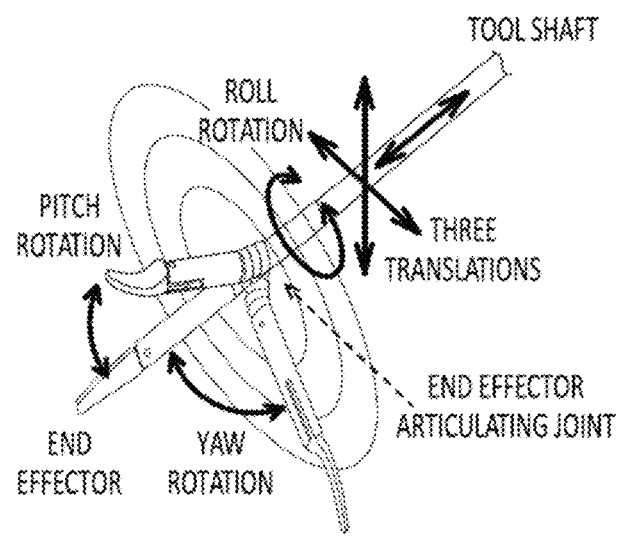
FIGS. 1A and 1B show examples of translational and rotational degrees of freedom (DoF) for an apparatus including a multi-cluster joint.
Figure 1B:
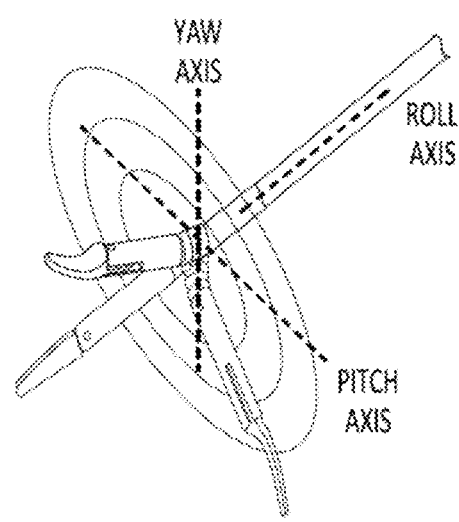
Figure 2A:
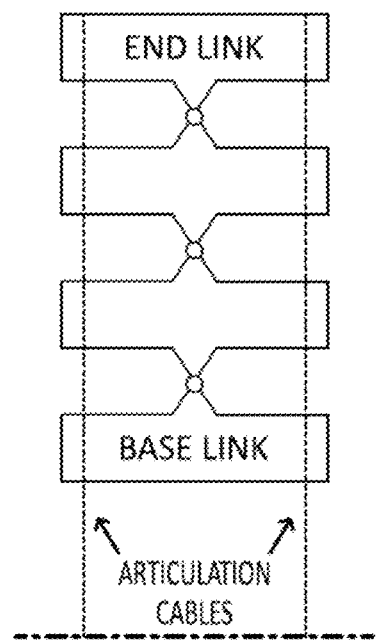
FIGS. 2A and 2B illustrate articulation (bending) of an exemplary multi-link joint having two articulation cables.
Figure 2B:
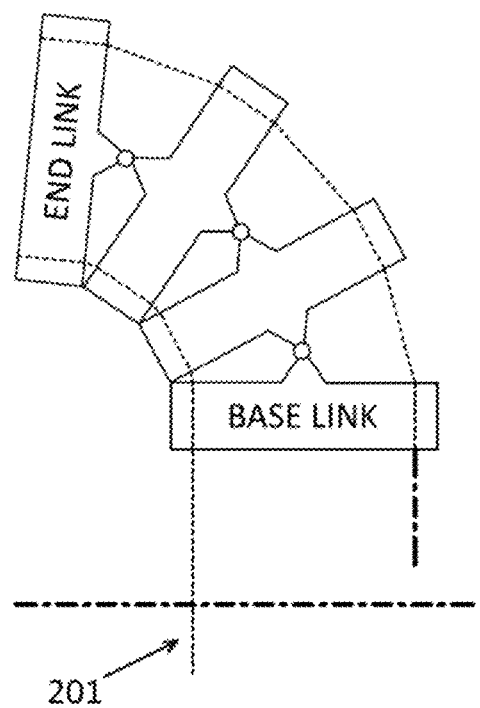
Figure 6:
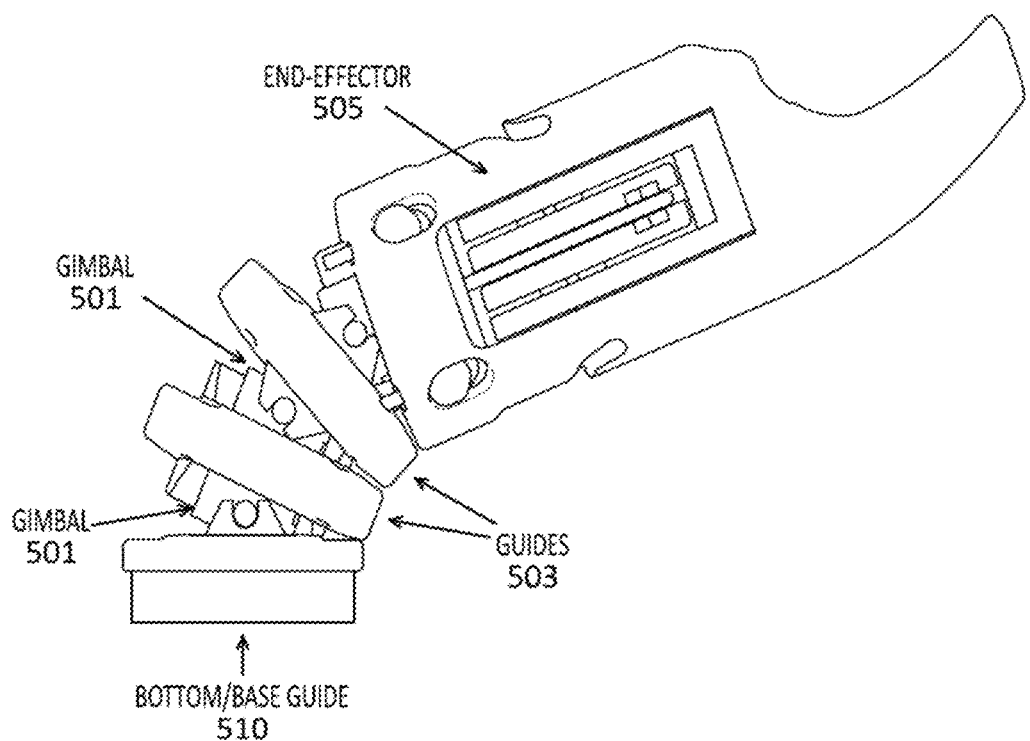
FIG. 6 illustrates one example of a distal end of an apparatus including a multi-cluster joint coupled to an end-effector (jaw assembly).
Figure 7:
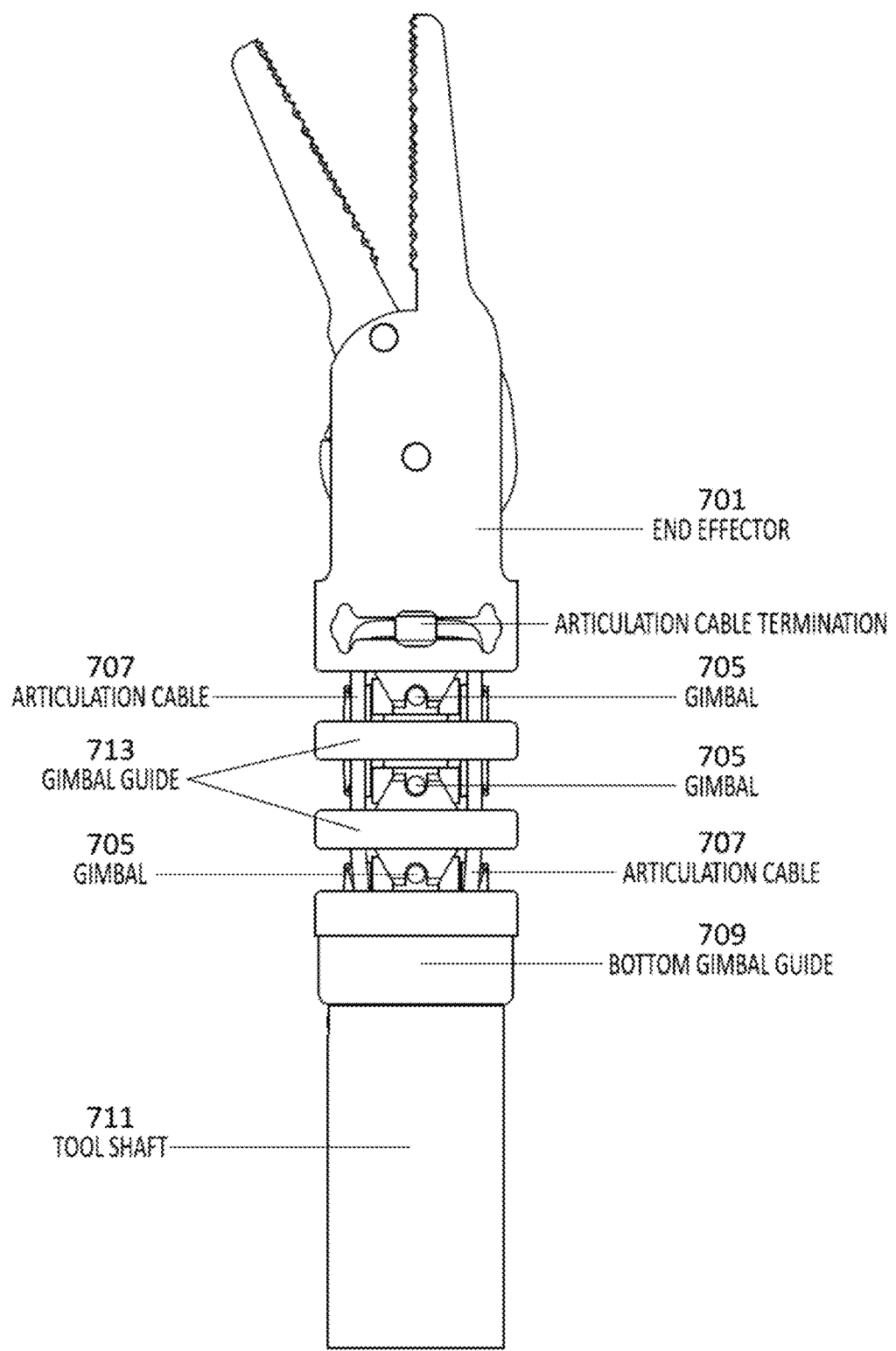
FIG. 7 is a schematic of another example of an apparatus including a multi-cluster joint with an end-effector (jaw assembly) that may be used as a medical device.
Figure 10:
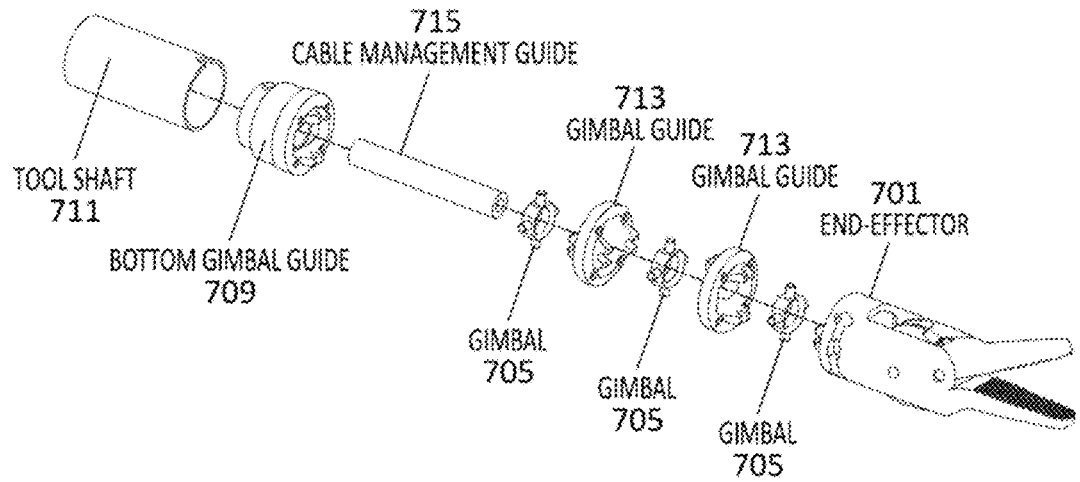
FIG. 10 shows an exploded view of the device of FIGS. 7-9.

Referring initially to FIG. 7, an embodiment of the articulating end-effector mechanism is shown, including an end-effector (jaw assembly) 701, cable termination 703, gimbal 705, cable 707, bottom of the gimbal guide 709, tool shaft 711 and gimbal guide(s) 713. In this specific embodiment the tool shaft relates to the proximal end of the device while the end-effector relates to the distal end of the device. The articulating mechanism as mentioned above comprises a multi-link joint/system containing a series of universal joints. The particular system depicted in FIG. 7 comprises three universal joints where each universal joint occurs at the interface between two gimbal guides (yoke components) about an intermediate component, a gimbal (gimbal). Each universal joint is surrounded by a plurality of cables. While only one cable appears visible in FIG. 7, each cable has a medial termination at the end-effector which constrains all axial translation of the cable and then routes through opposing channels within each gimbal guide allowing one continuous cable to behave as if it were two. In this embodiment, two cables with medial terminations are present and act as four independent tension members to steer the articulating mechanism. In a different embodiment the four cables may be all discrete with their own termination (see, e.g., FIG. 6). The cables, not shown in the exploded view of FIG. 10, maintain a slight pre-load while the end-effector joint is straight in order to apply a compressive load between components within the multi-link system keeping the axial assembly, shown in FIG. 10, axially constrained (i.e. along the Z or roll axis).

Figure 8:
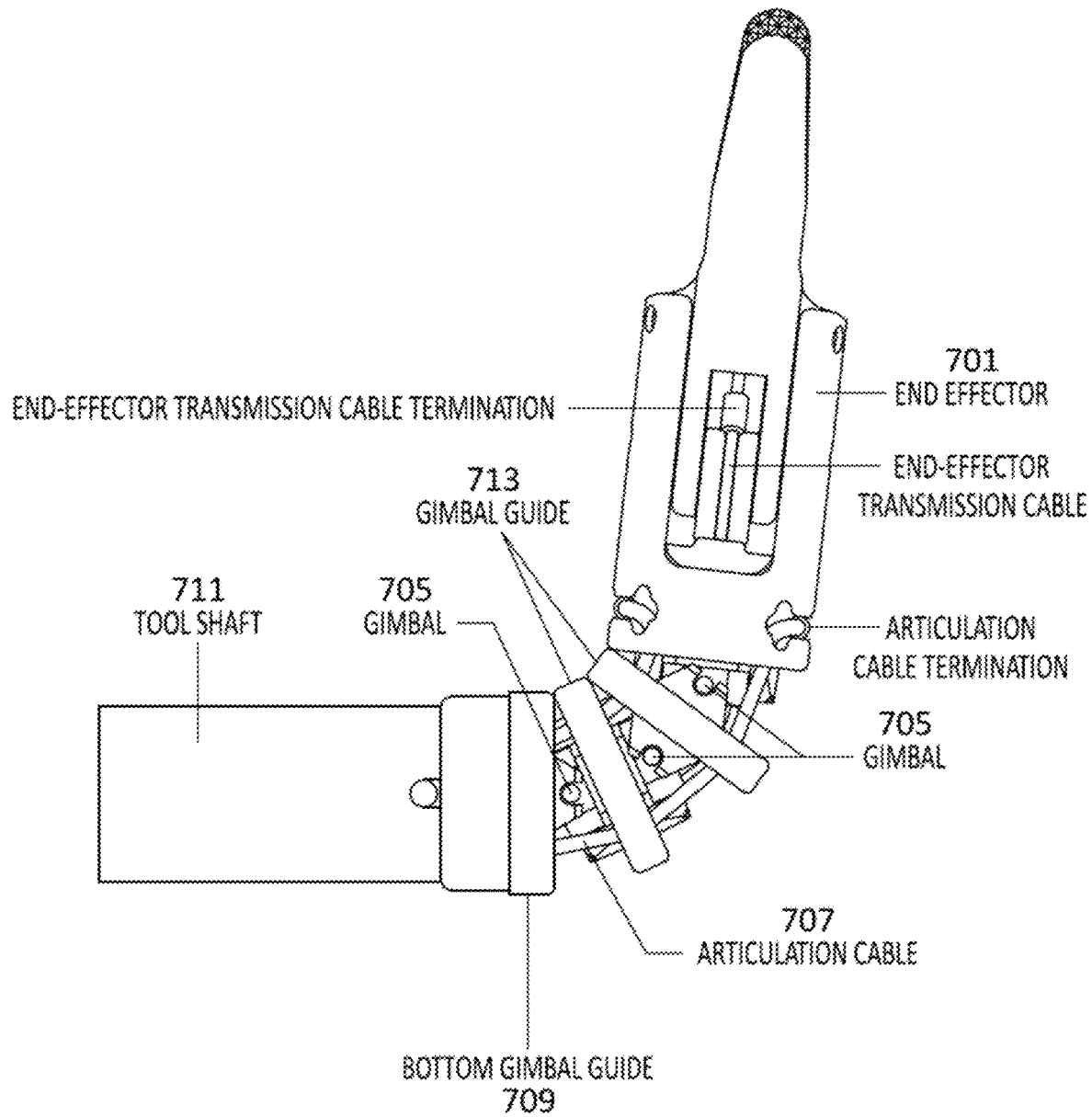
FIG. 8 show the apparatus of FIG. 7 in a fully articulated configuration at a first angle (e.g., in a 'north' direction).
Figure 9:
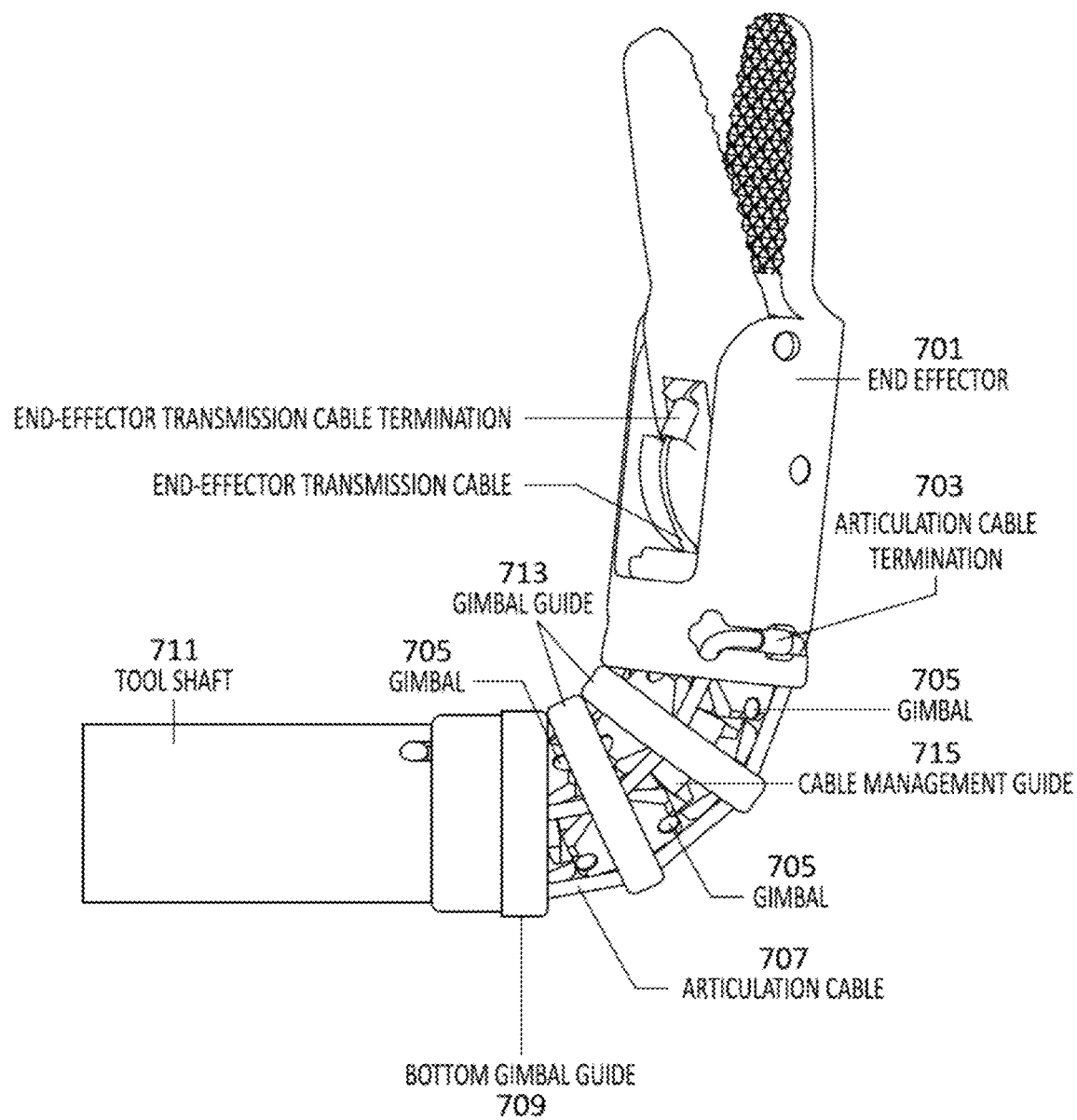
FIG. 9 is another view of the apparatus of FIG. 7 in a fully articulated configuration at a second angle (e.g., in an 'east' direction); the fully articulated configuration for any direction in this variation may have the same minimum bend radius (e.g., shown as less than 0.8× of the diameter of the multi-cluster joint).

FIGS. 7-10 are commonly labeled. In FIG. 9, a cable management guide (also referred to herein a conduit or center conduit) 715 is visible through the multi-cluster joint. One link in the system, the bottom gimbal guide is recessed or integrated or assembled into the tool shaft and offers a pair of yokes to support the first gimbal spindles. The subsequent gimbal guide would then be placed with gimbal guide yokes (see FIGS. 11A, 11B, and 11C) in an orthogonal orientation with respect to the bottom gimbal guide yokes.

Figure 11A:
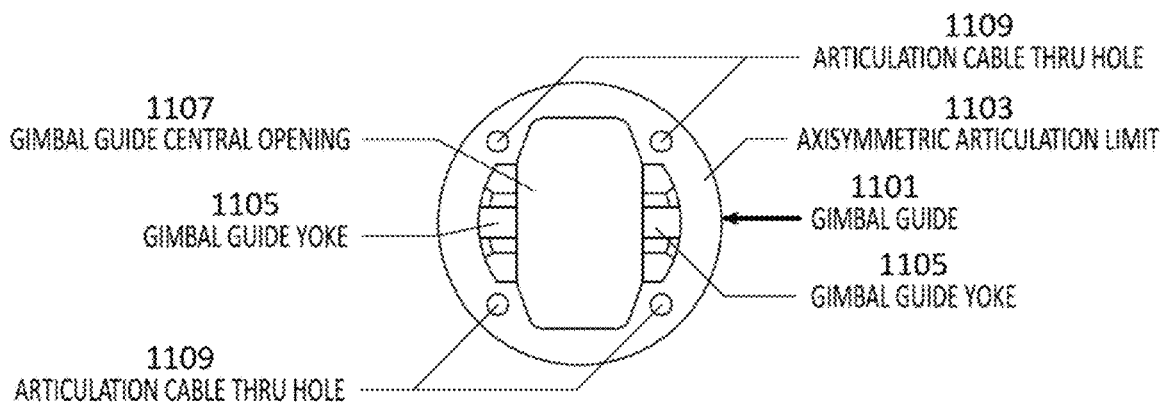
FIGS. 11A-11C shows top, left side and right side views, respectively, of a variation of a full gimbal guide having a parallel yoke arrangement.
Figure 11B:
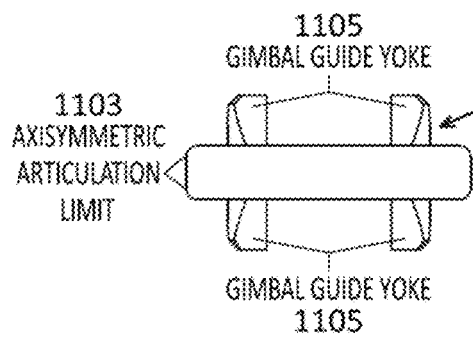
Figure 11C:
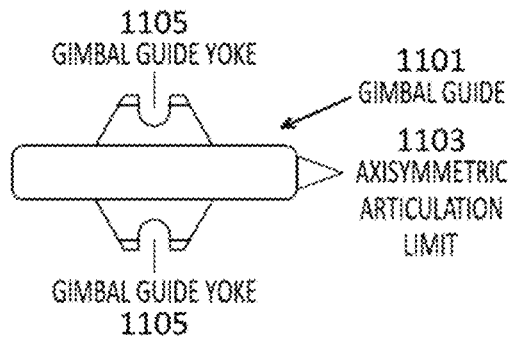
Figure 12A:
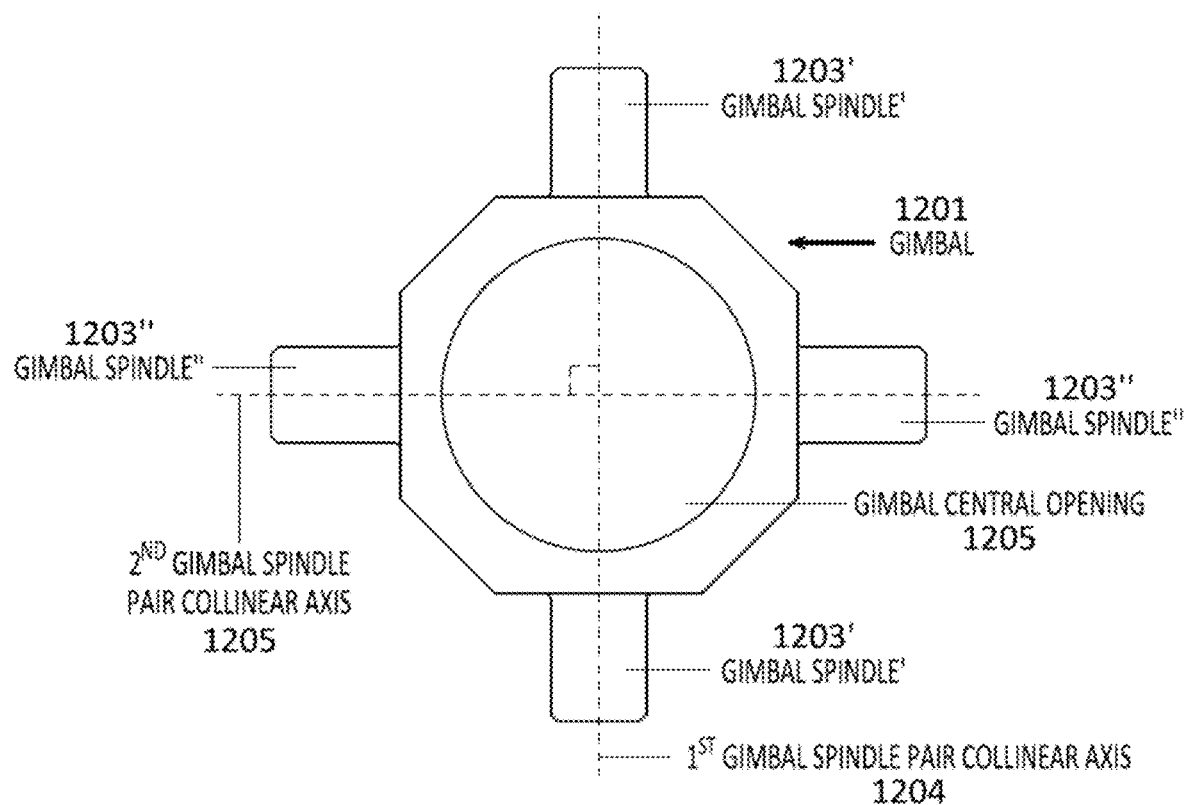
FIGS. 12A and 12B show top and side views, respectively of an example of a gimbal that may be used with any of the gimbal guides described herein.
Figure 12B:
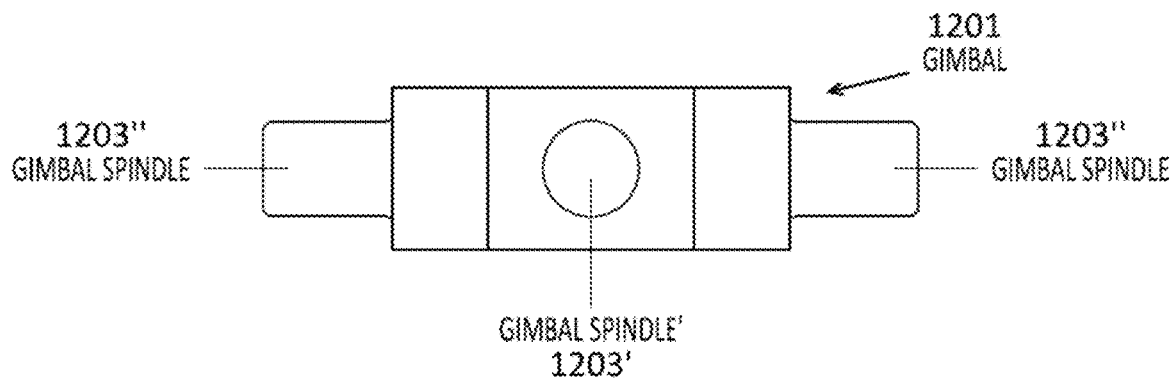

FIGS. 11A-11C illustrate views of an exemplary gimbal guide (comprising two integral half-gimbal guides 712, back-to-back), and show the gimbal guide 1101, the axisymmetric articulation limit 1103 of the gimbal guide, a pair of collinear gimbal guide yokes 1105 (collinear yokes) on each upper and lower half of the gimbal guide, a gimbal guide central opening 1107, and four articulation cable thru holes 1109. FIGS. 12A and 12B shows views of a gimbal 1201, including four gimbal spindles 1203 and a central opening through the gimbal. A pair of collinear gimbal spindles defined as 1203' are shown to be collinear with a first gimbal spindle axis 1204 and orthogonal to an adjacent pair of collinear gimbal spindles 1203" which are collinear with a second gimbal spindle axis 1205.

Figure 13A:
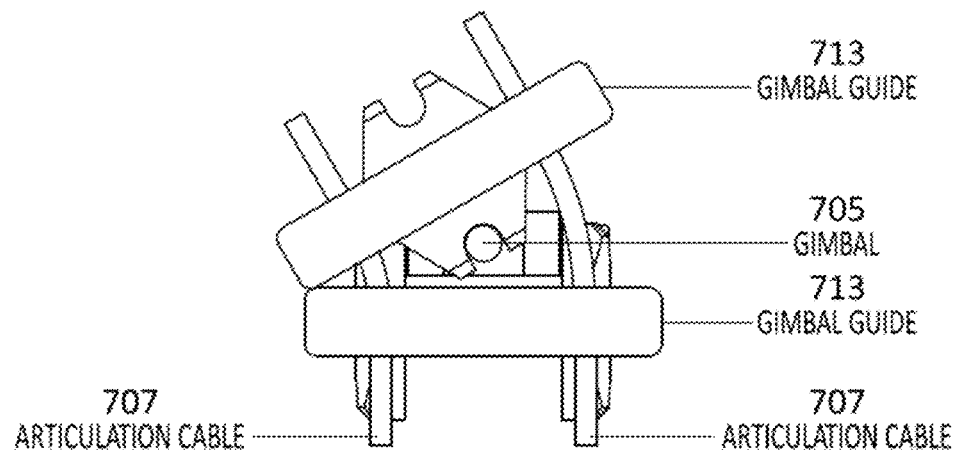
FIGS. 13A-13C show side perspective, top perspective and sectional views through a partial cluster of a multi-cluster joint.
Figure 13B:
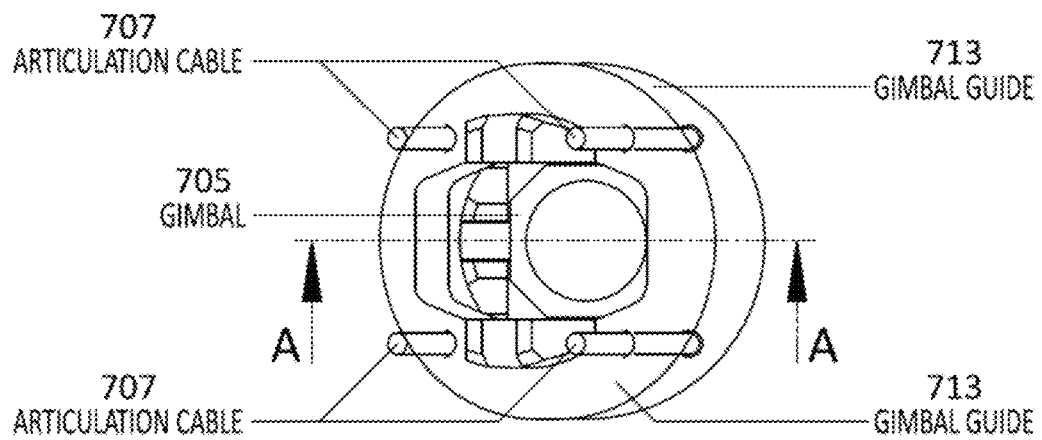
Figure 13C:
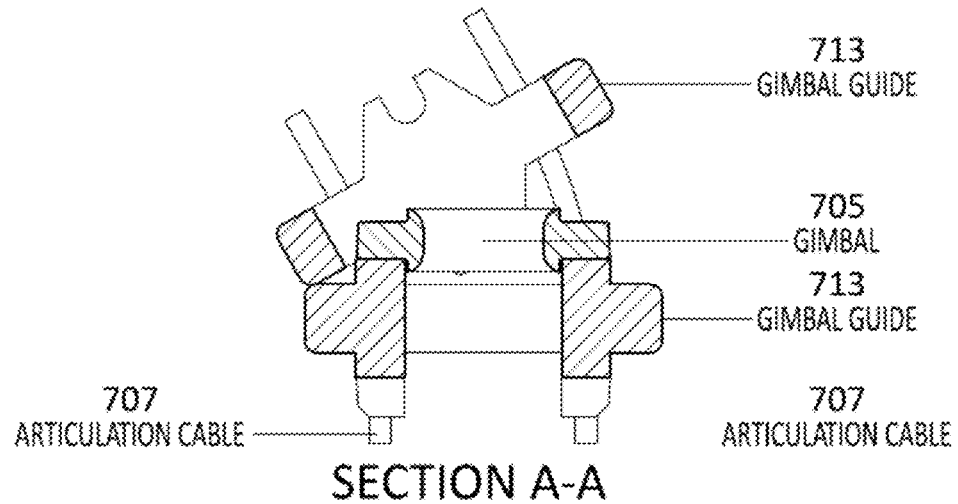
Figure 14A:
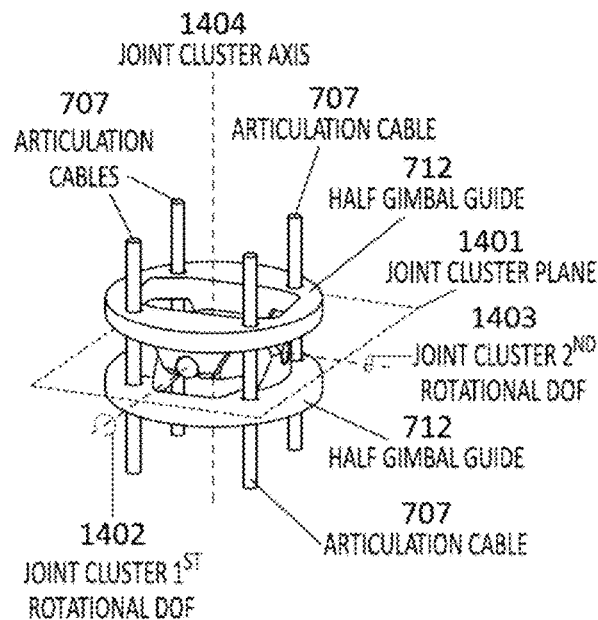
FIGS. 14A-14D show side perspective, side and sectional views through an example of a single cluster of a multi-cluster joint.
Figure 14D:
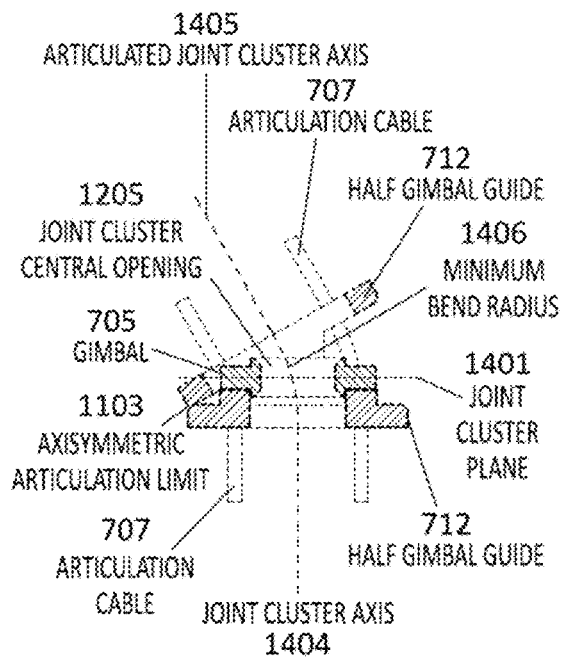
Figure 14B:
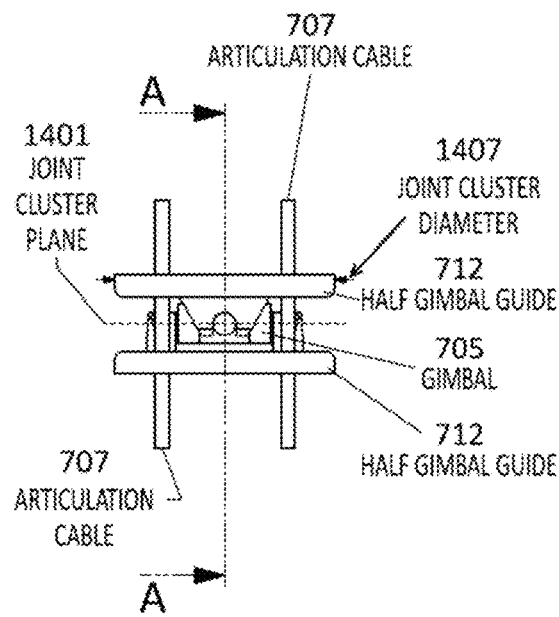
Figure 14C:
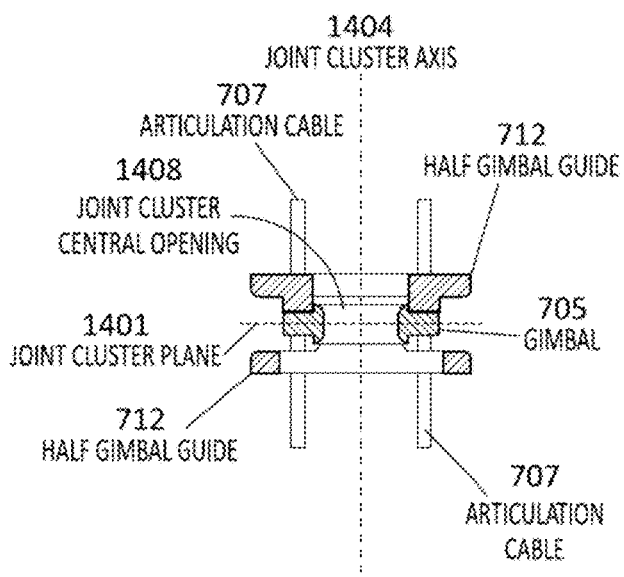

These serial links (gimbal, gimbal guides) make up the primary (proximal) universal joint of the articulating mechanism. A secondary group of links is then established in a similar manner comprising the distal gimbal guide from the primary joint which supports another pair of gimbal spindles in the vacant distal gimbal guide yokes. As before, another gimbal guide is then placed on the remaining gimbal spindles, in an orthogonal orientation with respect to the previous gimbal guide. FIGS. 13A, 13B, 13C shows a detailed view of each articulating mechanism group contained within the multi-link system. In the embodiment shown, another gimbal is applied to the vacant most distal gimbal guide yokes prior to placing the end-effector upon the remaining spindles in an orthogonal orientation with respect to the most distal gimbal guide yokes. In this embodiment, the end-effector contains an integrated set of yokes which function as the other yokes present on the gimbal guides. The end-effector, in this case, may be considered a half gimbal guide. Once the system of links is assembled, the cables can be pre-loaded to axially hold together the articulating mechanism.

Referring to FIG. 8, the articulating mechanisms have bent or articulated under the load (or tension) from two adjacent articulation cables while the two opposing cables remain slack or under a lower tension. The load from these two cables under tension causes bending of the articulating joint along one axis of rotation (e.g. yaw or pitch) as the cables slide through their specific holes (articulation cable thru holes 1109) within the gimbal guides. Similarly, the articulating mechanisms have bent or articulated under load in FIG. 9, however actuated by only one cable member while the remaining three are slackened with respect to the loaded cable. This scenario results in a compound bend along two orthogonal axes (pitch and yaw) and demonstrates how these two directions are decoupled from one another as the overall angle of articulation and bend radius of the end-effector joint is the same in both FIGS. 8 and 9.

A further example of this decoupling is the ability of this specific design to offer an articulated roll. In this motion, the articulated joint is maintained in an angled position as described above. The user then applies a rotational torque/ motion to the tool shaft axis (i.e., roll or Z axis). By way of the series of universal joints present within the articulating joint, the torque applied about the tool shaft axis is transferred along the bent/articulated end-effector axis. This function in conjunction with the features that define the hard-stops (e.g., articulation limit of articulation) in any articulated direction are typically axi-symmetric, or symmetric about a central longitudinal axis (that is defined when the joints are in the unarticulated condition) of the joint which contribute to the perception of smooth articulation via continuous articulation sweep and/or likewise, continuous articulated roll. This ability can be visualized when comparing FIGS. 8 and 9 where the direction of articulation is held constant and the joint is rotated via a torque applied to the tool shaft and rotated by 45 degrees in the counter-clockwise (CCW) rotation about the longitudinal axis of the joint as one were to look from proximal to distal down the shaft. This motion is of particular use when driving a curved suture needle along its axis of curvature and through any plane that is not normal to the tool shaft of the device as is smoothness of articulation.

Figure 15:
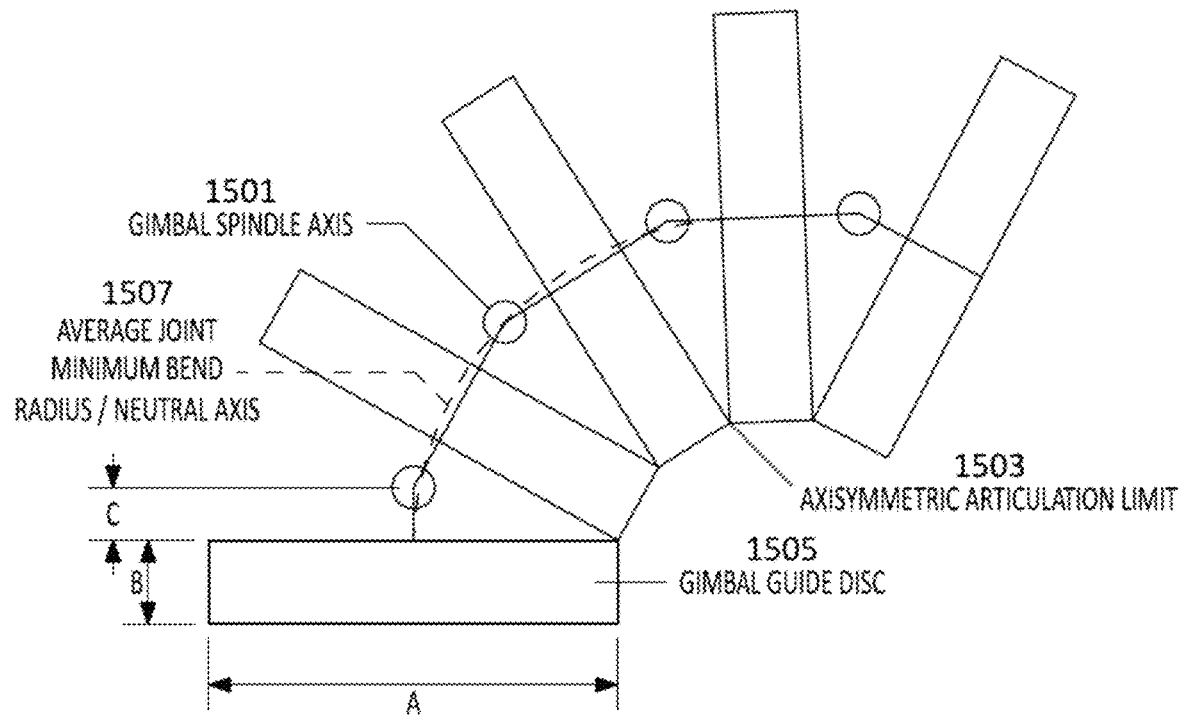
FIG. 15 is a schematic showing the bend angle of an exemplary multi-cluster joint as described herein.

Specific design of the gimbal guide enables the range of angulation that is allowed to occur between guides. As the subsequent gimbal guide is allowed to rotate about the gimbal spindle it is halted when an edge contacts the previous gimbal guide (axisymmetric articulation limits 1103) (See FIGS. 11A-11C). It is helpful that these contact edges or limits be continuous throughout the plane of contact and axi-symmetric about axis of individual gimbal guides so that maximum angulation remains the same in all directions of articulation. It should be understood that there are countless embodiments of the gimbal guide and gimbal design that could be presented with geometrical adjustments made to the yoke offset from the gimbal guide disk, the disk thickness and diameter, continuous edge radius, spindle diameter and length, etc. (see FIG. 15 for these geometric variables, showing a contacting edge where axisymmetric articulation limits have met 1503, a gimbal guide disk 1505, and a gimbal spindle axis 1507) These dimensional changes can all be implemented to alter the angulation between joints, control the overall joint length and thereby have an effect on the overall end-effector joint average minimum bend radius 1507 as well as the overall angulation. By manipulation of these variables one can achieve an end-effector joint with a tight minimum bend radius less than 1.2 times the diameter of the joint cluster.

FIGS. 14A, 14B, 14C, 14D more clearly exemplifies the "joint cluster" as it may pertain to other devices. Generally a joint cluster can be defined as the plurality of links within an articulating joint which are required to offer both Pitch and Yaw rotations. The joint cluster may then become a repeating element along the length of the articulating joint making some attachment to the adjacent joint cluster, either through geometric integration by design of individual components, welding, brazing, press-fitting, or mechanical interlocking via keyed fit, etc. One can imagine that as joint clusters are assembled, they can be assembled as repeating elements in series, or they can be alternating elements in series where the adjacent joint cluster is rotated orthogonal (90 degrees) with respect to the previous cluster. Repeating or alternating joint clusters is a concept that is typically utilized to address "constant velocity" algorithms for "robotic systems", overall joint length, joint bend radius, joint aesthetics required for "natural" wrist-like motion, and tortuous or distorted paths for tension or transmission members within the joint. In this case, a gimbal component is supported between two gimbal guide components also shown in FIGS. 13A, 13B, 13C. The joint cluster presented here represents a universal joint sometimes termed a "Cardan Joint" where typically a pair of yokes in an orthogonal orientation support and receive a pivot pin from the internal gimbal (spider, or journal, or cross-member, or the like). Inclusion of P and Y within the same plane due to the specific geometry of the gimbal component and adequate clearance geometry within the gimbal guide components allows for a high degree of angular deflection at each joint cluster, upwards of 30 degrees, however it can be greater or less than this value given the geometric variations one can imagine for joint cluster (See FIG. 15). The combination of P and Y to the same plane allows the physical length of each joint cluster to be minimized (previously referred to as compact) from a joint cluster where P and Y axes occur in different planes, spaced apart by some distance, while still normal to the central longitudinal axis of the joint-shown many times in the prior art. The resulting articulating joint once multiple joint clusters, three in this case, are stacked, form a joint which provides a high degree of angular deflection of almost 90 degrees, and potentially greater, with respect to the longitudinal axis of the tool shaft in both directions P and Y, and combinations thereof, with a compact overall bend radius measured through the now flexible longitudinal axis of the joint. This particular combination is ideal for laparoscopic procedures which require these characteristics in addition to a more natural wrist-like motion for the confined workspace available to the user. FIGS. 14A, 14B, 14C, 14D further define that the joint cluster contains a joint cluster plane 1401 which is established in this case relative to the intersection of an axis with a first rotational DoF 1402 and an axis with a second rotational Dof 1403 each corresponding to P and Y rotations of the joint cluster. The joint cluster plane is then intersected by the joint cluster axis 1404 which is consistently normal to the cluster plane and may be considered collinear to the central longitudinal axis of the joint cluster and overall multi-cluster joint. In some embodiments the joint cluster plane need not intersect these two axes but occur parallel to them and half way between their axial offset with respect to the joint cluster axis. Furthermore, FIG. 14D demonstrates the change in the joint cluster axis once articulated 1405 and the minimum bend radius achieved through the articulated joint cluster axis 1406.

As mentioned above, FIG. 15 shows various geometric variables that can be manipulated to control range of angulation, average bend radius through the neutral axis of the joint, joint length, diameter changes, etc. wherein dimension "a" on FIG. 15 can correspond to the multi-cluster joint, joint cluster diameter 1407.

Generally, geometric design changes to the articulation embodiment presented do not offer any remediation to the challenges of jumpiness (or jerkiness) and undesirable S-bending of the end-effector articulation joint. These challenges are presented when the end-effector includes a jaw, as pictured or any mechanism requiring high forces to be actuated by an additional tension member or pair of tension members. Typically these additional tension members used for jaw actuation (e.g. open/close, grasping, cutting, stapling, etc.) or other purposes are routed through a central opening hole within the gimbals 1205, gimbal guides 1107, and joint clusters 1408. The actuation force in these tension members, load the multi-cluster end-effector articulation joint in compression, leading to a buckling like situation. This buckling like situation can potentially lead to either a jumpiness in the end-effector articulation and/or S-bending of the end-effector joint, both of which potentially impact smoothness of articulation. To prevent jumpiness and S-bending and ensure smoothness of articulation at the end-effector, a cable management guide is installed (see FIG. 10) and spans the length of the entire joint with some length of overlap between the bottom guide (in the tool shaft) and the end-effector. The center conduit is a semi-rigid (i.e. flexible) body that offers bending resistance and inhibits joint distortion or S-bending when compressive loads are applied to the end-effector articulating joint. The center conduit also acts to constrain internally routed cables and prevent lateral movement of the cables from side to side, which mitigates the jumpiness.

Figure 16A:
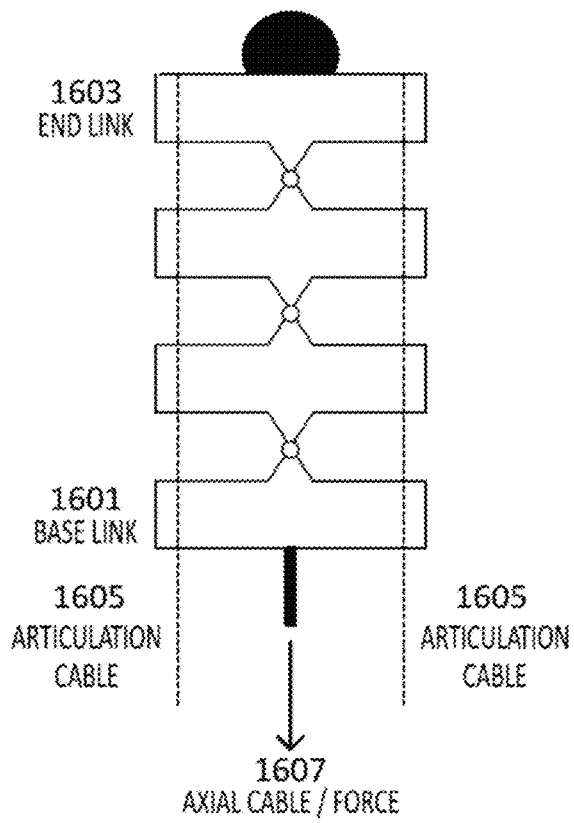
FIGS. 16A and 16B show an exemplary schematic of any multi-link articulating end-effector joint under compression.
Figure 16B:
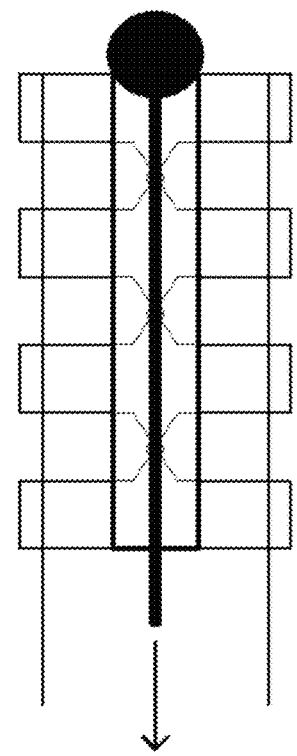

Referring to FIGS. 16A and 16B, we show a simple schematic of any multi-link articulating end-effector joint, showing a base link 1601 and end link 1603, articulation cables 1605 and an axial force 1607. This includes the prior art design of FIG. 3 as well as the proposed design of FIGS. 6, 7, 8, and 9. Here the joint is shown only in one plane of articulation and therefore only set of gimbal/pivot axes are visible. The left side shows a regular view while the right side shows a sectional view, revealing the central opening along the longitudinal (i.e. Z or roll) axis of the end-effector joint. Here the joint is shown with a central/axial/longitudinal transmission member such as a cable that is routed through the center of the articulating joint. Such as a transmission member may be used to actuate (e.g. open/close) end-effector jaws. A tension on this transmission member (e.g. cable) results in a compressive load on the end-effector joint. The joint then behaves as a column under buckling load. This leads to the possibility of the end-effector joint taking an S-shape or zig-zag shape due to the under-constraint associated with the multiple pivot/universal joints shown in FIG. 17.

Figure 17:
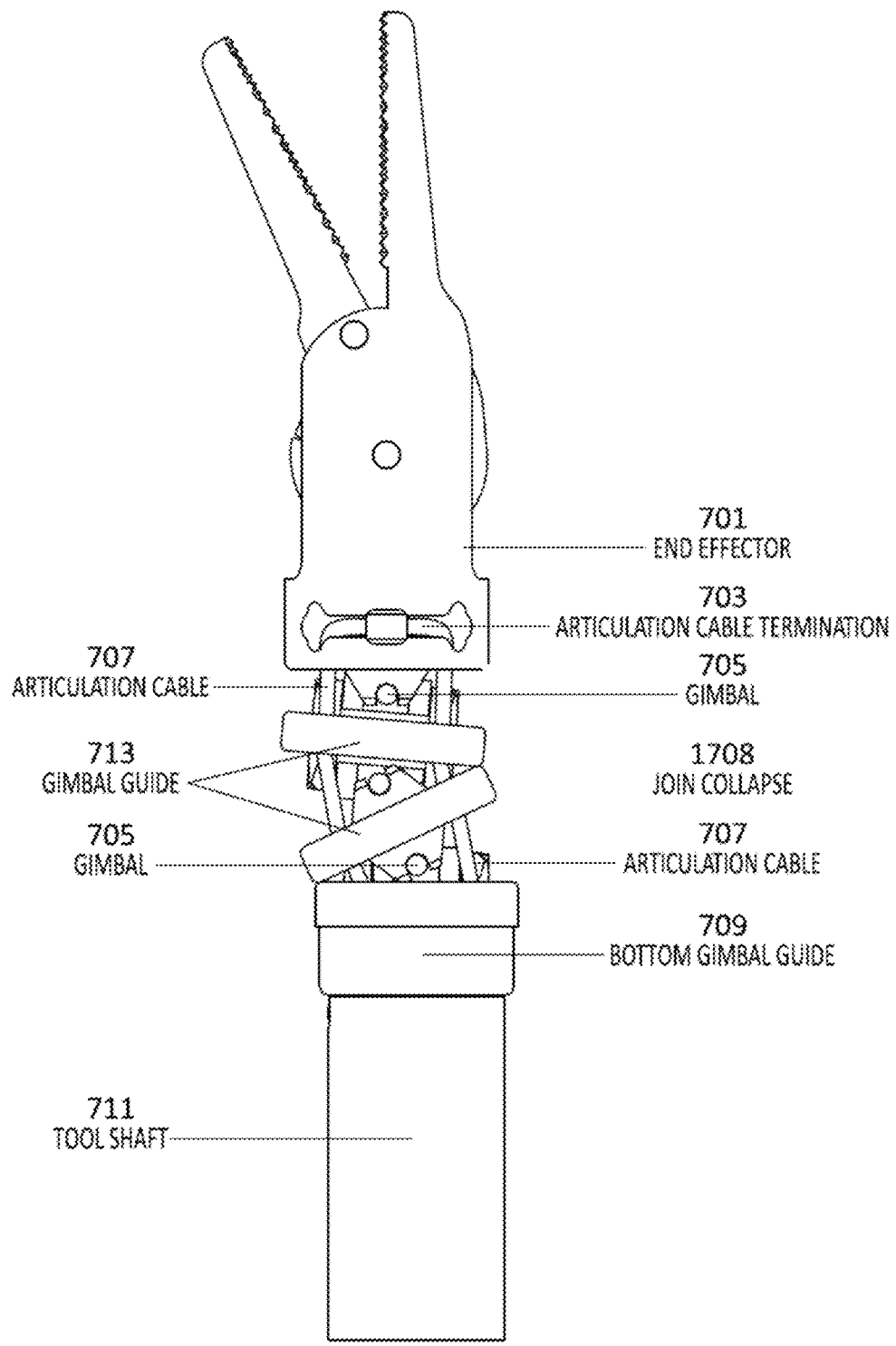
FIG. 17 is an example of s-bending of a joint.

Referring to FIG. 17, one can visualize the S-bending that occurs which appears as a lateral shift in the column occurring at the site of joint collapse or distortion 1708. Unless some spring-like feature which offers an adequate bending stiffness and/or resistance to shear in the plane normal to the longitudinal axis of the joint is utilized, S-bending (parallelogramming, shift, collapse, zig-zag, buckling) is likely to occur.

An internally routed helical spring for routing end-effector actuation transmission cables is presented in prior art however the functional failure of a spring (tension or compression) to prevent the S-bending mechanism occurs due to the spring's ability to shift laterally through regions of a joint where it is not adequately supported radially to prevent this shift. The cable management guide in the embodiments presented shown in FIG. 4 and later in FIG. 12 address this particular issue.

A further and separate outcome of this buckling behavior is shown in FIGS. 18A-18C. As the end-effector joint is articulated from left bent to a right bent in a plane of articulation, the end-effector joint's internal cylindrical cavity deforms from a left bent configuration (FIG. 18A) to nominal straight configuration (FIG. 18B) to a right bent configuration (FIG. 18C). As this happens the axial cable moves or jumps laterally from riding the left wall of the end-effector joint's internal cylindrical cavity to the right wall of the end-effector joint's internal cylindrical cavity. Since the cable is under tension and is elastic, the middle/nominal condition corresponds to the highest stretch in this cable, which corresponds to the highest potential energy in the elastic cable. This results in a top dead center effect as the end-effector joint is articulated from left to right (and vice versa) through the nominal condition, as well as from top to bottom (and vice versa) through the nominal condition. This is also referred to an "over the top" effect, and perceived by the user as jerkiness or jumpiness of the end-effector. This is effect is independent, in terms of physical origin, of the S-bending phenomenon described above.

As discussed previously, in one particular surgical tool application, the grasping force applied by the jaws has to be high to prevent the needle from slipping. Among other things, this can be achieved via a high tension in the "jaw closure cable" that connects the input lever at the tool handle to the end-effector jaws. Sec, e.g., FIGS. 19A and 19B. However, this cable has to be routed through the multi-link (or multi-cluster) end-effector joint, and therefore a large tension in this cable produces a buckling effect on the multi-link end-effector. This can potentially result in S-bending (or distortion) of the end-effector articulation, and is a consequence of the redundant local degrees of freedom associated with the multiple links and joints of the end-effector. This problem has been addressed in the past via multiple drive pulleys and cables per end-effector rotation direction, which adds considerably to the complexity, size, and cost of the overall tool design. This defeats the goal of a creating a simple, low-cost, highly functional MIS tool.

One approach to overcome this challenge is to incorporate a spring-action into the end-effector design so that the spring supports the spine or vertebrae of the multi-link joint, providing stability against buckling. While buckling is a destabilizing force, the spring provides a stabilizing force to counter it. However, it is difficult to find springs of the right size or incorporate them within the end-effector joint, given the very limited space.

Figure 20:
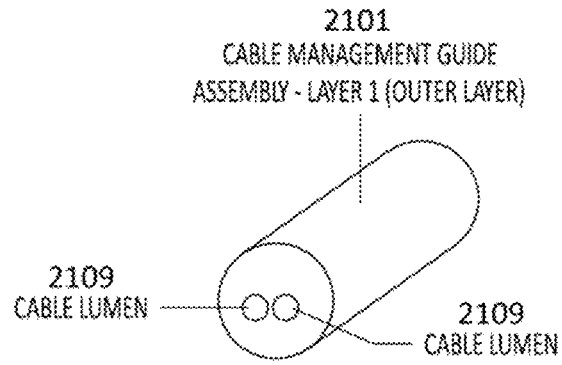
FIG. 20 shows a perspective view of one variation of a cable management guide.

As discussed previously, there is a jerkiness or jumpiness in articulation seen in multi-link end-effector, which arises due to an air-gap 1903 left between the jaw closure cable 1905 and the central opening of the gimbals that constitute the end-effector joint. To address this issue, one proposed option is to use a conduit 1901 (cable management guide) within the end-effector joint that takes up the above-mentioned air gap between the jaw closure cable and gimbals in the joint (FIG. 19B). A cable management guide with the right geometry eliminates the jerkiness in motion and with the right material properties provides the desirable spring action to mitigate S-bending (or joint distortion). Several materials can be considered for the conduit, including Nylon, Teflon, Polyetheretherketone (PEEK), polyethylene, Pebax, pellethane, and polypropylene. Teflon is a good choice because of its optimal combination of stiffness, yield strength, fatigue life, and low-friction properties. FIG. 20 shows a more explicit view of the conduit by itself. This design shows a flexible but solid cable management guide with two holes or lumens, one for the closure cable and one for the opening cable. If there is only one cable then only one lumen is needed. But the lumens keep the cable(s) constrained in the lateral (or radial) direction/plane as they route through the end-effector articulating joint. This prevents the cable from jumping from wall to wall (in the articulation joint central opening) during articulation.

Figure 21A:
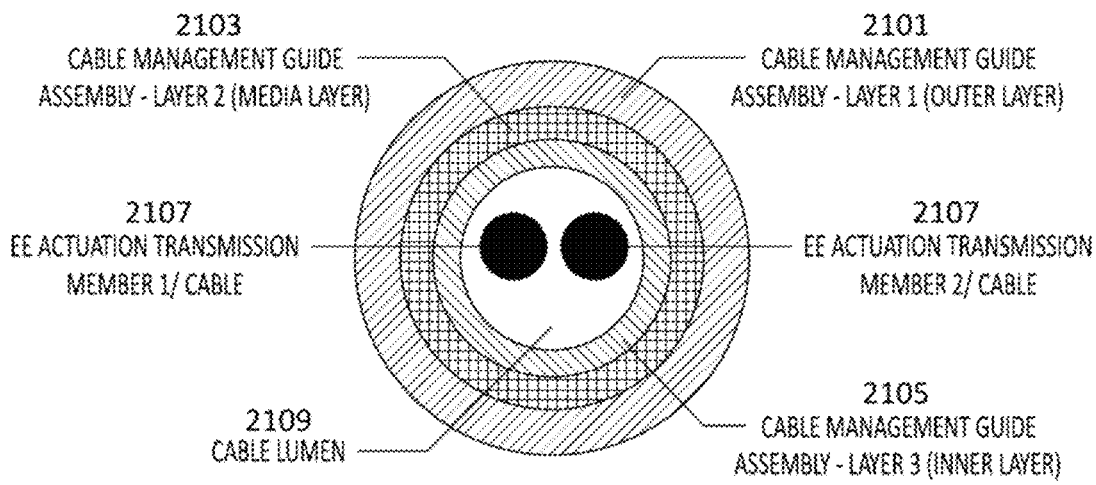
FIGS. 21A-21M show alternative sectional views through variations of cable management guides.

FIGS. 21A-21M illustrate possible examples of cable management guides (shown as cross-sections through the guide or the gimbal guide and/or a portion of a gimbal) that may prevent jumpiness and/or S-Bending or distortion of the end-effector articulation joint and/or may help in reducing articulation resistance for the end-effector articulation and translation resistance for the end-effector actuation transmission cables. Shown in FIG. 21A is a cable management guide assembly with same or different, radially stacked layers of cylindrical guide members that may be made from polymers (Nylon, Urethane, PEEK, etc.), metals and/or their braiding (Steel, Nitinol, etc.), etc. that routes or houses end-effector actuation transmission member(s). This assembly may include a layer 1/outer layer 2101, a layer 2/medial layer 2103, a layer 3/inner layer 2105, one or more end-effector actuation transmission member 2107 and a cable lumen 2109. Here, the cable management guide that goes through the central opening of the plurality of end-effector joint clusters and contain end-effector actuation transmission member(s) passing through its single lumen also articulate along with the end-effector assembly. As a result, the cable management guide assembly or individual members may have a tendency to collapse radially (or laterally) in the plane of articulation, given the one or more lumens (i.e. cylindrical holes/hollow cavities) in these members to route the actuation transmission members. The End-Effector actuation transmission member, under tension, may ride on the inner wall (i.e. small bend radius) of the cable management guide when articulated. Minimizing the lateral movement of the cables from one inner wall to another as the end-effector articulates helps mitigate the above-mentioned jumpiness. Therefore, reducing the lumen size in the conduits so that the free radial space can be reduced may help with reducing the jumpiness. Independent of this, the stiffness of cable management guide may affect the severity of S-Bending of the multi-link articulation joint. The less stiff the cable management guide is, the greater the chances of S-Bending. The S-Bending can be overcome by having different materials stacked to make the assembly such that the cable management guide's bending stiffness is maintained leading to minimal or no S-Bending altogether, while not compromising on the case of end-effector articulation. In one variation, cable management guide may be constructed by radially stacking multiple discrete or fused cylinder-shaped cable management guides with ascending values of stiffness when moving radially outwards. Another variation may involve steel braided wires that provide radial stiffness against S-Bending.

Figure 21B:
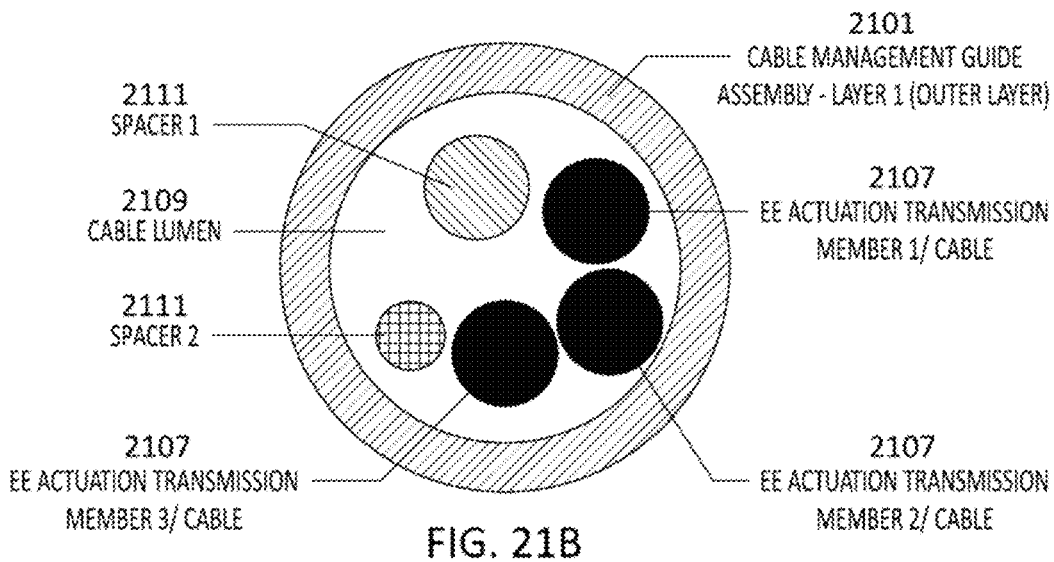

FIG. 21B presents a cable management guide assembly with an outer cylindrical cable management guide that encloses one or more spacers 2111. In the cable management guide assembly presented in FIG. 21A, a large cable lumen may lead to jumpiness. Adding spacers to the configuration shown in FIG. 21A results in the configuration of FIG. 21B, which may help mitigate the jumpiness. This addition of spacers may fill the free radial space and during articulation, it may avoid the lateral (or radial) movement of end-effector actuation transmission cable. This can help address the jumpiness problem. Separately, this may also lead to reduction in S-Bending by providing added stiffness by means of the whole cable management guide assembly. The added stiffness may have an adverse effect on articulation resistance of the end-effector if the spacers have high stiffness, and therefore spacer material, geometry, and stiffness has to be carefully chosen. These spacers may be axially located or may float inside the single lumen of the outer cylindrical cable management guide body. In one variation, multiple spacers may effectively pack the complete lumen of the outer cylindrical cable management guide body such that there exists just enough space for end-effector actuation transmission cable(s) 2107 to reside inside the cable lumen 2109 and move freely in the axial direction (along the Z, roll, or longitudinal axis). Therefore, jumpiness, S-Bending, resistance to articulation and resistance to axial motion of end-effector actuation transmission cables are inter-related areas that need to be balanced for overall functionality of the end-effector assembly.

Figure 21C:
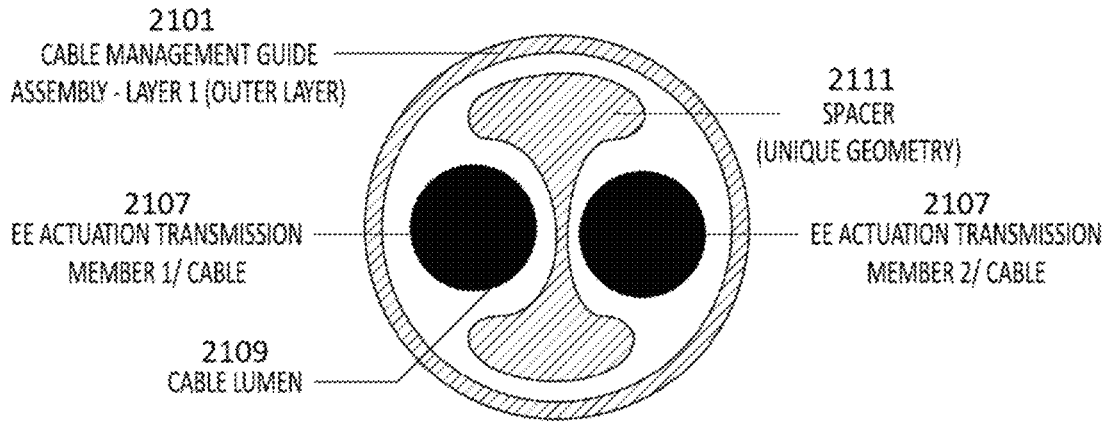
Figure 21D:
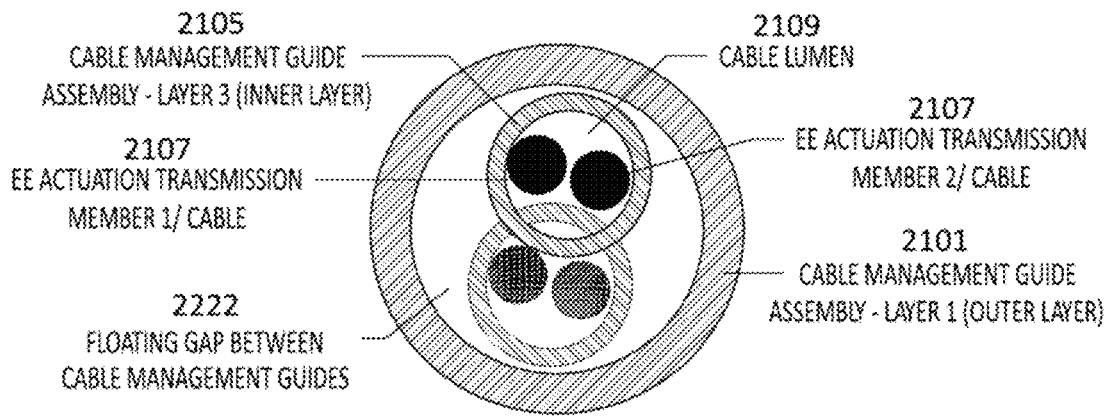

These spacers may be of any shape and/or material that help in balancing the aforementioned functionalities. FIG. 21C shows a variation where an intricately-shaped spacer 2111 is used as part of a similar cable management guide assembly. In this variation, the hourglass shaped spacer helps separate two end-effector actuation transmission cables. This separation helps in reducing the free radial space without packing the inner lumen as tightly as shown in a variation shown in FIG. 21B. This lack of very tight packing may help with reducing the resistance to motion for end-effector actuation transmission cables.

In the variation presented in FIG. 21A, the assembly is constructed using cylindrical cable management guide bodies made with same or different materials. In this variation, these bodies are either fused or press-fit together. However, in another variation shown in FIG. 21D, these bodies may be discrete and may have a small radial gap. In this variation, an inner cylindrical cable management guide body floats inside an outer cylindrical cable management guide body. There is a floating gap 2222 between inner and outer cable management guides. This variation may be helpful in achieving low articulation resistance by selecting the outer cylindrical cable management guide body to be made out of a low stiffness material. Whereas, the inner cylindrical cable management guide body can be made with a higher stiffness, harder and/or more lubricious material to provide effective axial motion for end-effector actuation transmission cables 2107. Here, the radial spacing between outer cylindrical cable management guide body and inner floating cylindrical cable management guide body can be a small air gap or be filled with grease or other viscous dampening substance that may help with jumpiness by dampening the jumping of inner cable management guide body relative to outer cable management guide body when the assembly is articulated. Also, this configuration may be suitable when the cable management guide assembly is not keyed to the end-effector joint gimbals, or to the end-effector, or to the tool shaft. In this variation, the outer cable management guide body may rotate relative to the end-effector joint during continuous articulated roll or articulation sweep of the end-effector. If the outer cable management guide body were to house the end-effector actuation transmission cable(s) 2107 directly without the inner cable management guide body, this may lead to unnecessary twisting of these end-effector actuation transmission cables and therefore, binding their axial motion (normal to the cluster plane) to transmit motion to the end-effector. Whereas, having a floating inner cable management guide body not rigidly connected to the outer cable management guide body may help avoid rotation of inner cable management guide body with outer cable management guide body while the outer cable management guide body is rotated by the plurality of gimbals in the multi-link end-effector joint.

Figures 21E, 21F:
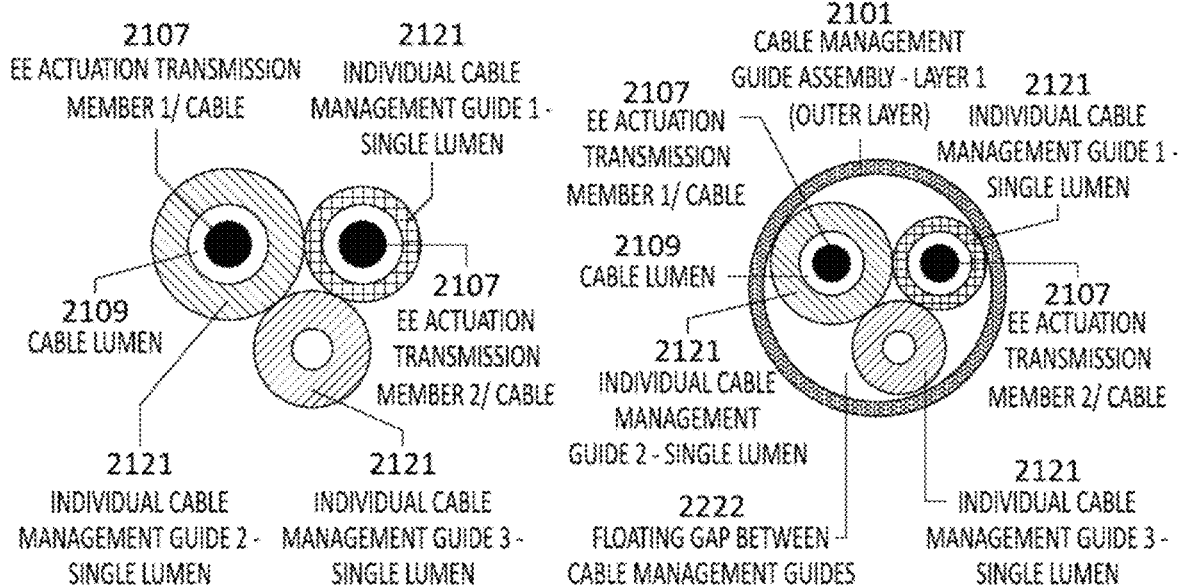
Figure 21G:
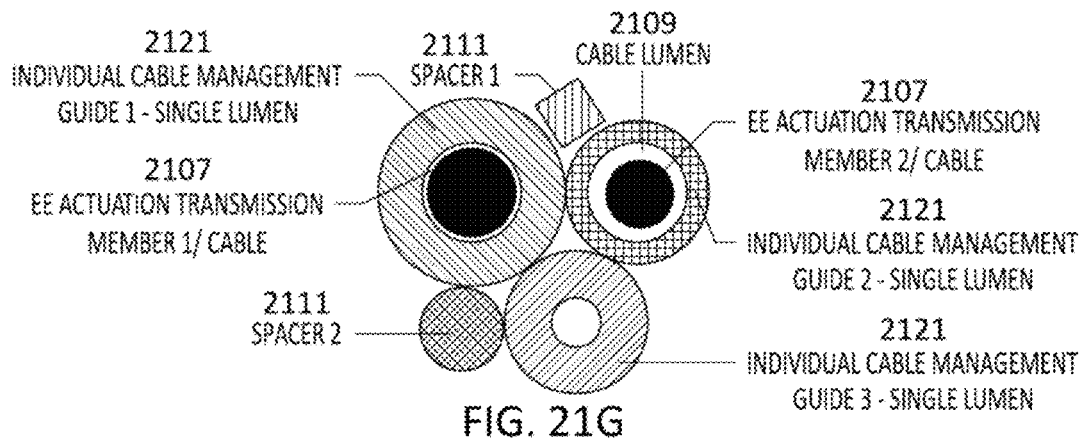
Figure 21H:
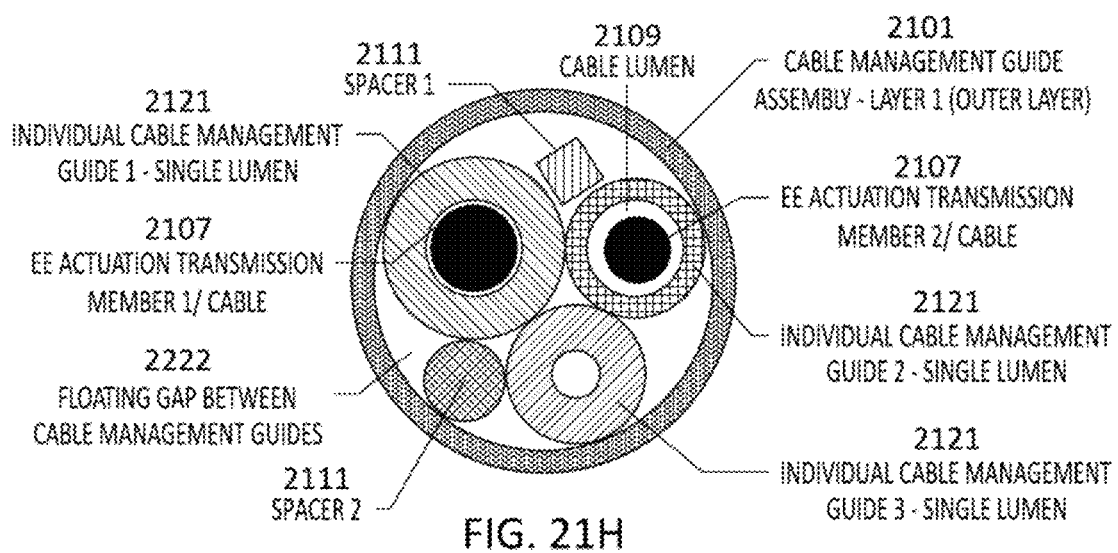

FIG. 21E shows a variation where a cable management guide assembly includes multiple cable management guide bodies stacked together axially along each other. Here, individual lumens are provided in respective individual cable management guide bodies 2121 (e.g. tubes or conduits) to allow for end-effector actuation transmission cables to pass through. This may help avoid jumpiness as an end-effector actuation transmission cable can laterally move through only the free radial space provided by the lumen size; wherein the lumen size can be small enough to restrict free radial space while providing low resistance to axial motion for end-effector actuation transmission cable. These cable management guide bodies may be routed directly through the central opening of the gimbals. Alternatively, these multiple cable management guide bodies may have an outer cable management guide body 2101 encapsulating them, as shown in FIG. 21F. FIG. 21G and FIG. 21H show a variation of the configuration shown in FIG. 21E and FIG. 21F, respectively, where one or more spacers 2111 are added to the assembly to provide stiffer assembly which may further mitigate S-Bending.

Figure 21I:
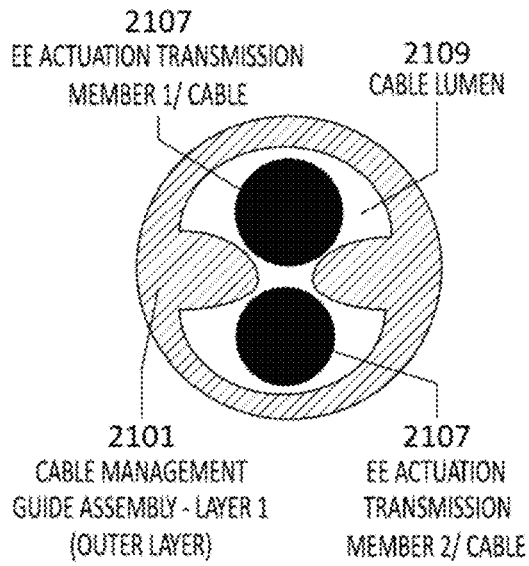
Figure 21J:
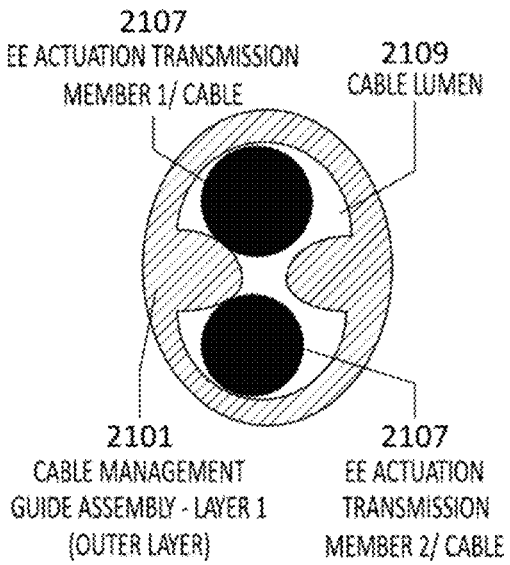
Figure 21K:
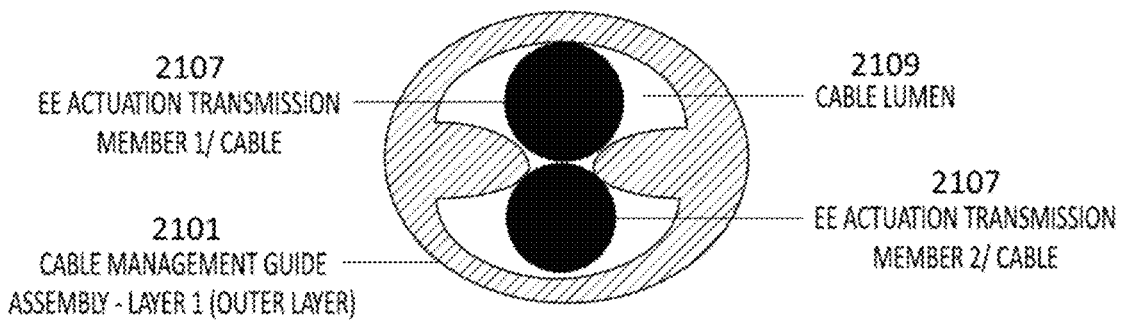

FIG. 21I through FIG. 21K show a variation which presents a custom-designed cable management guide 2101. This guide has features to separate end-effector actuation transmission cables 2107 from each other so that the resistance to axial motion of jaw closure cables can be reduced. This is combined by reduction in jumpiness by reducing the free radial space within which respective cables move during articulation. FIG. 21J shows a cross-section of a variation where the cable management guide is articulated in the horizontal plane. The cable management guide compresses in the horizontal plane and brings the notch features close together, avoiding a possibility for end-effector actuation transmission cables to come in contact or leave their respective region to move into another cable's region. FIG. 21K shows a cross-section of a variation where the cable management guide is articulated in the vertical plane. The cable management guide compresses in vertical plane. The notch feature may be designed such that still, the cables 2107 may not be able to come in contact and leave their respective regions.

Figure 21L:
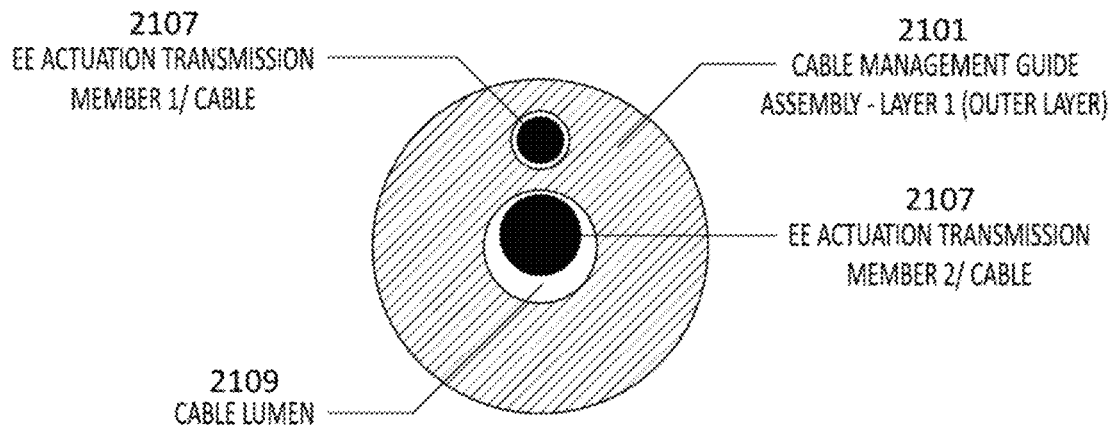
Figure 21M:
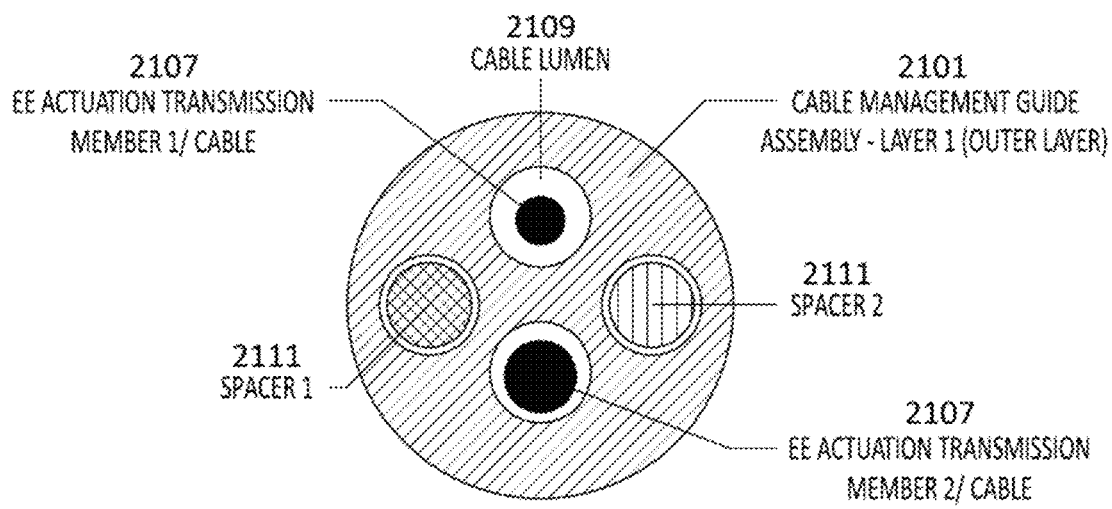

Cable management guide may have more than one lumens to avoid jumpiness as well as avoid contact between end-effector jaw closure transmission cables such that they can move/translate axially with low resistance. FIG. 21L shows a variation that presents a cable management guide that includes two lumens for two end-effector actuation transmission cables. Considering that one of the two end-effector actuation transmission cable is under considerably higher tension or is larger than the other cable, this transmission cable may have an adverse effect on the uniformity of articulation in all directions if it were to reside non-symmetrically to the center axis of the cable management guide. In FIG. 21M, a variation shows the location of cable management guide along the center axis of cable management guide. This cable may be the transmission cable with higher tension or may be the larger size transmission cable.

FIG. 21M shows a variation of a dual lumen cable management guide where multiple lumens are present in the cable management guide. One or more of these lumens may be used to route end-effector actuation transmission cable(s). These lumen may be located slightly radially off from the center axis (or the roll axis, Z axis, or longitudinal axis) of the cable management guide. Being away from the center axis of the cable management guide, these cables may impact the uniform and smooth articulation of the end-effector. To compensate for this undesired increased stiffness in the cable management guide due to presence of end-effector actuation transmission cables under tension; one or more lumen can be present in the cable management guide that act as voids to remove material along one or more planes in which the cable management guide along with cables have higher stiffness. These lumens can also act as housing for spacers, again acting as compensation members to overcome higher stiffness in certain planes. Spacers that are made of stiffer or softer material than cable management guide may help compensate variation in stiffness in certain planes.

Figure 22:
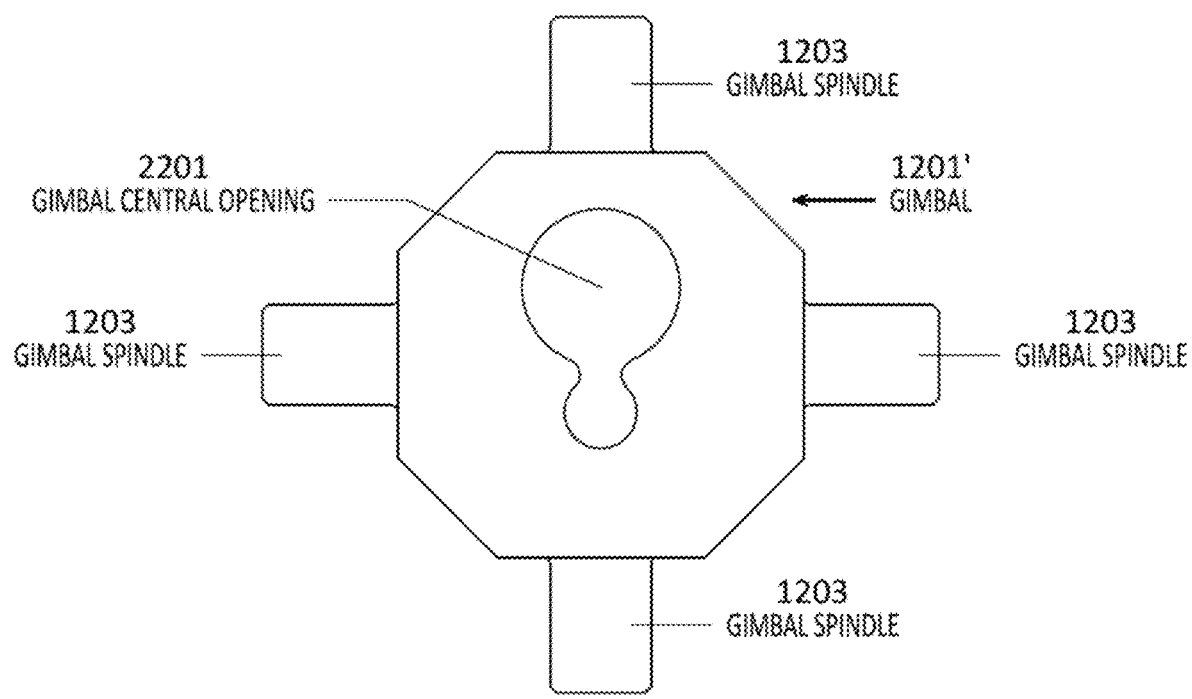
FIG. 22 shows an example of a gimbal having an integrated cable management guide.
Figure 23:
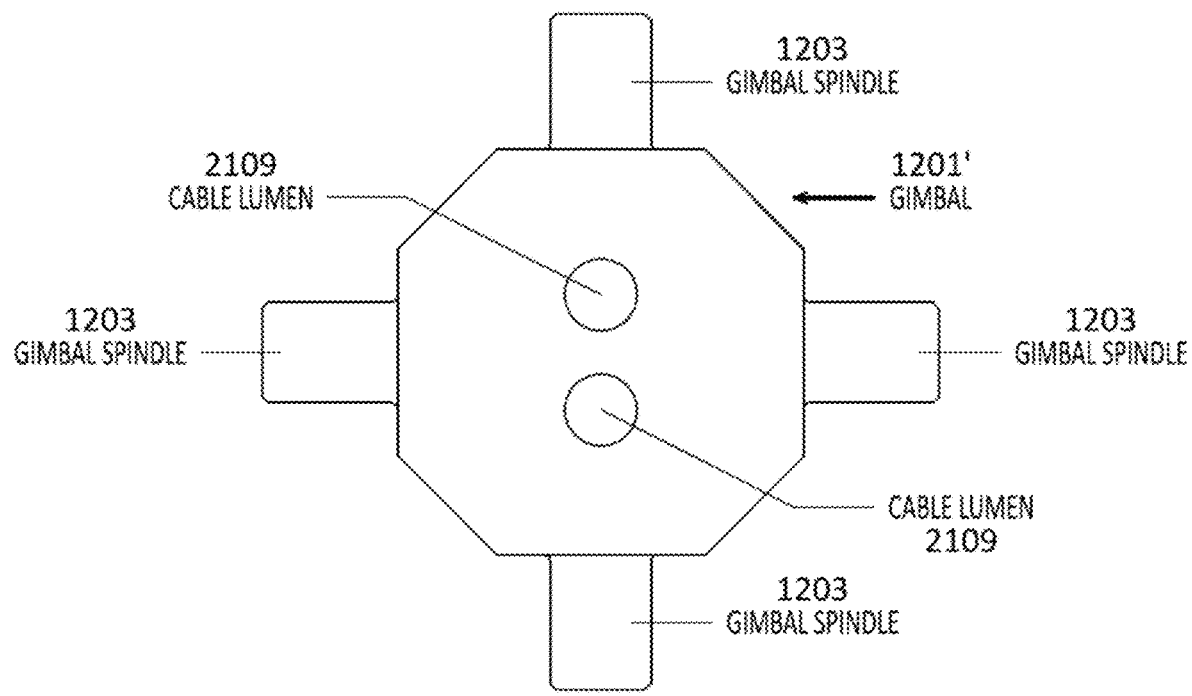
FIG. 23 is another example of a gimbal having an integrated cable management guide.

Another way to achieve radial location of the jaw actuation transmission cables (for jaw opening/closing) would be to employ a gimbal design in the articulating joint of FIGS. 6, 7, 8,9 that has a solid filling through its center except for well-defined holes (lumens) that radially (or laterally) constrain the end-effector transmission cables. See FIGS. 22 and 23 for potential geometries, showing a gimbal 1201' with gimbal spindles 1203, a cable thru hole 2109 and gimbal central opening 2201.

Figure 24:
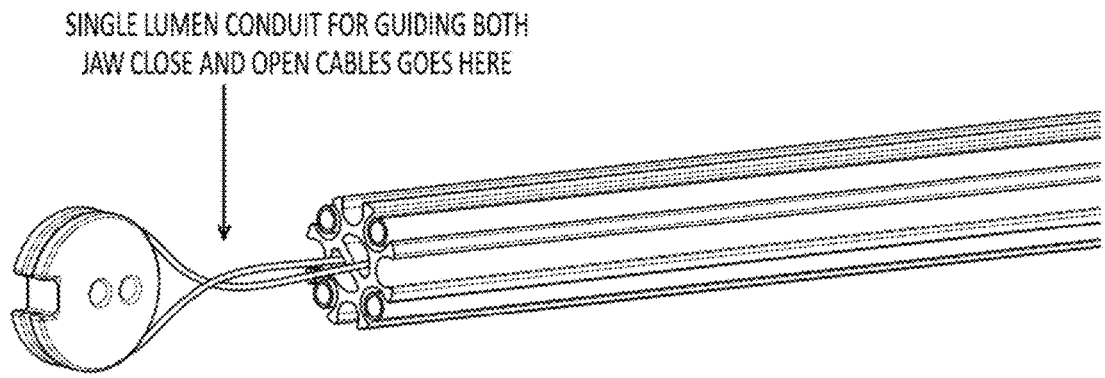
FIG. 24 is another example of cable management in which the cables are crossed within a cable management guide.

Yet another way to constrain the side to side movement (i.e. radially locate) the jaw transmission cables (for jaw open/close) is to use a single-lumen cable management guide like that shown in FIG. 21A to route both cables, but intentionally cross them through this cable management guide. This is shown in FIG. 24. Here all components of the end-effector joint are hidden. A jaw closure/open transmission pulley is shown on the left. The end-effector actuation transmission cables go through a single hole/lumen cable management guide (not shown) which placed in the central opening of the end-effector articulating joint (not shown). The cables exit into the tool shaft (not shown) on the right and enter the tool shaft (shown) on the right. Once the cables are under tension their intertwining ensures that the cables are radially (or laterally) constrained within the central opening of the end-effector articulating joint.

Figure 25:
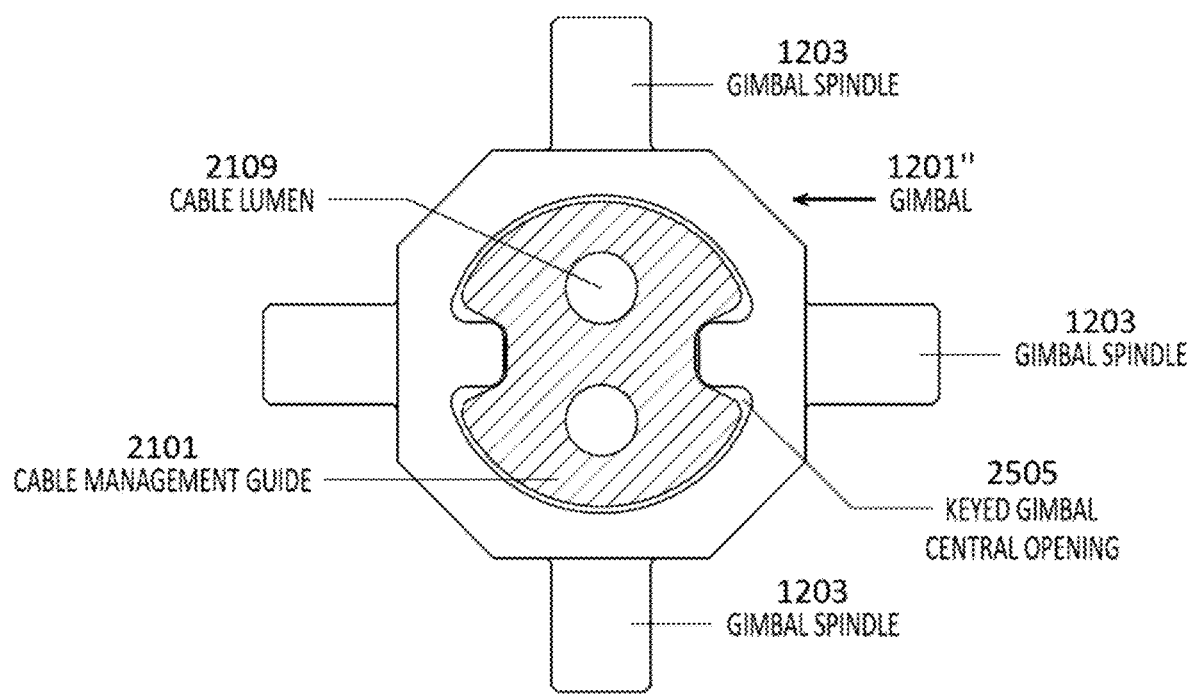
FIG. 25 shows a gimbal in which the cable management guide is keyed to prevent rotation within the opening of the multi-cluster joint.
Figure 26:
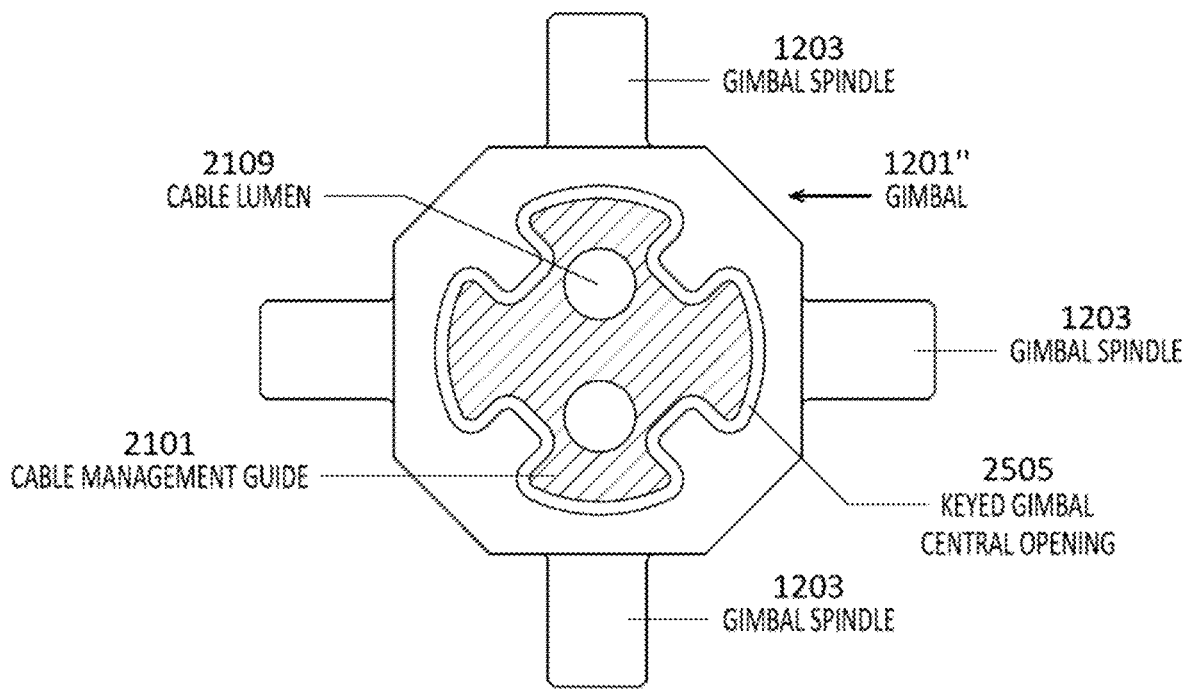
FIG. 26 is another example of a gimbal in which the cable management guide is keyed to prevent rotation within the opening of the multi-cluster joint.

One of the challenges associated with the routing of a compliant cable management guide through the central opening of an articulating joint is that this cable management guide may spin about its axis (i.e. the roll axis, Z axis, or longitudinal axis). This is especially true when the end-effector is continuously articulated in the same direction (clockwise or counter-clockwise) during an articulated sweep or articulated roll. As the gimbal components are deflected with respect to the longitudinal axis the inner diameters of the central opening of the gimbals 1205 imparts circumferential shear forces on the outer diameter of the compliant cable management guide. As the overall joint articulates from one direction to the other, performs an articulated sweep or roll motion, the gimbals continuously alter their point of contact with the conduit as they pivot thru pitch or yaw. The conduit may have a slightly smaller or compliant outer diameter with respect to the gimbal central opening inner diameter; this scenario leads to a driven rotation of the internal conduit (about the roll, Z, longitudinal axis, joint axis, joint cluster axis). This issue is of particular importance in the particular embodiment of the cable management guide shown in FIGS. 21A-21J where lumens guiding tension members do not run through the central (longitudinal) axis and instead or slightly radially offset from this axis. In this case, if the conduit itself is free to rotate about its longitudinal axis due to the above-described effect, one can imagine that jaw closure transmission cables routed through the conduit would twist upon themselves. This twisting can impart loss in function or increased resistances to the jaw closure transmission cables that are guided/routed through the conduit. Ways to mitigate this twisting of the cable management guide about its axis or the joint axis include securing the conduit (or cable management guide) to one or more of the gimbals, end-effector, or tool-shaft such that this rotation is restricted. This may be accomplished via mechanical keying features between the cable management guide and one or more of the gimbals, or the end-effector, or the tool-shaft, or all of them. These keying features could include countless embodiments and combinations thereof not limited to internal or external spline and groove geometries between the gimbal and conduit like those shown in FIGS. 25 and 26. Other methods that can address this issue include an adhesive or press-fit applied between the conduit and one or more of the gimbals, or the end-effector, or the tool-shaft, or all of them. Another method involves an overmold, through the secondary injection molding of a polymer cable management guide structure around the gimbal components or perhaps the metal injection molding of a shape memory alloy (SMA) like Nitinol. In FIGS. 25 and 26, the gimbal 1201" includes a cable management guide ("conduit") 2507 that is keyed 2505 to match the gimbal keying and includes a cable thru hole 2503. Securement to the end-effector can mean securement to a component in the end-effector assembly that is torsionally (about the roll axis) constrained in the end-effector assembly. Securement to the tool shaft can mean securement to a component in the tool shaft assembly that is torsionally (about the roll axis) constrained w.r.t to the tool shaft.

The cable management guide (or conduit) used in the end-effector joint takes a curved/convoluted shape during end-effector articulation. This can cause damage to the cable management guide or the end-effector actuation transmission cable that goes through it, as well as increase resistance to articulation or jaw open/close action. This may be reduced by some geometric variations of the gimbal guide design in the proposed articulating end-effector joint.

Figures 27A, 27B:
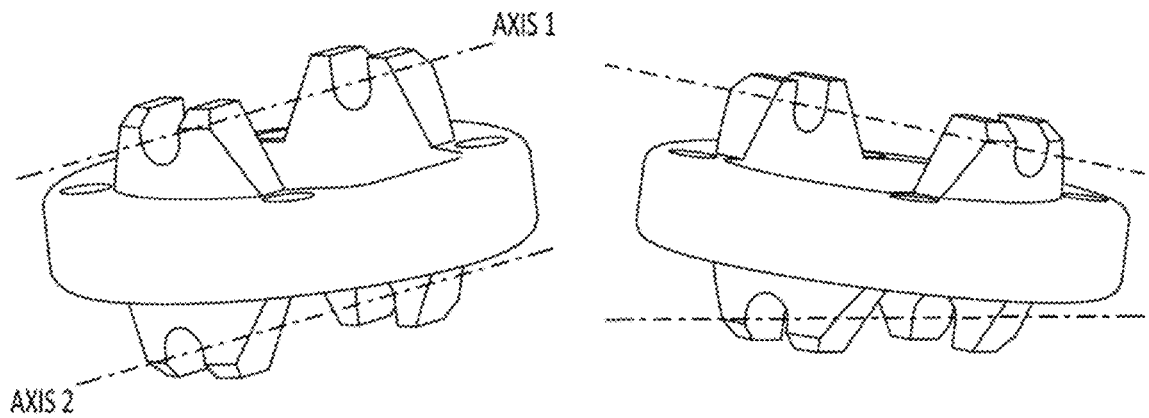
FIGS. 27A and 27B show full gimbal guides in which the yokes are parallel (FIG. 27A) and perpendicular (FIG. 27B).
Figure 28A:
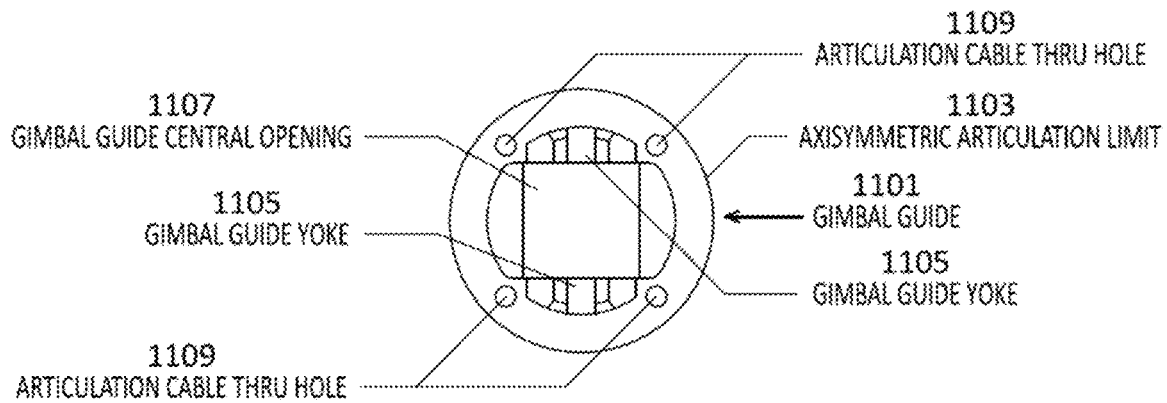
FIGS. 28A-28C show top, left side and right side views, respectively, of a full gimbal guide.
Figure 28B:
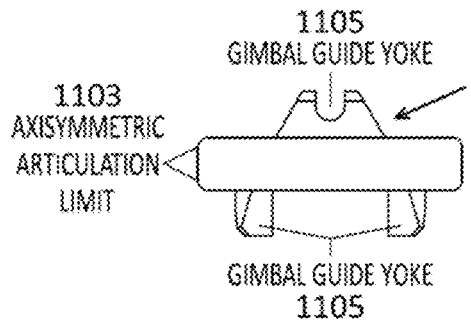
Figure 28C:
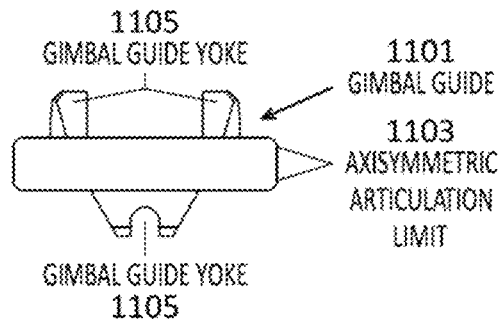

One may consider two alternate options for the gimbal guide design. One, shown in FIG. 27A, is where the yoke axes on the top and bottom of the gimbal guide are parallel or in the same plane, another, where the yoke axes on the top and bottom of the gimbal guide are perpendicular is shown in FIG. 27B. FIGS. 28A-28C illustrate another example of a gimbal guide with orthogonal yoke axes. In FIGS. 28A-28C, the From the exterior, both these choices seem equivalent, as they result in the same end-effector articulation angle, which is equally distributed among the gimbal-guides. However, the consequence of this guide geometry difference is quite significant on the gimbals. This configuration allows the adjacent joint cluster to exist orthogonal about the longitudinal axis to the previous cluster as previously discussed and shown in FIGS. 14A-14C.

Figure 29A:
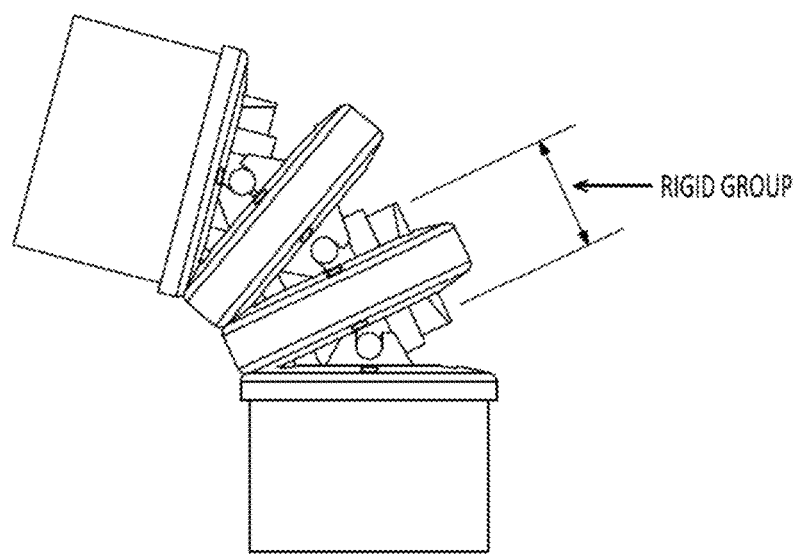
FIG. 29A is an example of a multi-cluster joint having gimbal guides that are oriented with their yokes (on either side of a full gimbal guide) in parallel.

Consider the following two cases. With the parallel yoke gimbal guide one gets the articulation of FIG. 29A. With the perpendicular yoke gimbal guide, one gets the articulation of FIG. 29B. Although the gimbal guides are in the same angular orientation in both cases, the gimbals are not.

Figure 29B:
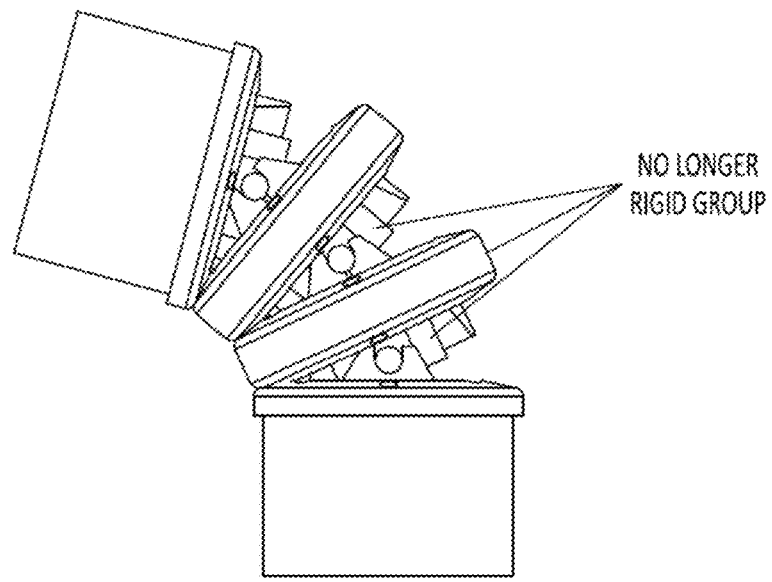
FIG. 29B is an example of a multi-cluster joint having gimbal guides that are oriented with their yokes (on either side of a full gimbal guide) perpendicular.
Figures 30A, 30B:
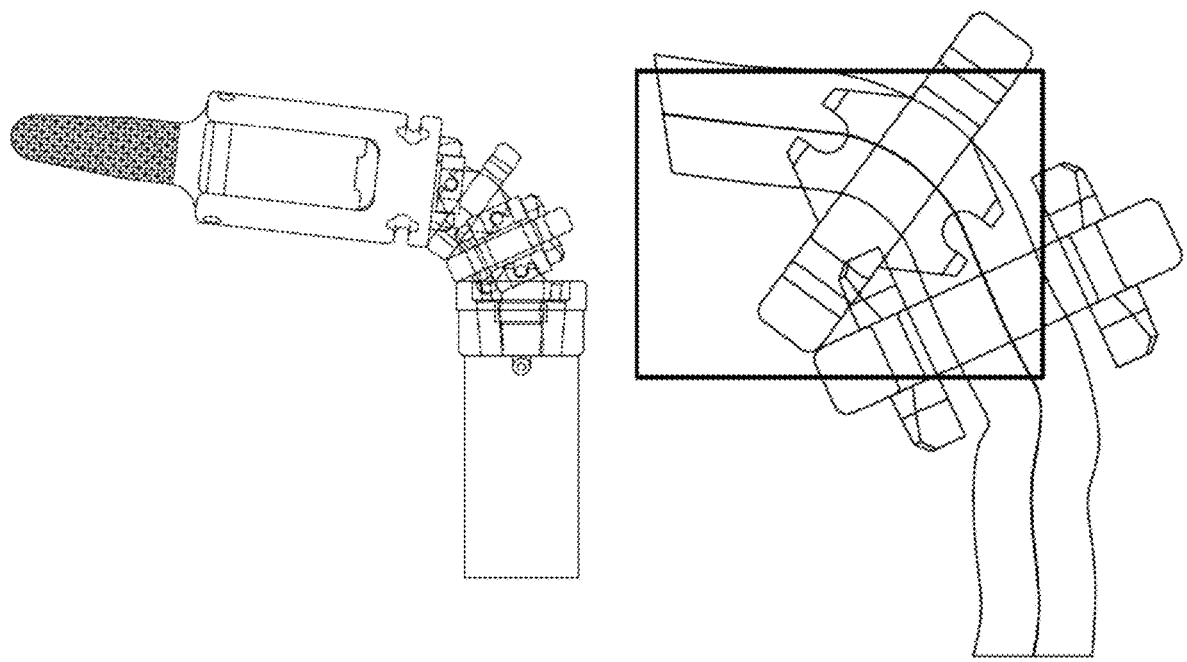
FIG. 30A is a side view of an apparatus including a multi-cluster joint.
FIG. 30B shows enlarged view of the central channel region, showing the cable management guide therein, showing an exemplary profile.

In FIG. 29B, notice that when articulating the end-effector in the same plane as a gimbal guide joint axis, the gimbals sharing a common guide are rigidly parallel to the guide and move as a rigid group. Bending the end-effector results in a non-evenly distributed bend across the gimbals and results in a bend concentration in the cable management guide. FIGS. 30A-30B shows the gimbal guides with perpendicular yoke axes as part of an articulated end-effector. Orienting the gimbal guide joints perpendicular to each other unlocks gimbals sharing a common guide and evenly distributes the bend across the gimbals.

Figure 31A:
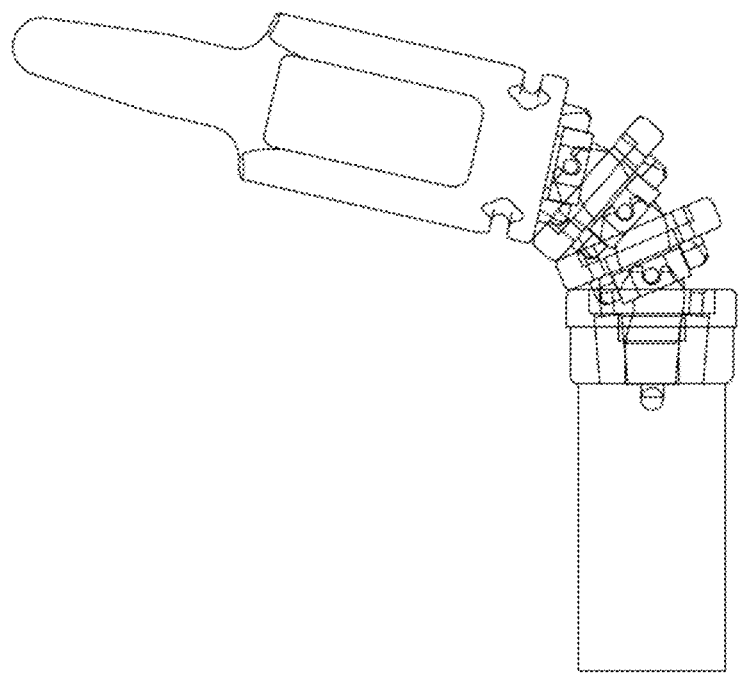
FIG. 31A is another side view of an apparatus including a multi-cluster joint and FIG. 31B shows enlarged view of the central channel region, showing the cable management guide therein, showing an exemplary profile.
Figure 31B:
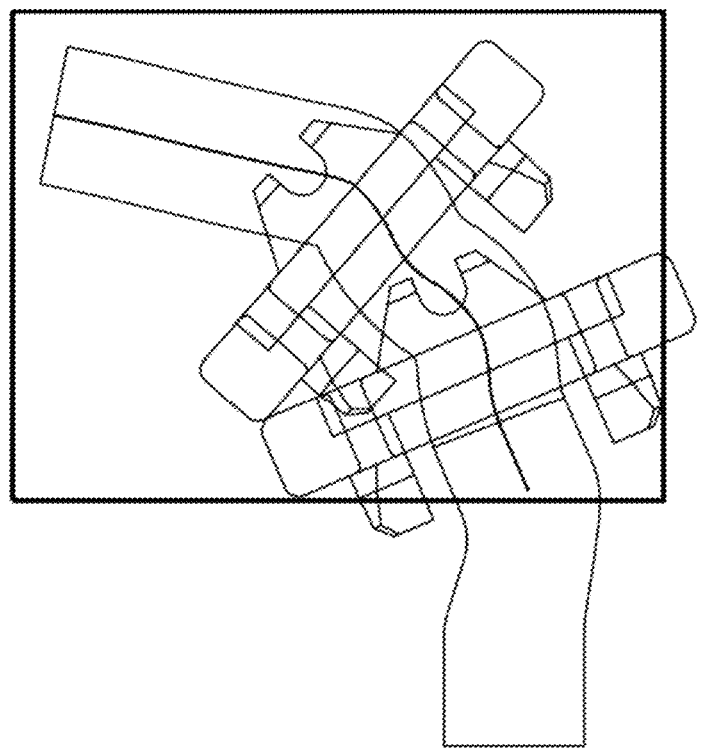

This has a direct implication on the deformed shape of the cable management guide that runs through the central opening of the gimbals 1205. The estimated cable management guide profile for each of the aforementioned cases is shown in FIGS. 31A and 31B, showing a gimbal guide geometry with Parallel Yoke Axes.

FIGS. 30A-31B and 31A-31B, show CAD estimate of conduit profile with parallel yoke gimbal guides in end-effector assembly and transverse configurations. As seen in FIGS. 30A-30B, the cable management guide takes a sharp bend (see box in FIG. 30B) near the fixed jaw due the unequal distribution of bend angle between the gimbals.

Gimbal guides with orthogonal yoke axes may result in an end-effector articulation with equally distributed bend angle among the different gimbals. This leads to a somewhat wavy profile of the cable management guide (see box in FIG. 31B) but avoids any sharp bends.

In all of the above cases, there could be alternate embodiments where the gimbal guides support more than four articulation cables, or where the cables terminate not just on the end guide but selectively at different gimbal guides along the articulating joint.

In summary of the presented cases it can be understood that for a multi-cluster articulation joint, a combination of the universal joint construction confining P and Y rotations to the same planes within joint custers, axisymmetric articulation limits, uniform and small bend radius across all directions of articulation, mitigations of jumpiness and S-bending, through the use of a cable management guide with specific geometry and material properties, can deliver a smoothly articulating joint.

Figure 32:
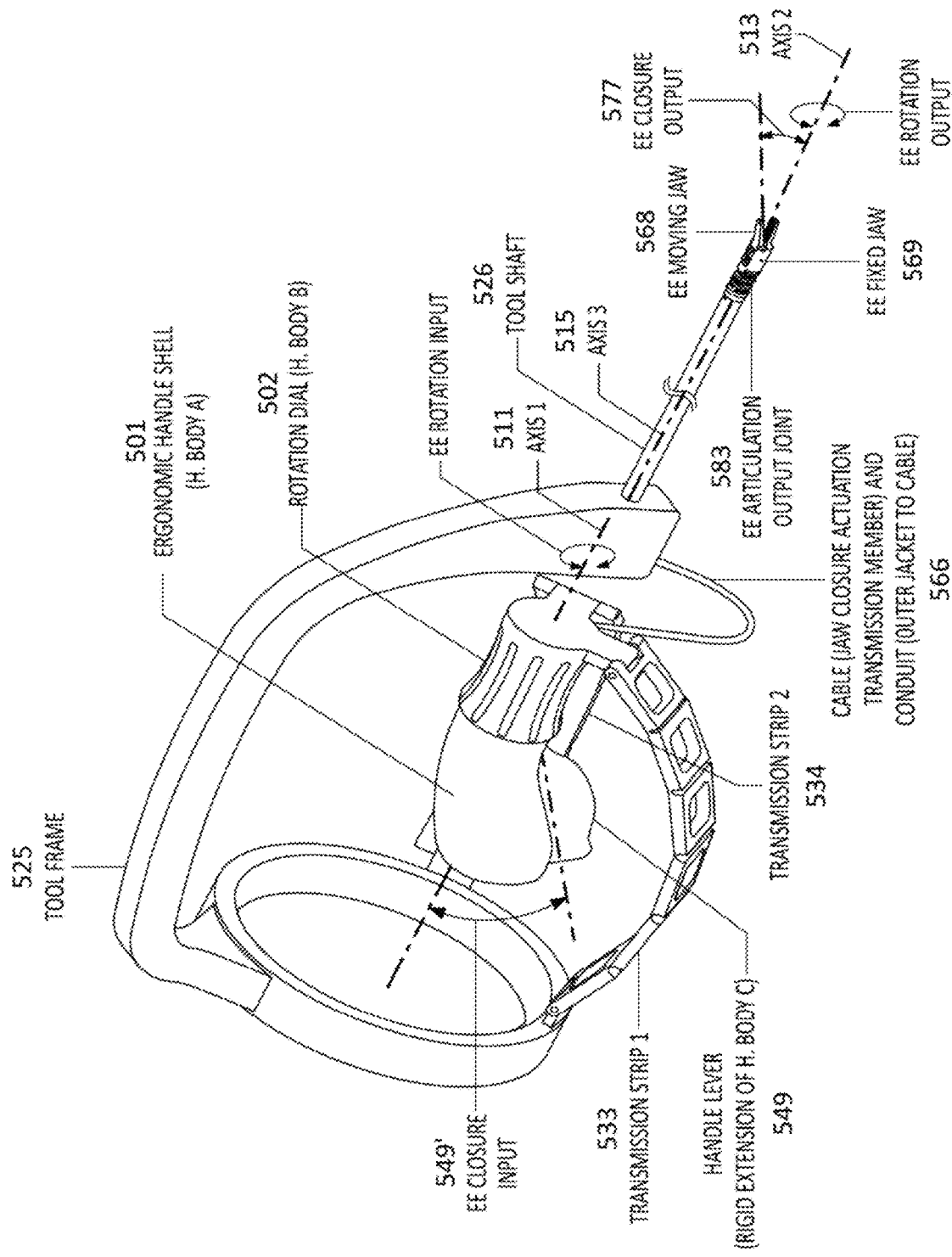
FIG. 32 is an example of a medical device including a multi-cluster joint as described herein.

FIG. 32 illustrates one example of a medical device apparatus including a multi-cluster joint such as any of those described herein. In FIG. 32, the exemplary apparatus includes a tool frame 525, which includes a tool shaft 526 and a forearm attachment portion at the proximal end 527. A cuff (not shown) having a passage therethrough that is configured to hold a wrist or forearm of a user may be coupled to the forearm attachment portion; in some variations via a bearing between the forearm attachment portion of the frame and the cuff that is configured to slide or roll so that there is a roll rotational degree of freedom between the frame and the cuff about the tool axis. A proximal handle assembly may be connected to the tool frame by an input joint. The input joint may be configured to encode motion between the tool frame and the handle assembly, as shown in FIG. 32. In this example, the input joint includes a pair of transmission strips 533, 534 that connect to respective pivoting joints (not shown) in parallel to separately encode pitch and yaw rotations of the handle assembly. The output joint 583 (an end-effector articulation joint) may be any of the multi-cluster joints described herein and is between the end-effector and the tool frame (e.g., tool shaft) receives transmission input (e.g., cables, not shown) from the output joint 533, 534 to articulate the end-effector.

In this example, the handle assembly includes an ergonomic palm grip portion 501 (handle shell) that connects to the rotation dial 502. The handle assembly also includes an end-effector control 549 input (in this example, defining the end-effector actuation transmission cable input 549 for jaw actuation) that is configured as a handle lever and acts as a rigid extension of the internal push rod. A transmission cable 566 connects to the shuttle and acts as a jaw closure actuation transmission member extending from the shuttle and through the tool shaft to the end-effector. This end-effector actuation transmission cable may be enclosed by a protective and/or supporting sheath or cover or conduit, for some or entire portion of its length. The end-effector itself is a jaw assembly including a first (ground) end-effector portion, in this example, including a fixed jaw 569 to which a pivoting second end-effector portion (moving jaw 568) is attached. The end-effector actuation transmission cable 566 may couple to the moving jaw at the end-effector closure output 577.

In FIG. 32, rotation of the dial portion of the handle assembly when the user's forearm is mounted to the proximal end and the palm grip region is held in the user's hand so that the user can rotate the dial between the thumb and fingers, rotates the entire tool frame, and therefore the end-effector that is attached to the distal end of the tool frame via an end-effector output articulating joint. Thus, the handle may rotate about first axis 511 referred to as handle articulated roll axis (axis 1), to cause the tool shaft to rotate in a third axis 515 referred to as the tool shaft roll axis (axis 3), in turn causing the end-effector to roll about a second axis, referred to as an end-effector articulated roll axis (axis 2).

The rotation dial 502 as shown in FIG. 32 is rotated about axis 1 511. The rotation leads to rotation of tool frame 525 via transmission strips 533, 534 (as they constrain rotation DoF), tool shaft 526 (about axis 3 515) and therefore, the end-effector (about axis 2 513). When handle is articulated using the input articulating joint, the output joint (multi-cluster articulation joint 583) and end-effector articulates via the output articulating joint. Now, the center axis (axis 2) for end-effector is different from the axis 3, the shaft axis.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for case of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of articulating a multi-cluster joint at a distal end region of a medical device having a tool shaft, a proximal handle coupled to the tool shaft through an input joint, and an end effector at a distal end of the medical device, the method comprising:
    moving the proximal handle of the medical device in pitch and yaw relative to the tool shaft;
    transmitting the pitch and yaw motion of the handle through the tool shaft to the multi-cluster joint to articulate the multi-cluster joint, wherein the multi-cluster joint comprises a plurality of joint clusters, wherein each joint cluster has a joint cluster axis in a non-articulated state, and wherein each joint cluster provides two orthogonal degrees of rotational freedom, further wherein each joint cluster includes an opening passing through the joint cluster along the joint cluster axis;
    preventing jumping of an end-effector transmission cable within the opening, wherein the opening passes through the each of the joint clusters orthogonal to a cluster plane for each of the joint clusters by preventing lateral movement of the end-effector transmission cable within the cluster plane of each of the joint clusters while permitting the end-effector transmission cable to move axially perpendicular to each cluster plane using a cable management guide routed through the opening passing through the each of the joint clusters orthogonal to the cluster plane so that there is a lateral gap between the openings of the plurality of the joint clusters and the cable management guide;
    preventing buckling of the multi-cluster joint by resisting bending of each joint cluster due to the cable management guide, wherein the cable management guide has a longitudinal axis and a first lumen within which a first length of the end-effector transmission cable extends and a second lumen within which a second length of the end-effector transmission cable extends, wherein the cable management guide limits lateral movement of the first length of the end-effector transmission cable within each opening through the joint clusters while permitting the first length of the end-effector transmission cable and the second length of the end-effector transmission cable to move axially along the longitudinal axis of the cable management guide;
    further wherein the cable management guide is secured to the plurality of joint clusters to prevent rotation of the cable management guide relative to the multi-cluster joint about the longitudinal axis of the cable management guide; and
    actuating the end effector by pulling the end-effector transmission cable proximally.

2. The method of claim 1, wherein preventing buckling comprises preventing buckling because of a stiffness of the cable management guide, which has a Young's Modulus of greater than 0.1 GPa.

3. The method of claim 1, further comprising preventing rotation of the cable management guide relative to any joint cluster as the multi-cluster joint is actuated.

4. The method of claim 1, wherein each joint cluster has a same minimum bend radius in any direction of articulation that is 1.2× or less than a diameter of the multi-cluster joint and includes a first half-gimbal guide, a second half-gimbal guide, and a gimbal having a pair of orthogonal gimbal spindles in a cluster plane, wherein the gimbal is positioned between the first half-gimbal guide and the second half-gimbal guide.

5. The method of claim 1, wherein the cable management guide is secured to at least one of: one or more of the plurality of joint clusters, one or more gimbals in one or more of the plurality of joint clusters, one or more half gimbal-guides in one or more of the plurality of joint clusters, the end-effector, and the tool shaft, to prevent rotation of the cable management guide relative to the multi-cluster joint about the longitudinal axis of the cable management guide.

6. The method of claim 1, wherein the first length of the end-effector transmission cable is a flexible cable that is highly compliant in bending.

7. The method of claim 1, further comprising articulating the multi-cluster joint by articulating a set of articulation cables extending from an articulation input through the multi-cluster joint and positioned laterally outside of the openings of the joint clusters.

8. The method of claim 1, wherein actuating the end effector comprises opening or closing jaws.

9. The method of claim 1, further comprising inserting the medical device into a body.

10. A method of articulating a multi-cluster joint at a distal end region of a medical device having an elongate tool shaft, a proximal handle coupled to the tool shaft through an input joint, and an end effector at a distal end of the medical device, the method comprising:
    moving the proximal handle of the medical device in pitch and yaw relative to the tool shaft;
    transmitting the pitch and yaw motion of the handle through the elongate tool shaft to the multi-cluster joint to articulate the multi-cluster joint, wherein the multi-cluster joint comprises a plurality of joint clusters, wherein each joint cluster has a joint cluster axis in a non-articulated state, and wherein each joint cluster provides two orthogonal degrees of rotational freedom, further wherein each joint cluster includes an opening passing through the joint cluster along the joint cluster axis;

preventing jumping of an end-effector transmission cable within the opening, wherein the opening passes through the each of the joint clusters orthogonal to a plane of the cluster by preventing lateral movement of the end-effector transmission cable within each cluster plane while permitting the end-effector transmission cable to move axially perpendicular to each cluster plane using a cable management guide routed through the opening passing through the each of the joint clusters orthogonal to the plane of the cluster so that there is a lateral gap between the openings of the plurality of the joint clusters and the cable management guide;

preventing buckling of the multi-cluster joint by resisting bending of each joint cluster due to the cable management guide, wherein the cable management guide comprises an elongate, tubular body having a longitudinal axis, a first lumen guiding a first length of the end-effector transmission cable and a second lumen guiding a second length of the end-effector transmission cable, wherein the cable management guide limits lateral movement of the first and second end-effector transmission cable lengths within central openings of the joint clusters while permitting the first and second end-effector transmission cable lengths to move axially along the longitudinal axis of the cable management guide, further wherein the cable management guide is secured to one or more of the plurality of joint clusters to prevent rotation of the cable management guide relative to the multi-cluster joint about the longitudinal axis of the cable management guide; and actuating the end effector by actuating a control or button or lever on the handle that results in pulling the first length of the end-effector transmission cable proximally.

11. The method of claim 10, wherein preventing buckling comprises preventing buckling because of a stiffness of the cable management guide, which has a Young's Modulus of greater than 0.1 GPa.

12. The method of claim 10, further comprising preventing rotation of the cable management guide relative to any joint cluster as the multi-cluster joint is actuated.

13. The method of claim 10, wherein each joint cluster has a same minimum bend radius in any direction of articulation that is 1.2× or less than a diameter of the multi-cluster joint and includes a first half-gimbal guide, a second half-gimbal guide, and a gimbal having a pair of orthogonal gimbal spindles in a cluster plane, wherein the gimbal is positioned between the first half-gimbal guide and the second half-gimbal guide.

14. The method of claim 10, wherein the cable management guide is secured to at least one of: one or more of the plurality of joint clusters, one or more gimbals in one or more of the plurality of joint clusters, one or more half gimbal-guides in one or more of the plurality of joint clusters, the end-effector, and the tool shaft, to prevent rotation of the cable management guide relative to the multi-cluster joint about the longitudinal axis of the cable management guide.

15. The method of claim 10, wherein the first length of end-effector transmission cable is a flexible cable that is highly compliant in bending.

16. The method of claim 10, further comprising articulating the multi-cluster joint by articulating a set of articulation cables extending from an articulation input through the multi-cluster joint and positioned laterally outside of the openings of the joint clusters.

17. The method of claim 10, wherein actuating the end effector comprises opening or closing jaws.

18. The method of claim 10, further comprising inserting the medical device into a body.

* * * * *